(12) United States Patent
Bayramov et al.

(10) Patent No.: US 11,565,097 B2
(45) Date of Patent: *Jan. 31, 2023

(54) MICROARRAY FOR DELIVERY OF THERAPEUTIC AGENT AND METHODS OF USE

(71) Applicant: Corium Pharma Solutions, Inc., Boston, MA (US)

(72) Inventors: Danir Bayramov, Irvine, CA (US); Guohua Chen, Sunnyvale, CA (US); Zhongli Ding, Sunnyvale, CA (US); Esi Ghartey-Tagoe, San Jose, CA (US); Parminder Singh, Union City, CA (US); Doug Bourne, Campbell, CA (US)

(73) Assignee: Corium Pharma Solutions, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/513,613

(22) Filed: Jul. 16, 2019

(65) Prior Publication Data

US 2019/0336741 A1 Nov. 7, 2019

Related U.S. Application Data

(63) Continuation of application No. 14/210,402, filed on Mar. 13, 2014, now Pat. No. 10,384,046.

(60) Provisional application No. 61/799,304, filed on Mar. 15, 2013.

(51) Int. Cl.
*A61M 37/00* (2006.01)
*A61K 9/00* (2006.01)

(52) U.S. Cl.
CPC ....... *A61M 37/0015* (2013.01); *A61K 9/0021* (2013.01)

(58) Field of Classification Search
None
See application file for complete search history.

(56) References Cited

U.S. PATENT DOCUMENTS

| | | |
|---|---|---|
| 1,554,510 A | 9/1925 | Kirby |
| 1,770,632 A | 7/1930 | Smith |
| 2,046,240 A | 6/1936 | Bayley |
| 2,434,407 A | 1/1948 | George |
| 3,675,766 A | 7/1972 | Rosenthal |
| 3,704,194 A | 11/1972 | Harrier et al. |
| 3,814,097 A | 6/1974 | Ganderton et al. |
| 3,873,255 A | 3/1975 | Kalwaites |
| 3,918,449 A | 11/1975 | Pistor |
| 3,964,482 A | 6/1976 | Gerstel et al. |
| 4,055,029 A | 10/1977 | Kalbow |
| 4,117,841 A | 10/1978 | Perrotta et al. |
| 4,151,240 A | 4/1979 | Lucas et al. |
| 4,180,232 A | 12/1979 | Hardigg |
| 4,342,314 A | 8/1982 | Radel et al. |
| 4,381,963 A | 5/1983 | Goldstein et al. |
| 4,395,215 A | 7/1983 | Bishop |
| 4,402,696 A | 9/1983 | Gulko |
| 4,460,368 A | 7/1984 | Allison et al. |
| 4,460,370 A | 7/1984 | Allison et al. |
| 4,463,045 A | 7/1984 | Ahr et al. |
| 4,509,908 A | 4/1985 | Mullane, Jr. |
| 4,515,168 A | 5/1985 | Chester et al. |
| 4,556,441 A | 12/1985 | Faasse, Jr. |
| 4,585,991 A | 4/1986 | Reid et al. |
| 4,597,961 A | 7/1986 | Etscorn |
| 4,609,518 A | 9/1986 | Curro et al. |
| 4,630,603 A | 12/1986 | Greenway |
| 4,660,721 A | 4/1987 | Mykleby |
| 4,695,422 A | 9/1987 | Curro et al. |
| 4,743,234 A | 5/1988 | Leopoldi et al. |
| 4,743,249 A | 5/1988 | Loveland |
| 4,784,737 A | 11/1988 | Ray et al. |
| 4,812,305 A | 3/1989 | Vocal |
| 4,837,049 A | 6/1989 | Byers et al. |
| 4,846,821 A | 7/1989 | Lyons et al. |
| 4,904,475 A | 2/1990 | Gale et al. |
| 4,996,159 A | 2/1991 | Glaser |
| 5,051,259 A | 9/1991 | Olsen et al. |
| 5,061,258 A | 10/1991 | Martz |
| 5,134,079 A | 7/1992 | Cusak et al. |
| 5,139,029 A | 8/1992 | Fishman et al. |
| 5,156,591 A | 10/1992 | Gross et al. |
| 5,158,073 A | 10/1992 | Bukowski |
| 5,160,315 A | 11/1992 | Heinecke et al. |
| 5,162,043 A | 11/1992 | Lew et al. |
| 5,163,918 A | 11/1992 | Righi et al. |
| 5,190,558 A | 3/1993 | Ito |
| 5,198,192 A | 3/1993 | Saito et al. |

(Continued)

FOREIGN PATENT DOCUMENTS

| | | |
|---|---|---|
| CA | 2205444 | 6/1996 |
| CA | 2376285 | 12/2000 |

(Continued)

OTHER PUBLICATIONS

Makaida (Makaida, H.K., et al., Poly Lactic-co-Glycolic Acid (PLGA) as Biodegradable Controlled Drug Delivery Carrier, Polymers (Basel). Sep. 1, 2011; 3(3): 1377-1397).*

International Search Report from International Patent Application No. PCT/US2016/039864 dated Sep. 23, 2016.

Avcin et al., "Subcutaneous nodule after vaccination with an aluminum-containing vaccina", Acta Dermatoven, APA, vol. 17, No. 4, pp. 182-184 (2008).

Chun, et al.,"An array of hollow microcapillaries for the controlled injection of genetic materials into animal/plant cells," IEEE Workshop on Micro Electro Mechanical Systems, pp. 406-411, (1999).

(Continued)

*Primary Examiner* — H. Sarah Park

(74) *Attorney, Agent, or Firm* — Goodwin Procter LLP

(57) ABSTRACT

Microstructure arrays and methods for using and manufacturing the arrays are described.

17 Claims, 15 Drawing Sheets

(56) References Cited

U.S. PATENT DOCUMENTS

| | | |
|---|---|---|
| 5,215,088 A | 6/1993 | Normann et al. |
| 5,244,677 A | 9/1993 | Kreckel et al. |
| 5,244,711 A | 9/1993 | Drelich et al. |
| 5,250,023 A | 10/1993 | Lee et al. |
| 5,250,067 A | 10/1993 | Gelfer et al. |
| 5,252,279 A | 10/1993 | Gore et al. |
| 5,256,360 A | 10/1993 | Li |
| 5,279,544 A | 1/1994 | Gross et al. |
| 5,308,625 A | 5/1994 | Wong et al. |
| 5,318,557 A | 6/1994 | Gross |
| 5,320,600 A | 6/1994 | Lambert |
| 5,330,452 A | 7/1994 | Zook |
| 5,362,307 A | 11/1994 | Guy et al. |
| 5,383,512 A | 1/1995 | Jarvis |
| 5,457,041 A | 10/1995 | Ginaven et al. |
| 5,462,743 A | 10/1995 | Turner et al. |
| 5,476,443 A | 12/1995 | Cartmell et al. |
| 5,487,726 A | 1/1996 | Rabineau et al. |
| 5,496,304 A | 3/1996 | Chasan |
| 5,498,235 A | 3/1996 | Flower |
| 5,503,843 A | 4/1996 | Santus et al. |
| 5,512,219 A | 4/1996 | Rowland et al. |
| 5,520,629 A | 5/1996 | Heinecke et al. |
| 5,527,287 A | 6/1996 | Miskinyar |
| 5,527,288 A | 6/1996 | Gross et al. |
| 5,531,675 A | 7/1996 | Yoo |
| 5,531,855 A | 7/1996 | Heinecke et al. |
| 5,536,263 A | 7/1996 | Rolf et al. |
| 5,551,953 A | 9/1996 | Lattin et al. |
| 5,567,376 A | 10/1996 | Turi et al. |
| 5,569,469 A | 10/1996 | Lovrechich |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,662,127 A | 9/1997 | De Vaughn |
| 5,676,850 A | 10/1997 | Reed et al. |
| 5,681,580 A | 10/1997 | Jang et al. |
| 5,697,901 A | 12/1997 | Ericksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,730,721 A | 3/1998 | Hyatt et al. |
| 5,735,273 A | 4/1998 | Kurnik et al. |
| 5,738,642 A | 4/1998 | Heinecke et al. |
| 5,756,117 A | 5/1998 | D'Angelo et al. |
| 5,771,890 A | 6/1998 | Tamada |
| 5,788,983 A | 8/1998 | Chien et al. |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,843,114 A | 12/1998 | Jang |
| 5,848,985 A | 12/1998 | Muroki |
| 5,848,990 A | 12/1998 | Cirelli et al. |
| 5,848,991 A | 12/1998 | Gross et al. |
| 5,851,549 A | 12/1998 | Svec |
| 5,855,801 A | 1/1999 | Lin et al. |
| 5,868,244 A | 2/1999 | Ivanov et al. |
| 5,873,849 A | 2/1999 | Bernard |
| 5,879,326 A | 3/1999 | Godshall et al. |
| 5,900,252 A | 5/1999 | Calanchi et al. |
| 5,932,240 A | 8/1999 | D'Angelo et al. |
| 5,938,684 A | 8/1999 | Lynch et al. |
| 5,948,488 A | 9/1999 | Marecki et al. |
| 5,962,011 A | 10/1999 | Devillez et al. |
| 5,964,729 A | 10/1999 | Choi et al. |
| 5,983,136 A | 11/1999 | Kamen |
| 5,987,989 A | 11/1999 | Yamamoto et al. |
| 5,997,549 A | 12/1999 | Sauceda et al. |
| 5,997,986 A | 12/1999 | Turi et al. |
| 6,014,584 A | 1/2000 | Hofmann et al. |
| 6,023,629 A | 2/2000 | Tamada |
| 6,024,553 A | 2/2000 | Shimalla |
| 6,036,659 A | 3/2000 | Ray et al. |
| 6,038,465 A | 3/2000 | Melton, Jr. |
| 6,038,485 A | 3/2000 | Axelgaard |
| 6,047,208 A | 4/2000 | Flower |
| 6,050,988 A | 4/2000 | Zuck |
| 6,055,453 A | 4/2000 | Hofmann et al. |
| 6,080,172 A | 6/2000 | Fujiwara et al. |
| 6,083,196 A | 7/2000 | Trautman et al. |
| 6,091,975 A | 7/2000 | Daddona et al. |
| 6,106,751 A | 8/2000 | Talbot et al. |
| 6,120,792 A | 9/2000 | Juni |
| 6,129,696 A | 10/2000 | Sibalis |
| 6,132,449 A | 10/2000 | Lum et al. |
| 6,132,755 A | 10/2000 | Eicher et al. |
| 6,135,990 A | 10/2000 | Heller et al. |
| 6,136,008 A | 10/2000 | Becker et al. |
| 6,156,336 A | 12/2000 | Bracht |
| 6,169,224 B1 | 1/2001 | Heinecke et al. |
| 6,181,964 B1 | 1/2001 | Hofmann et al. |
| 6,183,434 B1 | 2/2001 | Eppstein |
| 6,183,770 B1 | 2/2001 | Muchin et al. |
| 6,187,210 B1 | 2/2001 | Lebouitz et al. |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,248,120 B1 | 6/2001 | Wyszogrodzki |
| 6,256,533 B1 | 7/2001 | Yuzhakov et al. |
| 6,293,925 B1 | 9/2001 | Safabash et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,355,054 B1 | 3/2002 | Neuberger |
| 6,375,627 B1 | 4/2002 | Mauze et al. |
| 6,375,870 B1 | 4/2002 | Visovsky et al. |
| 6,375,978 B1 | 4/2002 | Kliener et al. |
| 6,379,324 B1 | 4/2002 | Garstein et al. |
| 6,440,096 B1 | 8/2002 | Lastovich et al. |
| 6,451,240 B1 | 9/2002 | Sherman et al. |
| 6,471,903 B2 | 10/2002 | Sherman et al. |
| 6,476,288 B1 | 11/2002 | Van Rijswijck et al. |
| 6,485,470 B2 | 11/2002 | Hostettler et al. |
| 6,494,830 B1 | 12/2002 | Wessel |
| 6,503,231 B1 | 1/2003 | Prausnitz et al. |
| 6,508,947 B2 | 1/2003 | Gulvin et al. |
| 6,511,463 B1 | 1/2003 | Wood et al. |
| 6,512,626 B1 | 1/2003 | Schmidt |
| 6,516,223 B2 | 2/2003 | Hofmann |
| 6,532,386 B2 | 3/2003 | Sun et al. |
| 6,533,884 B1 | 3/2003 | Mallik |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,585,742 B2 | 7/2003 | Stough |
| 6,589,202 B1 | 7/2003 | Powell |
| 6,591,124 B2 | 7/2003 | Sherman et al. |
| 6,591,133 B1 | 7/2003 | Joshi |
| 6,603,987 B2 | 8/2003 | Whiston |
| 6,610,463 B1 | 8/2003 | Ohkura et al. |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,685,682 B1 | 2/2004 | Heinecke et al. |
| 6,689,103 B1 | 2/2004 | Palasis |
| 6,691,752 B2 | 2/2004 | DiSabatino |
| 6,743,211 B1 | 6/2004 | Prausnitz et al. |
| 6,767,341 B2 | 7/2004 | Cho |
| 6,770,480 B1 | 8/2004 | Canham |
| 6,778,853 B1 | 8/2004 | Heller et al. |
| 6,780,171 B2 | 8/2004 | Gabel et al. |
| 6,808,506 B2 | 10/2004 | Lastovich et al. |

(56) References Cited

U.S. PATENT DOCUMENTS

| | | |
|---|---|---|
| 6,821,281 B2 | 11/2004 | Sherman et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 6,980,855 B2 | 12/2005 | Cho et al. |
| 6,991,809 B2 | 1/2006 | Anderson |
| 7,011,844 B2 | 3/2006 | Gale et al. |
| 7,048,723 B1 | 5/2006 | Frazier et al. |
| 7,062,317 B2 | 6/2006 | Avrahami et al. |
| 7,087,035 B2 | 8/2006 | Trautman et al. |
| 7,097,631 B2 | 8/2006 | Trautman et al. |
| 7,108,681 B2 | 9/2006 | Gartstein et al. |
| 7,115,108 B2 | 10/2006 | Wilkinson et al. |
| 7,128,730 B2 | 10/2006 | Marano-Ford et al. |
| 7,131,960 B2 | 11/2006 | Trautman et al. |
| 7,131,987 B2 | 11/2006 | Sherman et al. |
| 7,166,086 B2 | 1/2007 | Haider et al. |
| 7,184,826 B2 | 2/2007 | Cormier et al. |
| 7,186,235 B2 | 3/2007 | Martin et al. |
| 7,226,439 B2 | 6/2007 | Prausnitz et al. |
| 7,332,339 B2 | 2/2008 | Canham |
| 7,412,284 B2 | 8/2008 | Hofmann |
| 7,416,541 B2 | 8/2008 | Yuzhakov et al. |
| 7,419,481 B2 | 9/2008 | Trautman et al. |
| 7,572,405 B2 | 8/2009 | Sherman et al. |
| 7,578,954 B2 | 8/2009 | Gartstein et al. |
| 7,578,985 B2 | 8/2009 | Aderhold et al. |
| 7,611,481 B2 | 11/2009 | Cleary et al. |
| 7,658,728 B2 | 2/2010 | Yuzhakov |
| 7,678,777 B2 | 3/2010 | Yasuda et al. |
| 7,763,203 B2 | 7/2010 | Arias et al. |
| 7,785,301 B2 | 8/2010 | Yuzhakov |
| 7,789,733 B2 | 9/2010 | Sugimura |
| 7,798,987 B2 | 9/2010 | Trautman et al. |
| 7,828,827 B2 | 11/2010 | Gartstein et al. |
| 7,846,488 B2 | 12/2010 | Johnson |
| 7,914,480 B2 | 3/2011 | Cleary et al. |
| 8,057,842 B2 | 11/2011 | Choi et al. |
| 8,062,573 B2 | 11/2011 | Kwon |
| 8,216,190 B2 | 7/2012 | Gartstein et al. |
| 8,267,889 B2 | 9/2012 | Cantor et al. |
| 8,366,677 B2 | 2/2013 | Kaspar et al. |
| 8,696,638 B2 | 4/2014 | Terahara et al. |
| 8,702,726 B2 | 4/2014 | Gartstein et al. |
| 8,734,697 B2 | 5/2014 | Chen et al. |
| 8,747,362 B2 | 6/2014 | Terahara |
| 8,771,781 B2 | 7/2014 | Tokumoto et al. |
| 8,821,446 B2 | 9/2014 | Trautman et al. |
| 8,834,423 B2 | 9/2014 | Falo, Jr. et al. |
| 8,900,180 B2 | 12/2014 | Wolter et al. |
| 8,911,749 B2 | 12/2014 | Ghartey-Tagoe et al. |
| 9,114,238 B2 | 8/2015 | Singh et al. |
| 9,220,678 B2 | 12/2015 | Kendall et al. |
| 9,452,280 B2 | 9/2016 | Singh et al. |
| 9,498,524 B2 | 11/2016 | Ghartey-Tagoe et al. |
| 9,549,746 B2 | 1/2017 | Woolfsen et al. |
| 9,687,640 B2 | 6/2017 | Trautman et al. |
| 9,687,641 B2 | 6/2017 | Singh et al. |
| 9,962,534 B2 | 5/2018 | Chen et al. |
| 10,195,409 B2 | 2/2019 | Bourne et al. |
| 10,238,848 B2 | 3/2019 | Singh et al. |
| 10,245,422 B2 | 4/2019 | Le et al. |
| 10,384,045 B2 | 8/2019 | Ding et al. |
| 10,384,046 B2 | 8/2019 | Bayramov et al. |
| 2001/0023324 A1 | 9/2001 | Pronovost et al. |
| 2001/0023351 A1 | 9/2001 | Eilers et al. |
| 2002/0006355 A1 | 1/2002 | Whitson |
| 2002/0016562 A1 | 2/2002 | Cormier et al. |
| 2002/0020688 A1 | 2/2002 | Sherman et al. |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0096488 A1 | 7/2002 | Gulvin et al. |
| 2002/0123675 A1 | 9/2002 | Trautman et al. |
| 2002/0128599 A1 | 9/2002 | Cormier et al. |
| 2002/0133129 A1 | 9/2002 | Arias et al. |
| 2002/0133137 A1 | 9/2002 | Hofmann |
| 2002/0138049 A1 | 9/2002 | Allen et al. |
| 2002/0169411 A1 | 11/2002 | Sherman et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0188310 A1 | 12/2002 | Seward et al. |
| 2002/0193729 A1 | 12/2002 | Cormier et al. |
| 2002/0193819 A1 | 12/2002 | Porter et al. |
| 2003/0083645 A1 | 5/2003 | Angel et al. |
| 2003/0093028 A1 | 5/2003 | Spiegel |
| 2003/0093089 A1 | 5/2003 | Greenberg |
| 2003/0135167 A1 | 7/2003 | Gonnelli |
| 2003/0166624 A1 | 9/2003 | Gale et al. |
| 2003/0187394 A1 | 10/2003 | Wilkinson et al. |
| 2003/0195474 A1 | 10/2003 | Down et al. |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2003/0220610 A1 | 11/2003 | Lastovich et al. |
| 2003/0220656 A1 | 11/2003 | Gartstein et al. |
| 2004/0049150 A1 | 3/2004 | Dalton et al. |
| 2004/0053894 A1 | 3/2004 | Mazess et al. |
| 2004/0062813 A1 | 4/2004 | Cormier et al. |
| 2004/0087893 A1 | 5/2004 | Kwon |
| 2004/0087992 A1 | 5/2004 | Gartstein et al. |
| 2004/0096455 A1 | 5/2004 | Maa et al. |
| 2004/0106904 A1 | 6/2004 | Gonnelli et al. |
| 2004/0143211 A1 | 7/2004 | Haider et al. |
| 2004/0146611 A1 | 7/2004 | Arias et al. |
| 2004/0164454 A1 | 8/2004 | Gartstein et al. |
| 2004/0181203 A1 | 9/2004 | Cormier et al. |
| 2004/0186419 A1 | 9/2004 | Cho |
| 2004/0204669 A1 | 10/2004 | Hofmann |
| 2004/0220535 A1 | 11/2004 | Canham |
| 2004/0236271 A1 | 11/2004 | Theeuwes et al. |
| 2004/0265365 A1 | 12/2004 | Daddona et al. |
| 2005/0049549 A1 | 3/2005 | Wong et al. |
| 2005/0065463 A1 | 3/2005 | Tobinga et al. |
| 2005/0089554 A1 | 4/2005 | Cormier et al. |
| 2005/0090803 A1 | 4/2005 | Sherman et al. |
| 2005/0096586 A1 | 5/2005 | Trautman et al. |
| 2005/0163827 A1 | 7/2005 | Zech et al. |
| 2005/0178760 A1 | 8/2005 | Chang et al. |
| 2005/0197308 A1 | 9/2005 | Dalton |
| 2005/0209565 A1 | 9/2005 | Yuzhakov et al. |
| 2005/0228340 A1 | 10/2005 | Cleary et al. |
| 2005/0256045 A1 | 11/2005 | Ameri et al. |
| 2005/0261631 A1 | 11/2005 | Clarke et al. |
| 2005/0271684 A1 | 12/2005 | Trautman et al. |
| 2006/0024358 A1 | 2/2006 | Santini et al. |
| 2006/0067943 A1 | 3/2006 | Maa et al. |
| 2006/0076718 A1 | 4/2006 | Sherman et al. |
| 2006/0095061 A1 | 5/2006 | Trautman et al. |
| 2006/0108914 A1 | 5/2006 | Young |
| 2006/0129174 A1 | 6/2006 | Gartstein et al. |
| 2006/0134188 A1 | 6/2006 | Podhaisky et al. |
| 2006/0149297 A1 | 7/2006 | Sherman et al. |
| 2006/0253079 A1 | 11/2006 | McDonough et al. |
| 2007/0027427 A1 | 2/2007 | Trautman et al. |
| 2007/0078414 A1 | 4/2007 | McAllister et al. |
| 2007/0191761 A1 | 8/2007 | Boone et al. |
| 2007/0224377 A1 | 9/2007 | Leimbacher et al. |
| 2007/0255251 A1 | 11/2007 | Panchula et al. |
| 2008/0009811 A1 | 1/2008 | Cantor |
| 2008/0009825 A1 | 1/2008 | Ringsred et al. |
| 2008/0039805 A1 | 2/2008 | Frederickson et al. |
| 2008/0063866 A1 | 3/2008 | Allen et al. |
| 2008/0114298 A1 | 5/2008 | Cantor et al. |

(56) References Cited

U.S. PATENT DOCUMENTS

| | | |
|---|---|---|
| 2008/0125743 A1 | 5/2008 | Yuzhakov |
| 2008/0183144 A1 | 7/2008 | Trautman et al. |
| 2008/0188771 A1 | 8/2008 | Boecker et al. |
| 2008/0195035 A1 | 8/2008 | Fredrickson et al. |
| 2008/0200883 A1 | 8/2008 | Tomono |
| 2008/0208134 A1 | 8/2008 | Tomono |
| 2008/0208146 A1 | 8/2008 | Brandwein et al. |
| 2008/0214987 A1 | 9/2008 | Xu |
| 2008/0221532 A1 | 9/2008 | Ogawa |
| 2008/0262444 A1 | 10/2008 | Takada |
| 2008/0269685 A1 | 10/2008 | Singh et al. |
| 2009/0017210 A1 | 1/2009 | Andrianov et al. |
| 2009/0035446 A1 | 2/2009 | Kwon |
| 2009/0041810 A1 | 2/2009 | Andrianov et al. |
| 2009/0043279 A1 | 2/2009 | Kaspar et al. |
| 2009/0155330 A1 | 6/2009 | Ghartey-Tagoe et al. |
| 2009/0182306 A1 | 7/2009 | Lee et al. |
| 2009/0216215 A1 | 8/2009 | Thalmann et al. |
| 2009/0234301 A1 | 9/2009 | Tomono |
| 2010/0004608 A1 | 1/2010 | Hamamoto et al. |
| 2010/0028390 A1 | 2/2010 | Cleary et al. |
| 2010/0200494 A1 | 8/2010 | Storer |
| 2010/0228203 A1 | 9/2010 | Quan et al. |
| 2010/0247698 A1 | 9/2010 | Zhang et al. |
| 2011/0006458 A1 | 1/2011 | Sagi et al. |
| 2011/0028905 A1 | 2/2011 | Takada |
| 2011/0046638 A1 | 2/2011 | Gartstein et al. |
| 2011/0059150 A1 | 3/2011 | Kendall et al. |
| 2011/0098651 A1 | 4/2011 | Falo et al. |
| 2011/0121486 A1 | 5/2011 | Oh et al. |
| 2011/0160069 A1 | 6/2011 | Corrie et al. |
| 2011/0165236 A1 | 7/2011 | Chow et al. |
| 2011/0177139 A1 | 7/2011 | Hyungil et al. |
| 2011/0195124 A1* | 8/2011 | Jin .................... A61K 9/0021 424/486 |
| 2011/0276027 A1 | 11/2011 | Trautman et al. |
| 2011/0276028 A1 | 11/2011 | Singh et al. |
| 2011/0280800 A1 | 11/2011 | Wu et al. |
| 2011/0288484 A1 | 11/2011 | Kendall et al. |
| 2011/0288485 A1 | 11/2011 | Tokumoto et al. |
| 2011/0295205 A1 | 12/2011 | Kaufmann et al. |
| 2011/0306853 A1 | 12/2011 | Black et al. |
| 2012/0052120 A1 | 3/2012 | Castor |
| 2012/0123297 A1 | 5/2012 | Brancazio |
| 2012/0123387 A1 | 5/2012 | Gonzalez et al. |
| 2012/0130306 A1 | 5/2012 | Terahara et al. |
| 2012/0150023 A1 | 6/2012 | Kaspar et al. |
| 2012/0184906 A1 | 7/2012 | McAllister |
| 2012/0330250 A1 | 12/2012 | Kuwahara et al. |
| 2013/0131598 A1 | 5/2013 | Trautman et al. |
| 2013/0150822 A1 | 6/2013 | Ross |
| 2013/0156849 A1 | 6/2013 | De Fougerolles et al. |
| 2013/0287832 A1 | 10/2013 | O'Hagan et al. |
| 2013/0292868 A1 | 11/2013 | Singh et al. |
| 2013/0292886 A1 | 11/2013 | Sagi et al. |
| 2013/0303502 A1 | 11/2013 | Cavanagh et al. |
| 2014/0148846 A1 | 5/2014 | Pereira et al. |
| 2014/0180201 A1 | 6/2014 | Ding et al. |
| 2014/0248312 A1 | 9/2014 | Rappuoli et al. |
| 2014/0257188 A1 | 9/2014 | Kendall et al. |
| 2014/0272101 A1 | 9/2014 | Chen et al. |
| 2014/0276366 A1 | 9/2014 | Bourne et al. |
| 2014/0276378 A1 | 9/2014 | Chen et al. |
| 2014/0276474 A1 | 9/2014 | Ding et al. |
| 2014/0276580 A1 | 9/2014 | Le et al. |
| 2014/0276589 A1 | 9/2014 | Bayramov et al. |
| 2014/0330198 A1 | 11/2014 | Zhang et al. |
| 2015/0079133 A1 | 3/2015 | Ghartey-Tagoe et al. |
| 2015/0238413 A1 | 8/2015 | Mochizuki et al. |
| 2015/0297878 A1 | 10/2015 | Singh et al. |
| 2016/0015952 A1 | 1/2016 | Omachi et al. |
| 2016/0058992 A1 | 3/2016 | Chen et al. |
| 2016/0067176 A1 | 3/2016 | Ding et al. |
| 2016/0135895 A1 | 5/2016 | Faasse et al. |
| 2016/0175572 A1 | 6/2016 | Crowley et al. |
| 2016/0374939 A1 | 12/2016 | Shastry et al. |
| 2017/0050010 A1 | 2/2017 | Mcallister et al. |
| 2017/0217656 A1 | 8/2017 | Yamada |
| 2017/0281535 A1 | 10/2017 | Singh et al. |
| 2017/0361079 A1 | 12/2017 | Trautman et al. |
| 2019/0001109 A1 | 1/2019 | Kim et al. |
| 2019/0184147 A1 | 6/2019 | Singh et al. |
| 2019/0184148 A1 | 6/2019 | Le et al. |
| 2019/0336741 A1 | 11/2019 | Bayramov et al. |

FOREIGN PATENT DOCUMENTS

| | | |
|---|---|---|
| CA | 2316534 | 3/2001 |
| CA | 2422907 | 4/2002 |
| CA | 2889500 A1 | 5/2014 |
| CN | 102000020 A | 6/2011 |
| CN | 102580232 A | 7/2012 |
| DE | 02319591 | 11/1974 |
| DE | 19518974 | 11/1995 |
| DE | 19624578 | 1/1998 |
| EP | 0156471 | 10/1985 |
| EP | 0240593 | 10/1987 |
| EP | 0301599 | 2/1989 |
| EP | 0305123 A1 | 3/1989 |
| EP | 0312662 | 4/1989 |
| EP | 0400249 | 12/1990 |
| EP | 0407063 | 1/1991 |
| EP | 0796128 | 9/1997 |
| EP | 1086718 A1 | 3/2001 |
| EP | 1086719 A1 | 3/2001 |
| EP | 1174078 | 1/2002 |
| EP | 1377338 A2 | 1/2004 |
| EP | 2283809 A1 | 2/2011 |
| EP | 2399624 A1 | 12/2011 |
| FR | 2535602 | 5/1984 |
| GB | 0783479 | 9/1957 |
| GB | 2221394 | 2/1990 |
| GB | 2277202 | 10/1994 |
| JP | 46-037758 | 12/1971 |
| JP | 60-242042 | 12/1985 |
| JP | 62-213763 | 9/1987 |
| JP | 01-264839 | 10/1989 |
| JP | 02-009755 | 3/1990 |
| JP | 03-151951 | 6/1991 |
| JP | 05-123326 | 5/1993 |
| JP | 05-162076 | 6/1993 |
| JP | 06-238644 | 8/1994 |
| JP | 07-132119 | 5/1995 |
| JP | 08-502215 | 3/1996 |
| JP | 09-051878 | 2/1997 |
| JP | 54-028369 | 3/1997 |
| JP | 09-140687 | 6/1997 |
| JP | 09-211022 | 8/1997 |
| JP | 10-328168 | 12/1998 |
| JP | 11-230707 | 8/1999 |
| JP | 11-509123 | 8/1999 |
| JP | 2000-146777 | 5/2000 |
| JP | 2000-147229 | 5/2000 |
| JP | 2000-164890 | 6/2000 |
| JP | 2000-194142 | 7/2000 |
| JP | 2000-232095 | 8/2000 |
| JP | 2000-232971 | 8/2000 |
| JP | 2000-322780 | 11/2000 |
| JP | 2000-323461 | 11/2000 |
| JP | 2001-004442 | 1/2001 |
| JP | 2001-138300 | 5/2001 |
| JP | 2001-149485 A | 6/2001 |
| JP | 2001-157715 | 6/2001 |
| JP | 2001-341314 | 12/2001 |
| JP | 2002-000728 A | 1/2002 |
| JP | 2002-079499 | 3/2002 |
| JP | 2002-151395 | 5/2002 |
| JP | 2002-239014 | 8/2002 |
| JP | 2002-301698 | 10/2002 |
| JP | 2003-039399 | 2/2003 |
| JP | 2003-048160 | 2/2003 |
| JP | 2003-534881 A | 11/2003 |
| JP | 2004-065775 A | 3/2004 |
| JP | 2006-271781 A | 10/2006 |

(56) References Cited

FOREIGN PATENT DOCUMENTS

| | | |
|---|---|---|
| JP | 2006-341089 A | 12/2006 |
| JP | 2007-130030 A | 5/2007 |
| JP | 2007-190112 A | 8/2007 |
| JP | 2007-536988 A | 12/2007 |
| JP | 2008-006178 A | 1/2008 |
| JP | 2008-074763 A | 4/2008 |
| JP | 2008-194288 A | 8/2008 |
| JP | 2009-082206 A | 4/2009 |
| JP | 2009-082207 A | 4/2009 |
| JP | 2009-201956 A | 9/2009 |
| JP | 2010-233673 A | 10/2010 |
| JP | 2010-233674 A | 10/2010 |
| KR | 20100064669 A | 6/2010 |
| RU | 2414255 C1 | 3/2011 |
| SU | 1641346 | 4/1991 |
| SU | 1667864 | 8/1991 |
| WO | WO 1993/015701 | 8/1993 |
| WO | WO 1993/017754 | 9/1993 |
| WO | WO 1994/023777 | 10/1994 |
| WO | WO 1995/022612 | 8/1995 |
| WO | WO 1995/033612 | 12/1995 |
| WO | WO 1996/000109 | 1/1996 |
| WO | WO 1996/017648 | 6/1996 |
| WO | WO 1996/037155 | 11/1996 |
| WO | WO 1996/037256 | 11/1996 |
| WO | WO 1996/038174 A1 | 12/1996 |
| WO | WO 1997/003629 | 2/1997 |
| WO | WO 1997/003718 | 2/1997 |
| WO | WO 1997/013544 | 4/1997 |
| WO | WO 1997/048440 | 12/1997 |
| WO | WO 1997/048441 | 12/1997 |
| WO | WO 1997/048442 | 12/1997 |
| WO | WO 1998/000193 | 1/1998 |
| WO | WO 1998/028307 | 7/1998 |
| WO | WO 1999/000155 | 1/1999 |
| WO | WO 1999/029298 | 6/1999 |
| WO | WO 1999/029364 | 6/1999 |
| WO | WO 1999/029365 | 6/1999 |
| WO | WO 1999/049874 A1 | 10/1999 |
| WO | WO 1999/061888 | 12/1999 |
| WO | WO 1999/064580 | 12/1999 |
| WO | WO 2000/005166 | 2/2000 |
| WO | WO 2003/026733 A2 | 4/2000 |
| WO | WO 2000/035530 | 6/2000 |
| WO | WO 2000/070406 | 11/2000 |
| WO | WO 2000/074763 A2 | 12/2000 |
| WO | WO 2000/074764 | 12/2000 |
| WO | WO 2000/074765 | 12/2000 |
| WO | WO 2000/074766 | 12/2000 |
| WO | WO 2000/077571 | 12/2000 |
| WO | WO 2001/008242 | 2/2001 |
| WO | WO 2001/036037 | 5/2001 |
| WO | WO 2001/036321 | 5/2001 |
| WO | WO 2001/049362 | 7/2001 |
| WO | WO 2002/002180 | 1/2002 |
| WO | WO 2002/007543 | 1/2002 |
| WO | WO 2002/007813 | 1/2002 |
| WO | WO 2002/017985 | 3/2002 |
| WO | WO 2002/030281 A1 | 4/2002 |
| WO | WO 2002/030301 A1 | 4/2002 |
| WO | WO 2002/032331 | 4/2002 |
| WO | WO 2002/032480 | 4/2002 |
| WO | WO 2002/062202 | 8/2002 |
| WO | WO 2002/064193 A2 | 8/2002 |
| WO | WO 2002/072189 | 9/2002 |
| WO | WO 2002/085446 A2 | 10/2002 |
| WO | WO 2002/091922 | 11/2002 |
| WO | WO 2002/100474 | 12/2002 |
| WO | WO 2003/024290 | 3/2003 |
| WO | WO 2003/024518 | 3/2003 |
| WO | WO 2004/000389 A2 | 12/2003 |
| WO | WO 2004/009172 A1 | 1/2004 |
| WO | WO 2004/020034 A2 | 3/2004 |
| WO | WO 2004/024224 A1 | 3/2004 |
| WO | WO 2004/030649 A2 | 4/2004 |
| WO | WO 2004/060473 A2 | 7/2004 |
| WO | WO 2004/076339 | 9/2004 |
| WO | WO 2004/105729 A2 | 12/2004 |
| WO | WO 2004/110717 | 12/2004 |
| WO | WO 2005/002453 A1 | 1/2005 |
| WO | WO 2005/044333 A2 | 5/2005 |
| WO | WO 2005/046769 A2 | 5/2005 |
| WO | WO 2005/065765 A1 | 7/2005 |
| WO | WO 2005/067889 A1 | 7/2005 |
| WO | WO 2005/082596 A1 | 9/2005 |
| WO | WO 2005/089857 A1 | 9/2005 |
| WO | WO 2005/094526 | 10/2005 |
| WO | WO 2005/099751 A2 | 10/2005 |
| WO | WO 2005/112984 A2 | 12/2005 |
| WO | WO 2006/020842 | 2/2006 |
| WO | WO 2006/055795 | 5/2006 |
| WO | WO 2006/062848 A1 | 6/2006 |
| WO | WO 2006/086742 A2 | 8/2006 |
| WO | WO 2006/101459 A1 | 9/2006 |
| WO | WO 2007/002521 A2 | 1/2007 |
| WO | WO 2007/002522 A1 | 1/2007 |
| WO | WO 2007/002523 | 1/2007 |
| WO | WO 2007/012114 A1 | 2/2007 |
| WO | WO 2007/030477 A2 | 3/2007 |
| WO | WO 2007/061964 A1 | 5/2007 |
| WO | WO 2007/061972 A2 | 5/2007 |
| WO | WO 2007/075806 A2 | 7/2007 |
| WO | WO 2007/081430 A2 | 7/2007 |
| WO | WO 2007/124411 | 11/2007 |
| WO | WO 2008/011625 | 1/2008 |
| WO | WO 2008/015236 A1 | 2/2008 |
| WO | WO 2008/024141 A2 | 2/2008 |
| WO | WO 2008/091602 | 7/2008 |
| WO | WO 2008/093679 A1 | 8/2008 |
| WO | WO 2008/130587 | 10/2008 |
| WO | WO 2008/139648 A1 | 11/2008 |
| WO | WO 2009/012601 A1 | 1/2009 |
| WO | WO 2009/039013 A1 | 3/2009 |
| WO | WO 2009/048607 A1 | 4/2009 |
| WO | WO 2009/054988 A1 | 4/2009 |
| WO | WO 2009/142741 A1 | 11/2009 |
| WO | WO 2010/040271 A1 | 4/2010 |
| WO | WO 2010/124255 A2 | 10/2010 |
| WO | WO 2011/121023 A1 | 10/2011 |
| WO | WO 2011/140240 | 10/2011 |
| WO | WO 2011/140274 | 10/2011 |
| WO | WO 2012/054582 A2 | 4/2012 |
| WO | WO 2012/101639 A2 | 8/2012 |
| WO | WO 2012/122163 A1 | 9/2012 |
| WO | WO 2012/127249 A1 | 9/2012 |
| WO | WO 2012/153266 A2 | 11/2012 |
| WO | WO 2013/172999 A1 | 11/2013 |
| WO | WO 2014/004301 A1 | 1/2014 |
| WO | WO 2014/077244 A1 | 5/2014 |
| WO | WO 2014/100750 A1 | 6/2014 |
| WO | WO 2014/144973 A1 | 9/2014 |
| WO | WO 2014/150069 A1 | 9/2014 |
| WO | WO 2014/150285 A2 | 9/2014 |
| WO | WO 2014/151654 A1 | 9/2014 |
| WO | WO 2014/164314 A1 | 10/2014 |
| WO | WO 2016/033540 A1 | 3/2016 |
| WO | WO 2016/036866 A1 | 3/2016 |
| WO | WO 2016/073908 A1 | 5/2016 |
| WO | WO 2016/149152 A2 | 9/2016 |
| WO | WO 2017/004067 A1 | 1/2017 |
| WO | WO 2017/116076 A1 | 7/2017 |

OTHER PUBLICATIONS

Corbett et al., "Skin vaccination against cervical cancer associated human papillomavirus with a novel micro-projection array in a mouse model", PLOS one, vol. 5, No. 10, pp. 1-9 (2010).

Database WPI / Thomson, Accession No. 2014-V89218, Guo et al., "Soluble microneedle patch useful for transdermal administration of vaccine, comprises water-soluble polymer material as matrix material and soluble microneedle main portion", Application No. CN104027324A, Tech Inst Phys. & Chem. Chinese Acad., 3 pages (2014).

(56) References Cited

OTHER PUBLICATIONS

"Eudragit EPO Readymix—Taste masking and moisture protection have never been easier" Evonik Industries, Evonik Industries AG, Pharma Polymers & Services, Nov. 2014.

"Extend", Merriam-Webster Online Dictionary, 6 pages, Downloaded on Sep. 7, 2010 from <http://www.merriam-webster.com/dictionary/extend>.

"Extend", Macmillan Online Dictionary, 5 pages, Downloaded on Sep. 7, 2010 from <http://www.macmillandictionary.com/dictionary/american/extend>.

Ghosh et al., "Influence of critical parameters of nanosuspension formulation on permeability of a poorly soluble drug through the skin-A case study", AAPS PharmaSciTech, vol. 14, No. 3, pp. 1108-1117 (2013).

Guo et al., "Enhanced transcutaneous immunization via dissolving microneedle array loaded with liposome encapsulated antigen and adjuvant", Int. J. Pharm., vol. 447, No. 1-2, pp. 22-30 (2013).

Gupta, "Aluminum compounds as vaccine adjuvants", Adv. Drug Deliv. Rev., vol. 32, No. 3, pp. 155-172 (1998) Abstract Only.

Gupta and Rost, "Aluminum compounds as vaccine adjuvants", Vaccine adjuvants: Preparation Methods and Research Protocols, O'Hagan, ed., Humana Press, Inc., Totowa, New Jersey, Meth. Mol. Med., vol. 42, No. 4, No. 4, pp. 65-89 (2000).

Henry, et al., "Micromachined microneedles for transdermal delivery of drugs", IEEE Workshop on Micro Electro Mechanical Systems, New York, NY, pp. 494-498, (1998).

Henry, et al., "Microfabricated microneedles: A novel approach to transdermal drug delivery", J. Pharmaceutical Science, vol. 87, No. 8, pp. 922-925, (1998).

"Heparin Pregnancy and Breast Feeding Warnings", Drugs.com, Accessed Oct. 8, 2009, <http://www.drugs.com/pregnancy/heparin.html>.

International Search Report from International Patent Application No. PCT/US2000/015612 dated Sep. 7, 2000.

International Search Report from International Patent Application No. PCT/US2000/015613 dated Sep. 6, 2000.

International Search Report from International Patent Application No. PCT/US2000/015614 dated Sep. 6, 2000.

International Search Report from International Patent Application No. PCT/US2001/031977 dated Apr. 29, 2002.

International Search Report from International Patent Application No. PCT/US2001/031978 dated Apr. 29, 2002.

International Search Report from International Patent Application No. PCT/US2002/014624 dated Sep. 3, 2002.

International Search Report from International Patent Application No. PCT/US2002/029228 dated Apr. 23, 2003.

International Search Report from International Patent Application No. PCT/US2002/029245 dated Dec. 27, 2002.

International Search Report from International Patent Application No. PCT/US2004/005382 dated Nov. 25, 2004.

International Search Report from International Patent Application No. PCT/US2004/017255 dated May 24, 2005.

International Search Report from International Patent Application No. PCT/US2005/009854 dated Jul. 3, 2008.

International Search Report from International Patent Application No. PCT/US2008/000824 dated Jul. 18, 2008.

International Search Report from International Patent Application No. PCT/US2008/004943 dated Jun. 9, 2009, application now published as International Publication No. WO2008/130587 dated Oct. 30, 2008.

International Search Report from International Patent Application No. PCT/US2008/011635 dated Dec. 19, 2008, application now published as International Publication No. WO2009/048607 dated Apr. 16, 2009.

International Search Report from International Patent Application No. PCT/US2010/032299 dated Dec. 10, 2010, application now published as International Publication No. WO2010/124255 dated Oct. 28, 2010.

International Search Report from International Patent Application No. PCT/US2011/035221 dated Jan. 10, 2012, application now published as International Publication No. WO2011/140240 dated Nov. 10, 2011.

International Search Report from International Patent Application No. PCT/US2013/077281 dated Mar. 4, 2013.

International Search Report from International Patent Application No. PCT/US2014/021841 dated Aug. 11, 2014.

International Search Report from International Patent Application No. PCT/US2014/022087 dated May 23, 2014.

International Search Report from International Patent Application No. PCT/US2014/022836 dated May 9, 2015.

International Search Report from International Patent Application No. PCT/US2014/022859 dated May 26, 2014.

International Search Report from International Patent Application No. PCT/US2014/026179 dated Jul. 18, 2014.

International Search Report from International Patent Application No. PCT/US2014/029601 dated Jul. 1, 2014.

International Search Report from International Patent Application No. PCT/US2015/047563 dated Nov. 20, 2015.

International Search Report from International Patent Application No. PCT/US2015/048161 dated Nov. 26, 2015.

International Search Report from International Patent Application No. PCT/US2015/059559 dated Jan. 21, 2016.

Julinova et al., "Initiating biodegradation of polyvinylpyrrolidone in aqueous aerobic environment", Proceedings of ECOpole, vol. 6, No. 1, pp. 121-127 (2012).

Keitel et al., "A randomized clinical trail of acellular pertussis vaccines in healthy adults: Dose-response comparisons of 5 vaccines and implications for booster immunization", J. Infect. Dis., vol. 180, pp. 397-403 (1999).

Kunduru et al., "Biodegradable polymers: Medical Applications", Encyclopedia of Polymer Science and Technology, pp. 1-22 (2016) DOI: 10.1002/0471440264.pst027.pub2.

Kuroda et al., "Particulate adjuvant and innate immunity: past achievements, present findings, and future prospects", Int. Rev. Immunol., vol. 32, No. 2, pp. 209-220 (2013).

Lutrol F 68 NF, BASF Pharma Ingredients, accessed from the internet on Sep. 5, 2016 from http://www2.basf.us/Pharma/pdf/Lutrol_F_68.pdf.

Makaida et al., "Poly lactic-co-glycolic acid (PLGA) as biodegradable controlled drug delivery carrier", Polymers (Basel), vol. 3, No. 3, pp. 1377-1397 (2011).

Matriano, et al., "Macroflux(R) microprojection array patch technology: A new and efficient approach for intracutaneous immunization", Pharm. Res., vol. 19, No. 1, pp. 63-70, (2002).

McAllister, et al., "Micromachined microneedles for transdermal drug delivery", Am. Inst. Chem. Eng., 1998 Annual Meeting, Miami Beach, FL, Nov. 15-20, Drug Delivery II, pp. 1-4.

Mikszta, et al., "Improved genetic immunization via micromechanical disruption of skin-barrier function and targeted epidermal delivery", Nat. Med., vol. 8, No. 4, pp. 415-419, (2002).

Mikszta, et al., "Protective immunization against inhalation anthrax: A comparison of minimally invasive delivery platforms", J. Inf. Dis., vol. 191, No. 2, pp. 278-288, (2005).

Munks et al., "Aluminum adjuvants elicit fibrin-dependent extracellular traps in vivo", Blood, vol. 116, No. 24, pp. 5191-5199 (2010).

Papautsky, et al., "Micromachined Pipette Arrays," MPA, Proceedings—19th international Conference—IEEE/EMBS, Chicago IL, USA, pp. 2281-2284 (1997).

Park et al., "Biodegradable polymer microneedles: Fabrication, mechanics, and transdermal drug delivery", J. Contr. Rel., vol. 104, pp. 51-66 (2005).

Park, et al. "Polymer Microneedles for Controlled-Release Drug Delivery," Pharmaceutical Research, Kluwer Academic Publishers-Plenum Publishers, NE, vol. 23, No. 5, pp. 1008-1019 (2006).

Petrovsky and Aguilar, "Vaccine adjuvants: current state and future trends", Immunol. Cell Biol., vol. 82, No. 5, pp. 488-496 (2004).

Pittman, "Aluminum-containing vaccine associated adverse events: role of route of administration and gender", Vaccine, vol. 20, pp. s48-s50 (2002).

(56) References Cited

OTHER PUBLICATIONS

Polysorbate 80, Material Safety Data Sheet, CAS#: 9005-65-6, Science Lab.com, Inc., 14025 Smith Rd., Houston, Texas 77396, 5 pages, Last updated May 21, 2013.
Prausnitz, et al., "Transdermal transport efficiency during skin electroporation and iontophoresis", J. Contr. Release, vol. 38, pp. 205-217, (1996).
Prausnitz, "Transdermal delivery of macromolecules: Recent advances by modification of skin's barrier properties", ACS Symposium Series No. 675, *Therapeutic Protein And Peptide Formulation And Delivery*, American Chemical Society, Washington DC, Chapter 8, pp. 124-153, (1997).
Prausnitz, "Microneedle-based vaccines", Curr. Top. Microbiol. Immunol., vol. 333, pp. 369-393 (2009).
Rydberg, et al., "Low-molecular-weight heparin preventing and treating DVT", Am. Fam. Physician, vol. 59, No. 6, pp. 1607-1612, (1999).
Sayers et al., "Vaxjo: A Web-Based Vaccine Adjuvant Database and Its Application for Analysis of Vaccine Adjuvants and Their Uses in Vaccine Development", J. Biomed. Biotechnol., vol. 2012, Article ID: 831486, 13 pages, doi:10.1155/2012/831486 (2011).
Sivamani, et al., "Microneedles and transdermal applications", Exp. Opin. Drug Del., vol. 4, No. 1, pp. 19-25, (2007).
Vitiello et al., "Development of a lipopeptide-based therapeutic vaccine to treat chronic HBV infection", J. Clin. Invest., vol. 95, pp. 341-349 (1995).
White et al., "Studies on antibody production. III. The alum granuloma", J. Exp. Med., vol. 102, No. 1, pp. 73-82 (1955).
Wouters, et al., "Microelectrochemical systems for drug delivery", Electrochimica Acta., vol. 42, pp. 3385-3390, (1997).
Xia, et al., "Soft Lithography", Angew. Chem. Int. Ed., vol. 37, pp. 551-575, (1998).
Xia, et al., "Soft Lithography", Annu. Rev. Mater. Sci., vol. 28, pp. 153-184 (1998).
International Search Report from International Patent Application No. PCT/US2019/039028 dated Sep. 13, 2019.
Huh et al., "PLGA-PEG Block Copolymers for Drug Formulations", Drug Dev. Deliv., vol. 3, pp. 1-11 (2003).
Locatelli et al., "Biodegradable PLGA-b-PEG polymeric nanoparticles: synthesis, properties, and nanomedical applications as drug delivery system", J. Nanopart. Res., vol. 14, No. 1316, pp. 1-17 (2012).
Yang et al., "A scalable fabrication process of polymer microneedles", Int. J. Nanomedicine, vol. 7, pp. 1415-1422 (2012).

\* cited by examiner

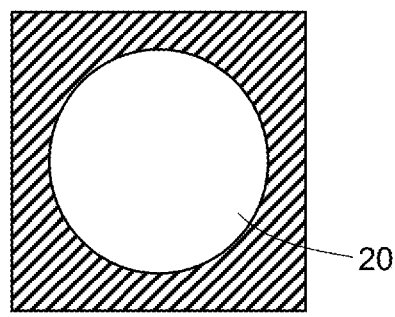 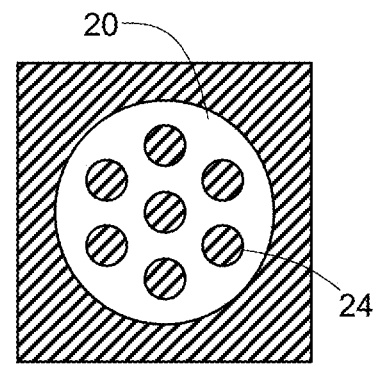
FIG. 18A     FIG. 18B

MICROARRAY FOR DELIVERY OF THERAPEUTIC AGENT AND METHODS OF USE

CROSS-REFERENCE TO RELATED APPLICATIONS

This application claims the benefit of U.S. Non-Provisional application Ser. No. 14/210,402, filed Mar. 13, 2014, now U.S. Pat. No. 10,384,046, issued on Aug. 20, 2019, which claims priority to U.S. Provisional Application No. 61/799,304, filed Mar. 15, 2013, each of which is incorporated herein by reference in their entirety.

TECHNICAL FIELD

The disclosure relates generally to a method and delivery system for sustained and/or controlled, transdermal administration of a therapeutic agent or drug or vaccine using an array of microstructures, and related features thereof.

BACKGROUND

Arrays of microneedles were proposed as a way of administering drugs through the skin in the 1970s, for example in expired U.S. Pat. No. 3,964,482. Microneedle or microstructure arrays can facilitate the passage of drugs through or into human skin and other biological membranes in circumstances where ordinary transdermal administration is inadequate. Microstructure arrays can also be used to sample fluids found in the vicinity of a biological membrane such as interstitial fluid, which is then tested for the presence of biomarkers.

In recent years it has become more feasible to manufacture microstructure arrays in a way that makes their widespread use financially feasible. U.S. Pat. No. 6,451,240 discloses some methods of manufacturing microneedle arrays. If the arrays are sufficiently inexpensive, for example, they may be marketed as disposable devices. A disposable device may be preferable to a reusable one in order to avoid the question of the integrity of the device being compromised by previous use and to avoid the potential need of resterilizing the device after each use and maintaining it in controlled storage.

Despite much initial work on fabricating microneedle arrays in silicon or metals, there are significant advantages to polymeric arrays. U.S. Pat. No. 6,451,240 discloses some methods of manufacturing polymeric microneedle arrays. Arrays made primarily of biodegradable polymers also have some advantages. U.S. Pat. No. 6,945,952 and U.S. Ser. No. Published Patent Applications Nos. 2002/0082543 and 2005/0197308 have some discussion of microneedle arrays made of biodegradable polymers. A detailed description of the fabrication of a microneedle array made of polyglycolic acid is found in Jung-Hwan Park et al., "Biodegradable polymer microneedles: Fabrication, mechanics, and transdermal drug delivery," J. of Controlled Release, 104:51-66 (2005). These biodegradable microstructure arrays (MSA) may consist of a biodegradable tip portion containing a dried active pharmaceutical ingredient (API) and excipients in a biocompatible and water soluble polymer matrix. A backing portion, which connects and supports the tips, may consist of a biocompatible, non-water soluble polymer matrix. Once the MSA penetrates into the subject's skin, the tip portion rapidly dissolves and released the API very quickly, resulting in a fast $T_{max}$.

A layered microstructure array has been described for hPTH delivery (U.S. Patent No. 2011/0276028) comprising a fast dissolving drug-in-tip distal layer and a backing layer formed of an insoluble biodegradable polymer. Administration of these microstructure arrays typically lead to fast dissolution of the distal layer and corresponding fast systemic absorption of the drug.

Many drugs require sustained delivery for a prolonged period of time including hours, days, weeks, etc. One approach for sustained delivery uses microprojection arrays with detachable microprojections such as in U.S. Pat. No. 8,366,677 and U.S. Application No. 61/745,513 filed Dec. 21, 2012, which is incorporated herein by reference.

Therefore, there is a need for a microstructure array that provides for sustained or extended delivery of a therapeutic agent. Furthermore, there is a need to modulate or modify the drug release profile from the microstructure array in order to meet therapeutic requirements for therapeutic agents.

The microstructure arrays are preferably retained on or at the administration site for a period of time for a suitable or desired delivery of the therapeutic agent. One approach for maintaining the array at the delivery site uses a microneedle device that is applied to skin and adhered using a pressure sensitive adhesive surrounding the microneedle array, e.g. U.S. Pat. No. 8,267,889. This approach does not hold the microneedles closely to the skin except at the perimeter of the array where the adhesive contacts the skin and the edge of the array. U.S. Pat. No. 7,184,826 describes the use of microblades for piercing the skin to enhance delivery. To anchor the microblades, they may include a prong or barb extending from the microblades or include a partial adhesive coating. Microneedle arrays including a coating comprising a therapeutic agent coating have also been described, e.g. U.S. Pat. No. 8,057,842.

Thus, there is also a need in the art for microprojection arrays suitable for extended wear that provide better adhesion of the microprojection array and/or better contact of the microprojections and/or arrays.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect of the invention, an array of microstructures is provided comprising an approximately planar base and a plurality of microstructures.

In one aspect, a microstructure apparatus is provided. In an embodiment, the microstructure apparatus comprises (a) an approximately planar substrate having a first surface and a second surface opposed thereto; and (b) a microstructure array comprising a plurality of microstructures contacting the first surface of the substrate and fixedly attached thereto, the microstructures being formed of a polymer matrix comprising (i) a water insoluble, biodegradable polymer, and (ii) at least one therapeutic agent, wherein release of the therapeutic agent from the polymer matrix is sustained for a period of at least about 1-144 hours. In an embodiment, the water insoluble polymer is selected from polylactide, polyglycolide, and co-polymers thereof.

In embodiments, the polymer matrix comprises about 1-50% therapeutic agent. In other embodiments, the polymer matrix comprises about 10-50% therapeutic agent. In further embodiments, the polymer matrix comprises about 20-50% therapeutic agent. In additional embodiments, the polymer matrix comprises about 25-50% therapeutic agent. In yet further embodiments, the polymer matrix comprises about 30-50% therapeutic agent. In other embodiments, the polymer matrix comprises about 45-50% therapeutic agent.

In embodiments, the polymer matrix comprises about 50-99% of the water insoluble, biodegradable polymer. In other embodiments, the polymer matrix comprises about 50-90% of the water insoluble, biodegradable polymer.

In embodiments, an initial release rate of the therapeutic agent from the polymer matrix is between about 0.05-10%/minute. In other embodiments, an initial release rate of the therapeutic agent from the polymer matrix is between about 0.5-10%/minute. In further embodiments, an initial release rate of the therapeutic agent from the polymer matrix is between about 1-10%/minute. In additional embodiments, an initial release rate of the therapeutic agent from the polymer matrix is between about 2-10%/minute.

In embodiments, release of the therapeutic agent from the polymer matrix is sustained for a period of at least about 144 hours. In other embodiments, release of the therapeutic agent from the polymer matrix is sustained for a period of at least about 72 hours. In further embodiments, release of the therapeutic agent from the polymer matrix is sustained for a period of at least about 24 hours. In yet further embodiments, release of the therapeutic agent from the polymer matrix is sustained for a period of at least about 12 hours. In other embodiments, release of the therapeutic agent from the polymer matrix is sustained for a period of at least about 6 hours. In additional embodiments, release of the therapeutic agent from the polymer matrix is sustained for a period of at least about 3 hours. In yet further embodiments, release of the therapeutic agent from the polymer matrix is sustained for a period of at least about 1 hour.

In embodiments, the microstructures are detachable from the substrate.

In embodiments, the therapeutic agent is selected from a drug, a small molecule, a peptide or protein, or a vaccine.

In another embodiment, the microstructure apparatus comprises (a) an approximately planar substrate having a first surface and a second surface opposed thereto; and (b) a microstructure array comprising a plurality of microstructures contacting the first surface of the substrate and fixedly attached thereto, the microstructures being formed of a polymer matrix comprising (i) at least one low molecular weight polymer, (ii) at least one high molecular weight polymer, and (iii) at least one therapeutic agent; wherein an initial release rate of the therapeutic agent from the polymer matrix is between about 0.05-10%/minute; and wherein release of the therapeutic agent from the polymer matrix is sustained for a period of at least about 1-144 hours.

In embodiments, the polymer matrix comprises at least one water insoluble, biodegradable polymer. In further embodiments, at least one of the low molecular weight polymer or the high molecular weight polymer is the water insoluble, biodegradable polymer. In additional embodiments, the water insoluble, biodegradable polymer is selected from polylactide, polyglycolide, and co-polymers thereof.

In embodiments, the initial release rate is between about 0.5-10%/minute. In further embodiments, the initial release rate is between about 1-10%/minute. In additional embodiments, the initial release rate of the therapeutic agent from the polymer matrix is less than about 1-10%/minute.

In embodiments, the low molecular weight polymer has a molecular weight of between about 1-10K Da. In further embodiments, the high molecular weight polymer has a molecular weight of between about 50-300K Da. In additional embodiments, the high molecular weight polymer has a molecular weight of between about 50-70K Da.

In embodiments, the low molecular weight polymer and high molecular weight polymers are present in a ratio of about 1:1-1:10. In further embodiments, the low molecular weight polymer and high molecular weight polymers are present in a ratio of about 1:1. In other embodiments, the low molecular weight polymer and high molecular weight polymers are present in a ratio of about 1:4.

In embodiments, release of the therapeutic agent from the polymer matrix is sustained for a period of at least about 144 hours. In other embodiments, release of the therapeutic agent from the polymer matrix is sustained for a period of at least about 72 hours. In further embodiments, release of the therapeutic agent from the polymer matrix is sustained for a period of at least about 24 hours. In yet further embodiments, release of the therapeutic agent from the polymer matrix is sustained for a period of at least about 12 hours. In other embodiments, release of the therapeutic agent from the polymer matrix is sustained for a period of at least about 6 hours. In additional embodiments, release of the therapeutic agent from the polymer matrix is sustained for a period of at least about 3 hours. In yet further embodiments, release of the therapeutic agent from the polymer matrix is sustained for a period of at least about 1 hour.

In embodiments, the microstructures are detachable from the substrate.

In embodiments, the therapeutic agent is selected from a drug, a small molecule, a peptide or protein, or a vaccine.

In another embodiment a microstructure apparatus comprises (a) an approximately planar substrate having a first surface and a second surface opposed thereto; and (b) a microstructure array comprising a plurality of microstructures contacting the first surface of the substrate and fixedly attached thereto, the microstructures being formed of a polymer matrix comprising (i) at least one biodegradable polymer, (ii) a hydrophilic component, and (iii) at least one therapeutic agent; wherein release of the therapeutic agent from the polymer matrix is sustained for a period of at least about 1-144 hours.

In an embodiment, the biodegradable polymer is a water insoluble, biodegradable polymer.

In an embodiment, release of the therapeutic agent from the polymer matrix is sustained for a period of at least about 4-24 hours. In another embodiment, release of the therapeutic agent from the polymer matrix is sustained for a period of at least about 4-8 hours. In further embodiments, release of the therapeutic agent from the polymer matrix is sustained for a period of at least about 144 hours. In other embodiments, release of the therapeutic agent from the polymer matrix is sustained for a period of at least about 72 hours. In further embodiments, release of the therapeutic agent from the polymer matrix is sustained for a period of at least about 24 hours. In yet further embodiments, release of the therapeutic agent from the polymer matrix is sustained for a period of at least about 12 hours. In other embodiments, release of the therapeutic agent from the polymer matrix is sustained for a period of at least about 6 hours. In additional embodiments, release of the therapeutic agent from the polymer matrix is sustained for a period of at least about 3 hours. In yet further embodiments, release of the therapeutic agent from the polymer matrix is sustained for a period of at least about 1 hour.

In an embodiment, the polymer matrix comprises about 5%-40% of the hydrophilic component. In another embodiment, the polymer matrix comprises about 5%-10% of the hydrophilic component. In a further embodiment, the polymer matrix comprises about 5%-40% of the hydrophilic component. In yet another embodiment, the polymer matrix comprises up to about 40% of the hydrophilic component. In other embodiments, the polymer matrix comprises up to about 20% of the hydrophilic component. In further embodiments, the polymer matrix comprises up to about 10% of the hydrophilic component.

In embodiments, an initial release rate of the therapeutic agent from the polymer matrix is between about 0.05-10%/minute. In other embodiments, an initial release rate of the therapeutic agent from the polymer matrix is between about 0.5-10%/minute. In further embodiments, an initial release rate of the therapeutic agent from the polymer matrix is between about 1-10%/minute. In yet other embodiments, an initial release rate of the therapeutic agent from the polymer matrix is between about 2-10%/minute.

In embodiments the hydrophilic component is PEG-PLGA. In further embodiments, the hydrophobic polymer is selected from PLA, α-hydroxy acids, polycaprolactones, polyanhydrides, and co-polymers thereof. In additional embodiments, the α-hydroxy acid is PLGA.

In embodiments the microstructures are detachable from the substrate.

In embodiments, the therapeutic agent is selected from a drug, a small molecule, a peptide or protein, or a vaccine.

In an embodiment, the microstructure apparatus, comprises (a) an approximately planar substrate having a first surface and a second surface opposed thereto; (b) a microstructure array comprising a plurality of microstructures contacting the first surface of the substrate and fixedly attached thereto, the microstructures being formed of a polymer matrix comprising at least one polymer and at least one therapeutic agent; wherein a ratio of therapeutic agent to polymer in the matrix is low; wherein an initial release rate of the therapeutic agent from the polymer matrix is between about 0.05-10%/minute; wherein release of the therapeutic agent from the polymer matrix is sustained for a period of at least about 1-144 hours.

In embodiments, the ratio of therapeutic agent to polymer is between about 1:2 to 1:25. In further embodiments, the ratio of therapeutic agent to polymer is between about 1:2 to 1:20. In other embodiments, the ratio of therapeutic agent to polymer is between about 1:2 to 1:15. In yet further embodiments, the ratio of therapeutic agent to polymer is between about 1:2 to 1:10. In additional embodiments, the ratio of therapeutic agent to polymer is between about 1:2 to 1:4.

In an embodiment, the polymer matrix comprises at least one water insoluble, biodegradable polymer. In further embodiments, the water insoluble, biodegradable polymer is selected from polylactide, polyglycolide, and co-polymers thereof.

In an embodiment, the initial release rate is between about 0.5%/minute. In further embodiments, the initial release rate of the therapeutic agent from the polymer matrix is less than 10%/minute. In additional embodiments, release of the therapeutic agent from the polymer matrix is sustained for a period of at least about 144 hours. In other embodiments, release of the therapeutic agent from the polymer matrix is sustained for a period of at least about 72 hours. In further embodiments, release of the therapeutic agent from the polymer matrix is sustained for a period of at least about 24 hours. In yet further embodiments, release of the therapeutic agent from the polymer matrix is sustained for a period of at least about 12 hours. In other embodiments, release of the therapeutic agent from the polymer matrix is sustained for a period of at least about 6 hours. In additional embodiments, release of the therapeutic agent from the polymer matrix is sustained for a period of at least about 3 hours. In yet further embodiments, release of the therapeutic agent from the polymer matrix is sustained for a period of at least about 1 hour.

In embodiments the microstructures are detachable from the substrate.

In embodiments, the therapeutic agent is selected from a drug, a small molecule, a peptide or protein, or a vaccine.

In an embodiment a microstructure apparatus, comprises (a) an approximately planar substrate having a first surface and a second surface opposed thereto; and (b) a microstructure array comprising a plurality of microstructures contacting the first surface of the substrate and fixedly attached thereto; wherein at least a portion of the microstructures has a distal portion dimensioned to penetrate a stratum corneum layer of a subject's skin, and a proximal portion that is dimensioned so that it does not penetrate the skin; wherein the distal portion and proximal portion are each formed of a polymer matrix comprising (i) a biodegradable polymer, and (ii) at least one therapeutic agent.

In an embodiment, the apparatus further comprises a backing layer positioned between the proximal portion and the substrate, the backing layer being formed of a polymer matrix comprising (i) a biodegradable polymer, and (ii) the at least one therapeutic agent. In other embodiments, the biodegradable polymer is a water soluble biodegradable polymer. In further embodiments, the biodegradable polymer is a water insoluble biodegradable polymer.

In an embodiment, the therapeutic agent is selected from a drug, a small molecule, a peptide or protein, or a vaccine.

In embodiments, release of the therapeutic agent from the polymer matrix is sustained for a period of at least about 0.1-24 hours. In other embodiments, release of the therapeutic agent from the polymer matrix is sustained for a period of at least about 0.5-10 hours. In further embodiments, release of the therapeutic agent from the polymer matrix is sustained for a period of at least about 0.5-4 hours. In additional embodiments, release of the therapeutic agent from the polymer matrix is sustained for a period of at least about 0.5-4 hours. In yet other embodiments, release of the therapeutic agent from the polymer matrix is sustained for a period of at least about 0.1-1 hours. In other embodiments, the microstructure array is suitable to be worn for at least 1-24 hours.

In another aspect, a method of making a sustained release microstructure apparatus, comprises dissolving or suspending a therapeutic agent in a solvent to form a therapeutic agent solution or suspension;

dissolving at least one water insoluble, biodegradable polymer in a solvent to form a polymer solution;

mixing the therapeutic agent solution or suspension and the polymer solution or suspension to form a polymer matrix solution or suspension;

dispensing the polymer matrix solution or suspension on a mold having an array of microstructure cavities;

filling the microstructure cavities in the mold;

removing excess solution or suspension polymer matrix on the mold surface; and drying the matrix to form a plurality of microstructures;

dispensing a basement or backing layer on the mold surface;

drying the basement or backing layer.

In an embodiment, the method further comprises affixing the basement or backing layer to a substrate. In another embodiment, the method further comprises using a nonwoven or porous film double coated with adhesive to affix the basement or backing layer to a substrate. In a further embodiment, at least one of the solvents is selected from DMSO and acetonitrile. In other embodiments, filling the therapeutic agent is crystalline, and the method further comprises heating the plurality of microstructures to about 110° C. for about 1 hour; and storing the microstructures in a dry cabinet for about 10 days. In embodiments, the heating is performed in a convection oven.

In a further aspect, a method of modulating an initial release rate of a therapeutic agent from a microstructure apparatus comprising a plurality of microstructures formed of a polymer matrix comprising at least one polymer and at least one therapeutic agent, comprises:

(a) wherein the at least one polymer comprises at least one high molecular weight polymer and at least one low molecular weight polymer, adjusting a ratio of the high molecular weight polymers to low molecular weight polymers in the polymer matrix to achieve a desired initial release rate of therapeutic agent from the polymer matrix;

(b) adjusting a ratio of therapeutic agent to polymer in the polymer matrix;

(c) adding at least one hydrophilic component to the polymer matrix; and/or (d) selecting a solvent for preparing the polymer matrix that provides a desired initial release rate.

In an embodiment, (a) comprises increasing the ratio of high molecular weight polymer in the matrix to increase the initial release rate. In another embodiment, (a) comprises increasing the ratio of low molecular weight polymer in the matrix to decrease the initial release rate. In further embodiments, (b) comprises increasing the ratio of therapeutic agent in the matrix to increase the initial release rate. In additional embodiments, (b) comprises decreasing the ratio of low molecular weight polymer in the matrix to decrease the initial release rate.

In embodiments, (c) comprises adding the hydrophilic component as about 10-40% of the matrix to increase the initial release rate.

In embodiments, the hydrophilic component is PEG-PLGA.

In embodiments, the at least one polymer is a water insoluble, biodegradable polymer. In other embodiments, the water insoluble, biodegradable polymer is selected from polylactide, polyglycolide, and co-polymers thereof.

In embodiments, (d) comprises choosing one of DMSO or acetonitrile as the solvent. In other embodiments, (d) comprises choosing DMSO as the solvent to lower the initial release rate. In additional embodiments, (d) comprises choosing acetonitrile as the solvent to increase the initial release rate.

In another aspect, a microstructure apparatus, comprises a substrate having a first surface and a second surface opposed thereto; a plurality of microstructures extending outwardly from the first surface of the substrate; at least a portion of the microstructures comprising at least one therapeutic agent; and an adhesive coating applied to at least one of a) at least a portion of at least some of the plurality of microstructures, or b) at least a portion of the substrate first surface between the microstructures.

In embodiments, at least a portion of the microstructures comprise a biodegradable distal layer and at least one non-biodegradable proximal layer positioned between the distal layer and the first surface of the substrate.

In embodiments, at least a portion of the microstructures are biodegradable.

In embodiments, the therapeutic agent is a drug, a small-molecule agent, a protein or peptide, or a vaccine.

In embodiments, the adhesive coating comprises an adhesive selected from a medical adhesive, a tissue adhesive, or a surgical adhesive. In other embodiments, the medical adhesive is selected from acrylic adhesives, silicone based adhesives, hydrogel adhesives, and synthetic elastomer adhesives. In further embodiments, the tissue adhesive is a cyanoacrylate polymer. In yet further embodiments, the cyanoacrylate polymer is selected from n-butyl-2-cyanoacrylate, and isobutyl cyanoacrylate. In other embodiments, the adhesive coating comprises a fibrin adhesive. In yet other embodiments, the adhesive coating comprises a bioactive film. In additional embodiments, the adhesive coating comprises a pressure sensitive adhesive. In further embodiments, the pressure sensitive adhesive is an acrylic pressure sensitive adhesive. In yet further embodiments, the adhesive coating comprises a rubber-based adhesive.

In embodiments, the adhesive coating is biodegradable. In other embodiments, the adhesive coating is non-continuous. In further embodiments, the adhesive coating includes a plurality of holes. In additional embodiments, the adhesive coating is porous.

In embodiments, the adhesive coating has a reduced adhesion over time.

In embodiments, the adhesive coating is applied to at least about 10-100% of the microstructures in the array. In other embodiments, at least about 10-95% of each coated microstructure has an adhesive coating. In further embodiments, the adhesive coating is applied to a distal portion of the microstructures. In additional embodiments, the adhesive coating is applied to a proximal portion of the microstructures.

In an embodiment, a microstructure apparatus, comprises a substrate having a first surface and a second surface opposed thereto; a plurality of microstructures extending outwardly from the first surface of the substrate; a plurality of openings extending through the substrate and positioned between at least some of the plurality of microstructures; and an adhesive coating applied to at least a portion of the substrate second surface such that the adhesive is capable of contacting a subject's skin through the openings when placed on the skin.

In an embodiment, the adhesive coating is applied to all or substantially all of the substrate second surface. In other embodiments, the adhesive coating is applied the substrate second surface in the region of the openings.

In an embodiment, a backing layer positioned over the adhesive coating.

In an embodiment, at least a portion of the microstructures are at least partially biodegradable.

In an embodiment, the therapeutic agent is a drug, a small-molecule agent, a protein or peptide, or a vaccine.

In embodiments, the adhesive coating comprises an adhesive selected from a medical adhesive, a tissue adhesive, or a surgical adhesive. In other embodiments, the medical adhesive is selected from acrylic adhesives, silicone based adhesives, hydrogel adhesives, and synthetic elastomer adhesives. In further embodiments, the tissue adhesive is a cyanoacrylate polymer. In yet further embodiments, the cyanoacrylate polymer is selected from n-butyl-2-cyanoacrylate, and isobutyl cyanoacrylate. In other embodiments, the adhesive coating comprises a fibrin adhesive. In yet other embodiments, the adhesive coating comprises a bioactive film. In additional embodiments, the adhesive coating comprises a pressure sensitive adhesive. In further embodiments, the pressure sensitive adhesive is an acrylic pressure sensitive adhesive. In yet further embodiments, the adhesive coating comprises a rubber-based adhesive.

In embodiments, the adhesive coating is biodegradable. In other embodiments, the adhesive coating is non-continuous. In further embodiments, the adhesive coating includes a plurality of holes. In additional embodiments, the adhesive coating is porous.

In embodiments, the adhesive coating has a reduced adhesion over time.

In embodiments, the adhesive coating is applied to at least about 10-100% of the microstructures in the array. In other embodiments, at least about 10-95% of each coated microstructure has an adhesive coating. In further embodiments, the adhesive coating is applied to a distal portion of the microstructures. In additional embodiments, the adhesive coating is applied to a proximal portion of the microstructures.

In another aspect, a system comprises the microstructure apparatus of any one of the combined or separate above embodiments and an applicator for applying the microstructure apparatus to a patient's skin.

In another aspect, a method of delivering a therapeutic agent to a subject for an extended period of time, comprises applying a microstructure apparatus of any previous claim to a skin site of the subject; adhering the microstructure apparatus to the skin; delivering the therapeutic agent from the microstructure array to the subject; and removing the microstructure apparatus after at least about 10 minutes.

In an embodiment, the microstructure apparatus is removed after at least about 15 minutes. In another embodiment, the microstructure apparatus is removed after at least about 20 minutes. In a further embodiment, the microstructure apparatus is removed after at least about 30 minutes. In other embodiments, the microstructure apparatus is removed after at least about 45 minutes. In yet other embodiments, the microstructure apparatus is removed after at least about 1 hour. In further embodiments, the microstructure apparatus is removed after at least about 1-24 hours. In yet further embodiments, the microstructure apparatus is removed after at least about 1-5 days.

In an embodiment, at least about 10-100% of a total dose of the therapeutic agent is delivered to the subject. In other embodiments, at least about 50-100% of a total dose of the therapeutic agent is delivered to the subject. In further embodiments, at least about 60-100% of a total dose of the therapeutic agent is delivered to the subject. In additional embodiments, at least about 70-100% of a total dose of the therapeutic agent is delivered to the subject. In other embodiments, at least about 75-100% of a total dose of the therapeutic agent is delivered to the subject. In yet other embodiments, at least about 80-100% of a total dose of the therapeutic agent is delivered to the subject. In further embodiments, at least about 90-100% of a total dose of the therapeutic agent is delivered to the subject. In additional embodiments, at least about 95-100% of a total dose of the therapeutic agent is delivered to the subject.

In an embodiment, the method further comprises:
prior to applying the microstructure apparatus, positioning the microstructure apparatus on a plunger of an applicator;
actuating the applicator to release the plunger;
impacting the skin with the microstructure apparatus;
removing the applicator with the microstructure apparatus remaining on the skin site for an extended period of time.

In an embodiment, the method further comprises pressing the microstructure apparatus against the skin site to push the adhesive through the openings and into contact with the skin site.

Additional embodiments of the present microstructures, arrays, methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF DRAWINGS

FIG. 6A shows crystallization of Clonidine. FIG. 6B shows the film after heat treatment at 110° C. for one hour and storage in a dry cabinet for 10 days. FIG. 6C shows a microscope glass control.

FIG. 10A depicts a microstructure having a pyramidal tip with a funnel shaped distal portion. FIG. 10B depicts a microstructure having a conical tip, a cylindrical shank and a conical funnel distal portion.

FIG. 12B shows use of an exemplary microstructure array having drug loaded in the entire microstructure. FIG. 12A shows use of an exemplary microstructure array having drug loaded only in the penetrating portion of the microstructures. FIG. 12C shows use of an exemplary microstructure having drug loaded in the whole microstructure and a portion of the backing layer or substrate.

FIGS. 18A-18B are side view illustrations of embodiments of microstructure array geometry.

Figure 1A:
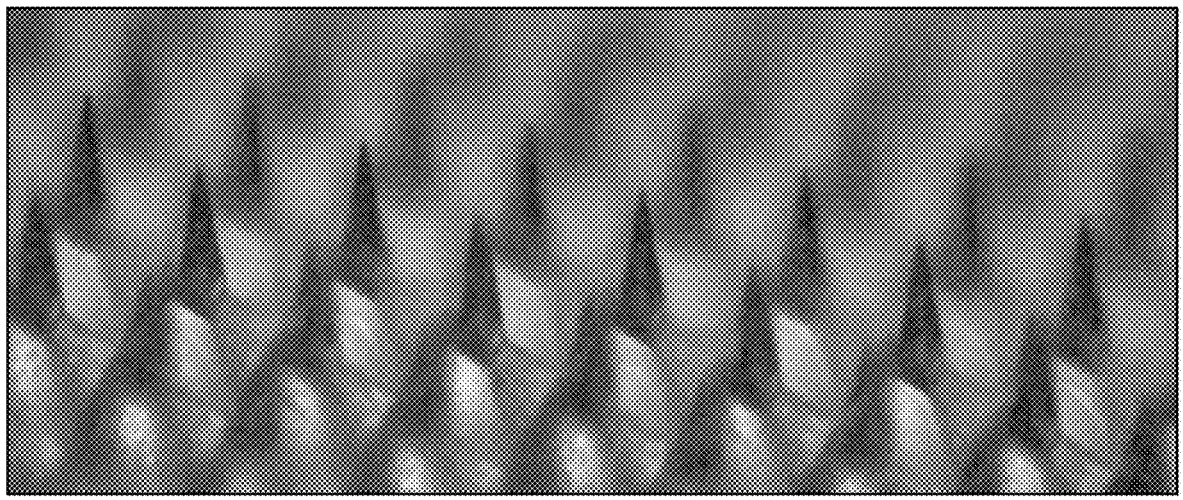
FIGS. 1A-1B are microscopic images of one exemplary sustained release microstructure array with 35% Clonidine in a PLGA polymer matrix. The image in FIG. 1A is taken from the sharp side of the microstructures. The image in FIG. 1B is taken from the wide side of the microstructures.

It will be appreciated that the thicknesses and shapes for the various microstructures have been exaggerated in the drawings to facilitate understanding of the device. The drawings are not necessarily "to scale."

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

I. Definitions

As used in this specification, the singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

In describing and claiming the present invention, the following terminology will be used in accordance with the definitions described below.

"Biodegradable" refers to natural or synthetic materials that degrade enzymatically, non-enzymatically or both to produce biocompatible and/or toxicologically safe by-products which may be eliminated by normal metabolic pathways.

"Hydrophobic polymer" as used herein refers to polymers that are insoluble or poorly soluble in aqueous solvents. "Hydrophilic polymer" as used herein refers to polymers that are soluble or substantially soluble in aqueous solvents.

The terms "microprotrusion", "microprojection", "microstructure" or "microneedle" are used interchangeably herein to refer to elements adapted to penetrate or pierce at least a portion of the stratum corneum or other biological membranes. For example, illustrative microstructures may include, in addition to those provided herein, microblades as described in U.S. Pat. No. 6,219,574, edged microneedles as described in U.S. Pat. No. 6,652,478, and microprotrusions as described in U.S. Patent Publication No. U.S. 2008/0269685.

"Optional" or "optionally" means that the subsequently described circumstance may or may not occur, so that the description includes instances where the circumstance occurs and instances where it does not.

"Substantially" or "essentially" means nearly totally or completely, for instance, 90-95% or greater of some given quantity.

"Transdermal" refers to the delivery of an agent into and/or through the skin for local and/or systemic therapy. The same inventive principles apply to administration through other biological membranes such as those which line the interior of the mouth, gastro-intestinal tract, blood-brain barrier, or other body tissues or organs or biological membranes which are exposed or accessible during surgery or during procedures such as laparoscopy or endoscopy.

A material that is "water-soluble" may be defined as soluble or substantially soluble in aqueous solvents, such that the material dissolves into, within or below the skin or other membrane which is substantially aqueous in nature.

II. Microstructure Arrays

A. Microstructure Array Composition

General features of microstructure arrays suitable for use in the instant arrays and methods are described in detail in U.S. Patent Publication No. 2008/0269685, U.S. Patent Publication No. 2011/0006458, and U.S. Patent Publication No. 2011/0276028, the entire contents of which are explicitly incorporated herein by reference.

In one aspect, the microstructure array is a sustained release array that provides sustained release of at least one therapeutic agent from the microstructures. The array typically includes an approximately planar substrate, base or backing having a first surface and a second surface opposed thereto. At least one, but preferably a plurality of microstructures contact the first surface and are fixedly attached thereto. The microstructures typically project from the substrate at an angle. The microstructures may be attached to the substrate by any suitable means known in the art. In one, non-limiting embodiment, the microstructures are attached to the substrate using an adhesive. Suitable adhesives include, but are not limited to, acrylic adhesives, acrylate adhesives, pressure sensitive adhesives, double-sided adhesive tape, double sided adhesive coated nonwoven or porous film, and UV curable adhesives. One exemplary double-sided tape is the #1513 double-coated medical tape available from 3M. One exemplary, but non-limiting, UV curable adhesive is the 1187-M UV light-curable adhesive available from Dymax. It will be appreciated that any medical device adhesive known in the art would be suitable. The substrate, base or backing may be rigid, semi-rigid or flexible as needed based on the use of the microstructure array.

In another embodiment, the microstructure arrays include a proximal, backing or basement layer. In further embodiments, the microstructure arrays include a proximal backing or basement layer positioned between the microstructures and the substrate. It will be appreciated that the backing layer may also function as the substrate, base or backing such that the backing layer extends between the microstructures. In embodiments, the proximal or backing layer or portion may be designed not to penetrate the skin.

The substrate and/or backing layer are typically formed of one or more biocompatible and/or non-biodegradable materials. The substrate and/or backing layer may be formed of any suitable material that provides the necessary support for the microstructures. Preferably, the substrate and/or backing layer is formed of a synthetic or natural material that is biocompatible at least on the surface that may contact the patient's skin. Suitable materials include, but are not limited to, metals, silicon and/or polymers. In an embodiment, the substrate and/or backing layer comprises one or more water insoluble polymers. Suitable polymers include, but are not limited to, polyethylene terephthalate and polyether ether ketone, polycarbonate, polyethylene, or other film forming polymers amphiphilic polyurethanes, polyether polyurethane (PEU), polyetheretherketone (PEEK), and polyamide-imide (PAI). Further suitable polymers are described in U.S. Pat. No. 7,785,301, which is incorporated herein in its entirety. In another embodiment, the backing layer and/or substrate is formed from an adhesive. One suitable adhesive is the Dymax® 1187-M UV medical device adhesive. It will be appreciated that any biocompatible adhesive is suitable for use with, in and/or as the backing layer and/or substrate. The backing layer and/or substrate may also be a nonwoven or porous film double coated with pressure sensitive adhesive. The substrate and/or backing layer may be rigid, substantially rigid or may be at least partially flexible to conform to the surface of the patient's skin. In any case, the substrate and/or backing layer should be sufficiently strong and/or rigid to assist in or allow for the microstructures to at least partially penetrate the patient's skin. The substrate is typically substantially planar, but may be contoured.

In reference to the microstructures themselves, in general, at least a portion of the microstructures have a height above the base or structure that is sufficient to pierce at least a portion of the epidermis. In embodiments, the microstructures have a height sufficient to pierce all or a portion of the stratum corneum. Typically, the microstructures have a height that penetrates into the epidermis where the density of nerve receptors is low. In embodiments, at least a portion of the microstructures have a height of at least about 50 μm or at least about 100 μm, or at least about 150 μm, or at least about 200 μm, or at least about 250 μm, or at least about 300 μm. In general, the microstructures have a height of no more than about 1 mm, no more than about 500 μm, no more than about 300 μm, no more than about 200 μm, or no more than about 150 μm. In embodiments, the microstructures have a height of between about 50 μm-1 mm. It will be appreciated that the microstructures within an array may have different heights. The microstructures may have an aspect ratio (height to diameter at base) of at least 10:1, preferably at least about 5:1, more preferably at least about 3:1, or at least about 2:1, or at least about 1:1. As the depth of the epidermis and/or dermis layers may be different depending on the area of the body, it will be appreciated that the height of the microstructures may be adjusted depending on the administration site.

The microprojections may be spaced about 0-500 μm apart. In specific, but not limiting embodiments, the microprojections are spaced about 0 μm, about 50 μm, about 100 μm, about 150 μm, about 200 μm, about 250 μm, about 300 μm, about 350 μm, about 400 μm, about 450 μm, or about 500 μm apart. The space between the microprojections may be measured from the base of the microprojections (base to base) or from the tip (tip to tip).

One illustrative shape for the microstructures is a cone with a polygonal bottom, for example, being hexagonal or rhombus-shaped. Additional microstructure shapes include those provided, for example, in U.S. Patent Publication No. 2004/0087992 with exemplary suitable shapes shown in FIGS. 10A-10B. In embodiments, at least a portion of the microstructure shape may be substantially cylindrical, cone-shaped, funnel-shaped, or pyramidal. In further embodiments, at least a portion of the microstructures has an asymmetrical cross-dimensional shape. Suitable asymmetric shapes include, but are not limited to, rectangular, square, oval, elliptical, circular, rhombus, triangular, polygonal, star-shaped, etc. In some embodiments, the distal layer has a cross-dimension in one direction that is smaller than the cross-dimension in the other direction. Exemplary cross-dimensional shapes with this configuration include, but are not limited to, rectangular, rhombus shaped, ellipse, and oval. The microstructures typically, but not always, have a sharp, pointed or conical distal end to ease and/or facilitate penetration.

Figure 10A:
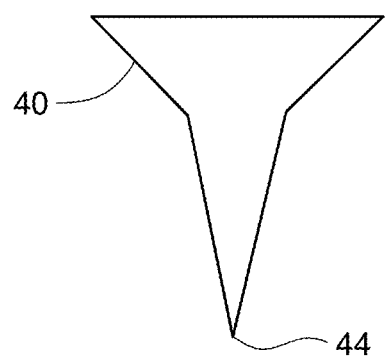
FIGS. 10A-10B are illustrations of exemplary shapes for microstructures including a funnel shape.
Figure 10B:
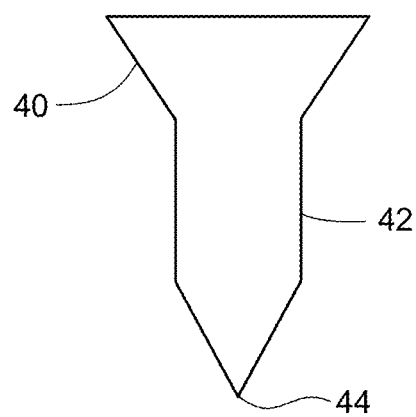

In the embodiments shown in FIGS. 10A-10B, at least a portion of the microstructure has a funnel shape 40. In embodiments, the microstructure has a funnel portion 40, a cylindrical portion 42, and a tip 44. In FIG. 10A, the diameter of the microstructure is growing faster than linear fashion with respect to the distance from the distal end. Where microstructures are thicker towards the base, a portion of the microstructure adjacent to the base, which may be referred to herein as a "proximal portion" "backing portion", "basement", "foundation", or as an "upper portion" may be designed not to penetrate the skin.

The proximal funnel shape allows for relatively larger volumes to be dispensed in the microstructure mold for a given total length of the microstructure. The proximal funnel shape provides a larger volume (to fill) without requiring a proportional increase in microstructure height, which results in a longer drug containing portion in the microstructure. Thus, the proximal funnel shape allows for a larger solid volume for the distal portion of the microstructure with a single fill of the mold. Other shapes may require several fill and dry cycles to achieve the same amount of solid distal portion as one fill and dry cycle for the funnel shaped microstructures.

While the array itself may possess any of a number of shapes, the array is generally sized to possess a diameter of from about 5 millimeters to about 25 millimeters, or from about 7 to about 20 millimeters, or from about 8 to about 16 millimeters. Exemplary diameters include 5, 6, 7, 8, 9, 10, 11, 12, 13, 14, 15, 16, 17, 18, 19, 20, 21, 22, 23, 24, and 25 millimeters.

At least a portion of the microstructures are typically formed of a polymer matrix comprising at least one therapeutic agent, active agent, or drug (collectively "agent" or "therapeutic agent" hereafter). The agent to be administered can be one or more of any of therapeutic agents, active agents or drugs known in the art, and include the broad classes of compounds such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof. In some embodiments, the agent is a protein or a peptide. In other embodiments, the agent is a vaccine.

Examples of peptides and proteins which may be used with the microstructure arrays include, but are not limited to, parathyroid hormone (PTH), oxytocin, vasopressin, adrenocorticotropic hormone (ACTH), epidermal growth factor (EGF), prolactin, luteinizing hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumor necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factors VII and IX, lysozyme chloride, renin, bradykinin, tyrocidin, gramicidines, growth hormones, melanocyte stimulating hormone, thyroid hormone releasing hormone, thyroid stimulating hormone, pancreozymin, cholecystokinin, human placental lactogen, human chorionic gonadotropin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically active fragments thereof. Peptidyl drugs also include synthetic analogs of LHRH, e.g., buserelin, deslorelin, fertirelin, goserelin, histrelin, leuprolide (leuprorelin), lutrelin, nafarelin, tryptorelin, and pharmacologically active salts thereof. Administration of oligonucleotides is also contemplated, and includes DNA and RNA, other naturally occurring oligonucleotides, unnatural oligonucleotides, and any combinations and/or fragments thereof. Therapeutic antibodies include Orthoclone OKT3 (muromonab CD3), ReoPro (abciximab), Rituxan (rituximab), Zenapax (daclizumab), Remicade (infliximab), Simulect (basiliximab), Synagis (palivizumab), Herceptin (trastuzumab), Mylotarg (gemtuzumab ozogamicin), CroFab, DigiFab, Campath (alemtuzumab), and Zevalin (ibritumomab tiuxetan).

In other embodiments, at least a portion of the distal layer comprises an agent suitable for use as a prophylactic and/or therapeutic vaccine. Examples of vaccines include, but are not limited to, vaccines to varicella, diphtheria, pertussis, hepatitis (A and/or B), Human Papillomavirus, influenza, measles, mumps, rubella, whooping cough, polio, tetanus, meningitis, shingles, etc.

In another embodiment, at least a portion of the distal layer comprises an agent suitable for veterinary uses. Such uses include, but are not limited to, therapeutic and diagnostic veterinary uses.

In embodiments, the polymer matrix comprises at least about 10-50% of the therapeutic agent. In other embodiments, the polymer matrix comprises at least about 45-50%, about 30-50%, about 25-50%, about 20-50%, or about 15-50% of the therapeutic agent. In a further embodiment, the polymer matrix comprises at least about 10-50% of at least one structural polymer. In specific, but not limiting embodiments, the polymer matrix comprises at least about 45-50%, about 30-50%, about 25-50%, about 20-50%, or about 15-50% of at least one structural polymer. In embodiments, % is weight %.

In one aspect, the microstructure arrays described herein provide sustained release or sustained delivery of the therapeutic agent. In this embodiment, the microstructure array typically comprises an approximately planar substrate and a plurality of microstructures contacting and being fixedly attached to a surface of the substrate. At least a portion of the microstructures are formed of a polymer matrix comprising (i) at least one water insoluble, biodegradable polymer, and (ii) at least one therapeutic agent. In one embodiment, the microstructures include a distal layer formed of the polymer matrix. The polymer matrix distal layer may be referred to as a drug-in-tip (DIT) distal layer. In another embodiment, the microstructures include a distal layer formed of the polymer matrix and a proximal or backing layer formed of a non-biodegradable polymer. At least a portion of the proximal or backing layer may be configured so that it does not penetrate the subject's skin.

Suitable water insoluble, biodegradable polymers are known in the art. Exemplary water insoluble, biodegradable polymers include, but are not limited to, polylactide, α-hydroxy acids such as poly(lactic-co-glycolic acid) (PLGA), polyanhydrides, an aliphatic polyester, a copolyester with aliphatic and aromatic blocks, a polyester amide, a polyester urethane, a polyethylene oxide polymer, a polyglycol, and co-polymers thereof. For co-polymers, it will further be appreciated that the ratio of the monomers may be adjusted to achieve a desired hydrophobicity and/or degradation rate. For example, lactide rich PLGA copolymers are more hydrophobic than glycolide rich PLGA copolymers. The ratio of hydrophobic:hydrophilic monomers in the polymer may be selected to achieve the desired degradation rate. In one non-limiting embodiment, the water insoluble, biodegradable polymer is PLGA. In another embodiment, the PLGA has a lactic acid/glycolic acid ratio of 75/25.

Microneedle arrays are typically applied for a short period of time, which is sufficient to allow the water soluble polymer matrix DIT to degrade and release the drug, typically about 5-15 minutes. However, many drugs require a sustained deliver or slow delivery for proper efficacy. Further, many conditions require continuous or sustained levels of a therapeutic agent for proper treatment. Slow release of a drug from a microprojection array may provide a suitable dose for therapy over a period of time which avoids toxicity and/or side effects. In embodiments, the microarrays described herein provide for sustained release or sustained delivery of the therapeutic agent from the polymer matrix. In embodiments sustained release provides for a slow and/or constant release of the drug over an extended period of time. Sustained release systems may be used to maintain constant drug levels over a period of time. In some embodiments, the microstructure arrays provide for release of the active agent from the polymer matrix for at least 10-15 minutes. In other embodiments, the arrays provide for release of the active agent for at least about 15 minutes, at least about 30 minutes, at least about 1 hour, at least about 2 hours, at least about 4 hours, at least about 6 hours, at least about 8 hours, at least about 10 hours, at least about 12 hours, at least about 18 hours, at least about 24 hours, at least about 36 hours, at least about 48 hours, or longer. In one embodiment, the arrays provide for release of the active agent for a period of at least about 15 minutes to about 60 hours. In further embodiments, the arrays provide for release of the active agent for a period of at least about 30 minutes to about 24 hours, about 1-48 hours, about 1-36 hours, about 1-24 hours, about 1-18 hours, about 1-12 hours, about 1-10 hours, about 1-8 hours, about 1-6 hours, about 1-4 hours, about 1-2 hours, about 2-24 hours, about 2-18 hours, about 2-12 hours, about 2-10 hours, about 2-8 hours, about 2-6 hours, about 2-4 hours, about 4-24 hours, about 4-18 hours, about 4-12 hours, about 4-10 hours, about 4-8 hours, about 4-6 hours, about 6-24 hours, about 6-18 hours, about 6-12 hours, about 6-10 hours, about 6-8 hours, about 8-24 hours, about 8-18 hours, about 8-12 hours, about 8-10 hours, about 10-24 hours, about 10-18 hours, about 10-12 hours, about 12-24 hours, about 12-18 hours, about 18-24 hours, about 1-144 hours, about 1-72 hours, about 1-60, or longer. In further embodiments, the arrays provide for release of the active agent for a period of at least about 1-60 hours or longer. In specific, but not limiting embodiments, the therapeutic agent is released from the microstructure array for a period of at least about 144 hours, about 72 hours, about 24 hours, about 12 hours, about 6 hours, about 3 hours, about 2 hours, about 1 hour, or about 0.5 hours.

Figure 1B:
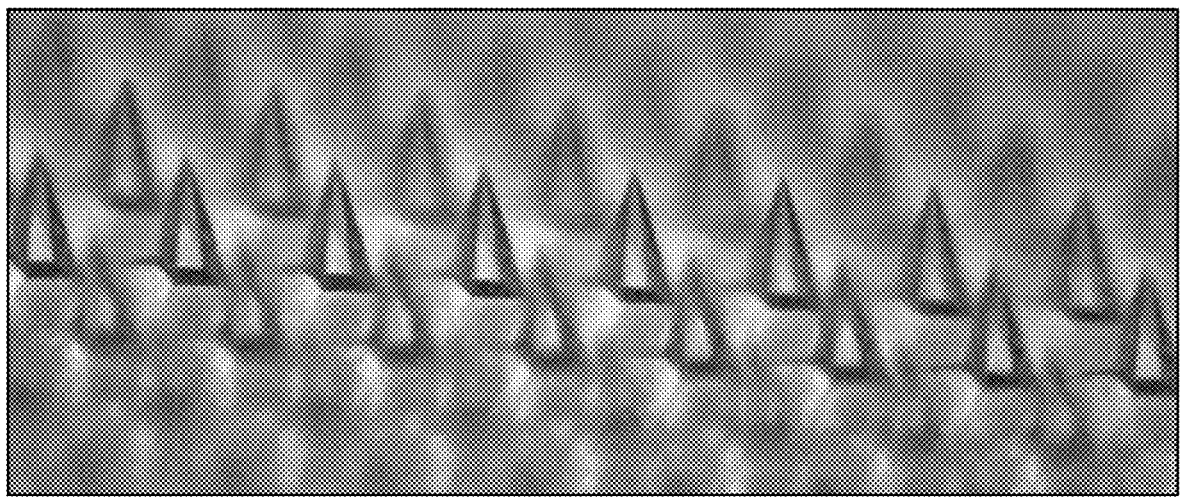
Figure 2:
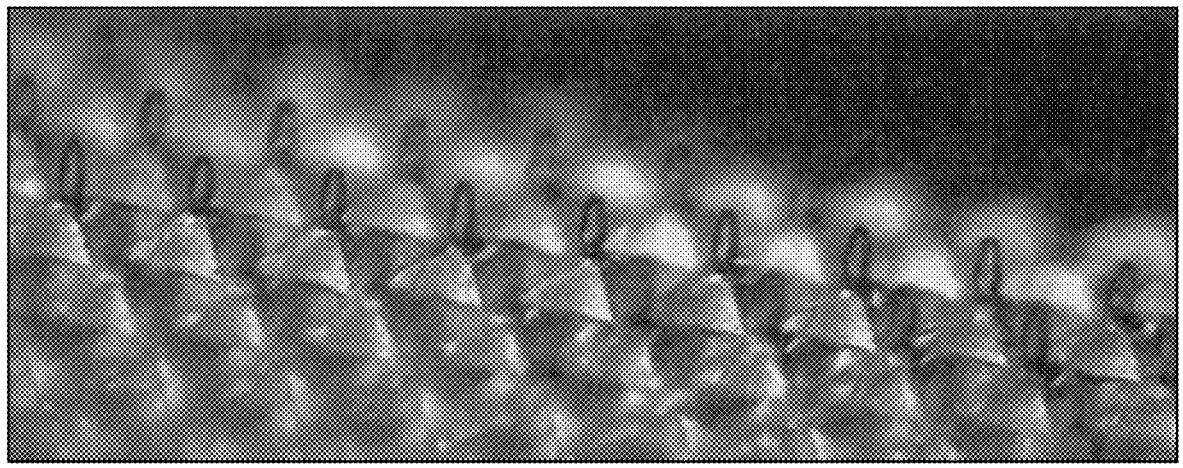
FIG. 2 is a microscopic image of a residual basement layer formed of a UV curable adhesive after ACN extraction. The image is taken from the sharp side of the microstructures.

As described in Example 1, exemplary microstructure arrays comprising a drug-in-tip (DIT) distal layer comprising 35% Clonidine in PLGA and a UV adhesive backing layer on a PET substrate were formed and are shown in FIGS. 1A-1B. The DIT portions were highly degradable. As described in Example 2, a microstructure array comprising a 35% Clonidine in PLGA DIT was placed in acetonitrile (ACN) solvent to extract the DIT portion. As seen in FIG. 2, the DIT portion dissolved in the solvent with the UV adhesive layer remaining.

Figure 5:
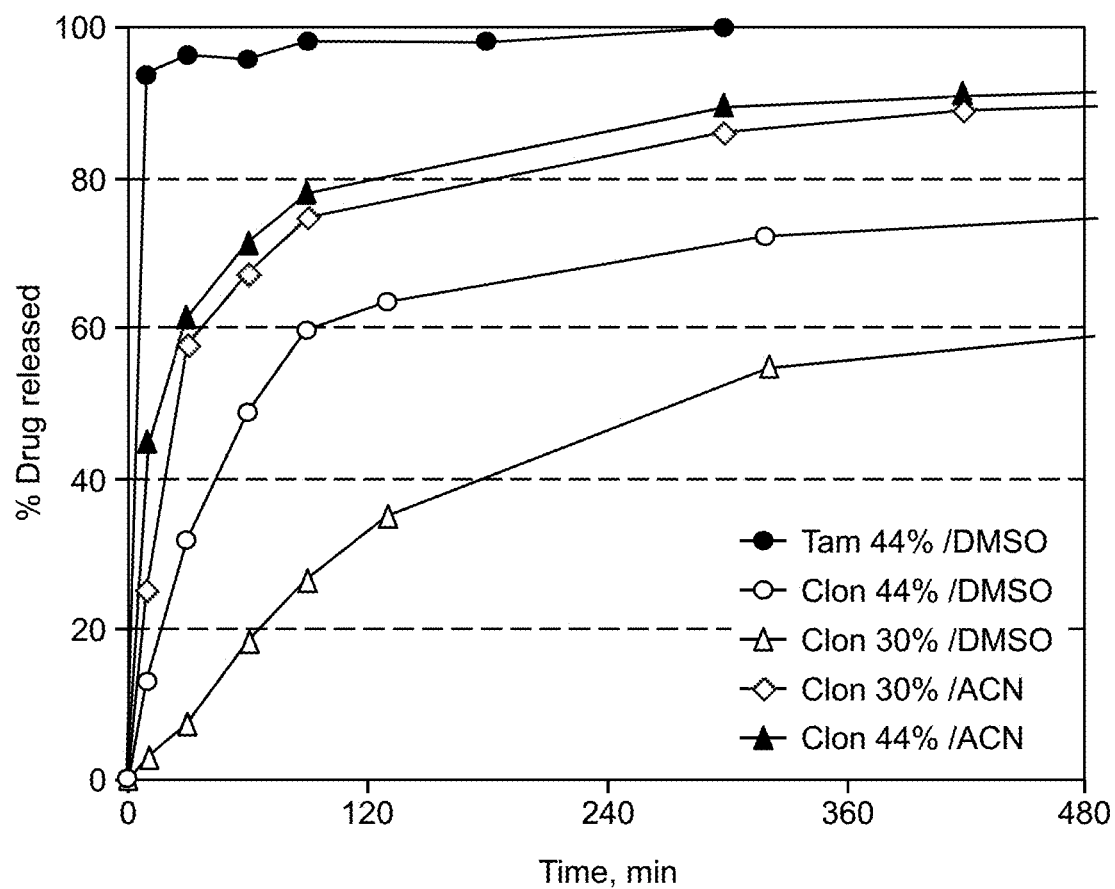
FIG. 5 is a graph of % drug released from microstructures formed using DMSO or ACN as the solvent over time in minutes. The polymer matrix comprised Clonidine or Tamsulosin at 30% or 44% drug load.

It has been found that type of solvent used to fabricate PLGA DIT has a significant effect on drug release rate. Without being limited as to theory, it is believed that the choice of solvent changes the morphology (crystalline/amorphous) of the drug, which affects the drug's release rate. As described in Example 3, the effect of solvent choice on drug release rate was investigated by immersing microstructure arrays in a phosphate buffer, taking samples at specific time points and analyzing drug content in the sample by HPLC. FIG. 5 is a graph of the % Clonidine released from the microstructure array over time in minutes. Arrays were prepared using DMSO or ACN as the solvent for 44% Tamsulosin prepared with DMSO (●), 44% Clonidine prepared with DMSO (○), 44% Clonidine prepared with ACN (▲), 30% Clonidine prepared with DMSO (∆), and 30% Clonidine prepared with ACN (◊). As it is shown in FIG. 5 Clonidine loaded MSA prepared from DMSO showed significantly lower drug release rate as compared to Clonidine loaded MSA prepared from ACN. For the MSA with a 44% Clonidine load, the MSA prepared with ACN had about a 15-20% increase in the percentage of drug released after 120 minutes and after 360 minutes. For the MSA with a 30% Clonidine load, the MSA prepared with ACN had about 40-45% increase in the percentage of drug released after 120 minutes and about 30-35% increase after 360 minutes. On the other hand, Tamsulosin formulated with PLGA with DMSO as solvent had almost immediate drug release, probably due to the enhanced plasticization of the drug to the polymer by the DMSO solvent.

The physical state of the drug (e.g. crystalline or amorphous solid solution) in PLGA DIT may have significant impact on drug release properties of the matrix. Heat treatment may be used to change physical state of drug in PLGA DIT and thus drug release profile. Heat treatment of dry PLGA DIT containing crystalline drug may lead to irreversible dissolution of crystals in solid PLGA if the samples are subjected to heating above drug melting point. To test this hypothesis PLGA films loaded with 35% Clonidine were prepared by casting from ACN (PLGA concentration in liquid casting solution was 25%) on a microscope glass. After casting and drying at 70° C. (below Clonidine melting point) Clonidine crystals had been formed in the film as it is shown in the FIG. 6A. A spot in the obtained films was located and marked to trace changes in the film after heat treatment. Films were heat treated in convection oven at 110° C. for 1 hour and then stored in dry cabinet for 10 days. As it is seen from FIG. 6B no Clonidine crystallization was observed after heat treatment and storage. The small bright particles observed in FIG. 6B correspond to microscope glass background as it is evidenced by the control photograph of microscope glass in FIG. 6C.

Figure 9:
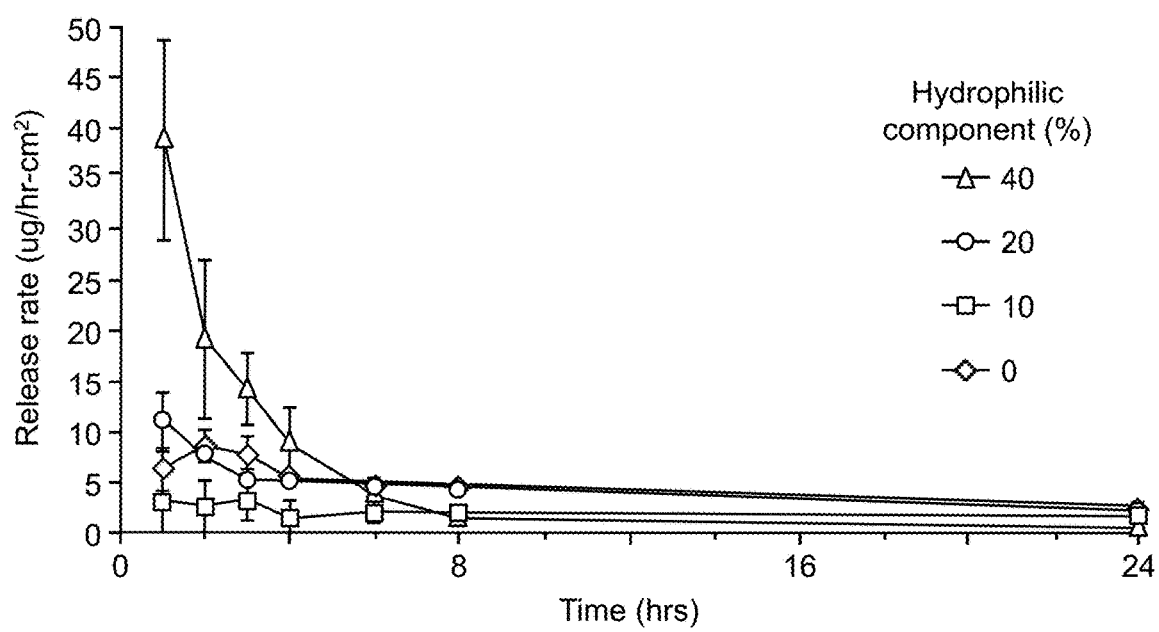
FIG. 9 is a graph of drug release rate in μg/hr/cm$^2$ for exemplary microstructure arrays prepared with a 0%, 10%, 20%, or 40% of a hydrophilic component over time in hours.

Addition of hydrophilic components into a hydrophobic polymer matrix can significantly change the drug release profile. In one non-limiting embodiment, the hydrophilic component is PEG-PLGA. As described in Example 5, microstructure arrays comprising Clonidine in a PLGA polymer matrix were prepared including 0%, 10%, 20%, or 40% of a PEG-PLGA hydrophilic component. The release rate of the arrays was determined by immersing the array in a phosphate buffer and taking samples at specific time points and analyzing drug content in the sample by HPLC. FIG. 9 is a graph of the release rate of the drug in µg/hr/cm$^2$ for microstructure arrays comprising 0% (◊), 10% (□), 20% (○), or 40% (∆) of the hydrophilic component over time in hours. FIG. 9 demonstrates that the addition of hydrophilic PEG-PLGA into a PLGA matrix, the release of a protein from the MSA increases with the increase of hydrophilic component in the matrix. Addition of 10% or 20% of the hydrophilic component reduced or eliminated the initial burst of the drug. Addition of 40% of the hydrophilic component resulted in an initial burst which tapered off for about 6 hours. Addition of 10% hydrophilic component resulted in a flat release rate with no burst and sustained release for at least 24 hours. Addition of 20% of the hydrophilic component resulted in a low initial burst with a release rate of about 10-15 µg/hr/cm² and then a flat release rate for at least 24 hours.

In embodiments, the polymer matrix comprises at least about 5-40% of the hydrophilic component. In further embodiments, the polymer matrix comprises at least about 5-35%, about 5-30%, about 5-25%, about 5-20%, about 5-15%, about 5-10%, about 10-35%, about 10-30%, about 10-25%, about 10-20%, about 10-15%, about 15-35%, about 15-30%, about 15-25%, about 15-20%, about 20-30%, about 20-25%, about 25-35%, or about 25-30% of the hydrophilic component. In embodiments, % is weight %.

In another embodiment, the drug release rate profile may be modulated in order to meet certain therapeutic requirements for the drug. It will be appreciated that modulating the drug release rate profile may be beneficial for the sustained release microarrays described herein as well as with known microarrays such as those described in U.S. Publication No. U.S. 2008/0269685 and U.S. 2011/0276028, among others.

Achieving long term zero-order release of drugs from a biodegradable polymer matrix has been difficult to achieve. Release of drugs from the polymer matrix is often characterized by a rapid initial release ("burst") in the first few hours followed by a slow, diffusion-controlled release thereafter. However, many drugs, including many peptide therapeutics, can be toxic when administered with a burst initial release rate. Further, reducing or preventing the initial burst and/or controlling the release of the drug at a constant rate allows the blood concentration of the drug to be maintained for a long period of time. In one embodiment, the release rate is modulated to provide a flat or substantially flat release for at least a period of time. In another embodiment, the release rate is flat or substantially flat for at least a period of time with no or substantially no initial burst. In a further embodiment, the release rate is less than 3 $C_{max}-C_{min}$.

In embodiments, modulating the release rate comprises modulating the release rate of the drug to between about 0.05-10%/minute. It will be appreciated that modulating the release rate may refer to the overall release rate and/or to an initial release rate. In other words, one or both of the overall release rate or the initial release rate may be modulated. In other embodiments, the release rate is modulated to between about 0.5-10%/minute, about 1-10%/minute, about 2-10%/minute, about 5-10%/minute, about 0.5-20%/minute, about 1-20%/minute, about 2-20%/minute, or about 5-20%/minute. In specific, but not limiting embodiments, the release rate is modulated to about 0.05%/minute, about 0.5%/minute, about 1%/minute, about 2%/minute, about 3%/minute, about 4%/minute, about 5%/minute, about 6%/minute, about 7%/minute, about 8%/minute, about 9%/minute, about 10%/minute, or about 20%/minute. In embodiments, % is weight %.

In embodiments, modulating the release rate comprises modulating the release rate of the drug to between about 0.25-40 µg/hr/cm². It will be appreciated that modulating the release rate may refer to the overall release rate and/or to an initial release rate. In other words, one or both of the overall release rate or the initial release rate may be modulated. In other embodiments, the release rate is modulated to between about 0.5-30 µg/hr/cm², about 2-40 µg/hr/cm², about 2-30 µg/hr/cm², about 2-25 µg/hr/cm², about 2-20 µg/hr/cm², about 2-15 µg/hr/cm², about 2-10 µg/hr/cm², about 2-8 µg/hr/cm², about 2-6 µg/hr/cm², about 2-5 µg/hr/cm², about 2-4 µg/hr/cm², about 2-3 µg/hr/cm², about 5-30 µg/hr/cm², about 5-25 µg/hr/cm², about 5-20 µg/hr/cm², about 5-15 µg/hr/cm², about 5-10 µg/hr/cm², about 5-8 µg/hr/cm², about 5-6 µg/hr/cm², about 10-40 µg/hr/cm², about 10-30 µg/hr/cm², about 10-25 µg/hr/cm², about 10-20 µg/hr/cm², about 10-15 µg/hr/cm², about 15-40 µg/hr/cm², about 15-30 µg/hr/cm², about 15-25 µg/hr/cm², about 15-20 µg/hr/cm², about 20-30 µg/hr/cm², or about 20-25 µg/hr/cm². In other embodiments, the release rate is modulated to below about 30 µg/hr/cm², about 20 µg/hr/cm², about 15 µg/hr/cm², about 10 µg/hr/cm², about 8 µg/hr/cm², about 6 µg/hr/cm², or about 5 µg/hr/cm².

In even further embodiments, the initial release rate is adjusted or modulated to about 0.25-10 µg/hr/cm², about 0.5-10 µg/hr/cm², about 1-10 µg/hr/cm², about 2-10 µg/hr/cm², or about 1-10 µg/hr/cm².

In one embodiment, the polymer is a mixture or blend of low molecular weight polymers (LMWP) and high molecular weight polymers (HMWP). The ratio of LMWP to HMWP can be adjusted to modify the drug release rate profile. The ratio of LMWP and HMWP may be adjusted to generate a desired release rate profile. In one preferred embodiment, the ratio of LMWP and HMWP is adjusted to provide for a constant (e.g., zero-order) release of the drug. In another preferred embodiment, the ratio of LMWP and HMWP is adjusted to provide for a no-burst release of the drug. In yet another embodiment, the ratio of LMWP and HMWP is adjusted to modify or modulate the initial release rate of the drug without significantly affecting the sustained release rate.

Typically LMW biodegradable polymers degrade rapidly and polymer matrices formed from LMW polymers provide a rapid release rate for drugs dissolved or suspended in the matrix. Conversely, HMW biodegradable polymers degrade more slowly and provide a slow release rate for drugs dissolved or suspended in a HMW polymer matrix. LMWP have less entanglement than HMWP which typically have a more porous structure. For blends of LMWP and HMWP, the LMWP can "plug" the free volume in the HMWP structure.

The polymers used may possess a variety and range of molecular weights. In one embodiment, the LMWP has a molecular weight of about 1000-10K Da. In specific embodiments, the LMWP has a molecular weight of about 1000 Da, about 2000 Da, about 3000 Da, about 4000 Da, about 5000 Da, about 6000 Da, about 7000 Da, about 8000 Da, about 9000 Da, or about 10,000 Da. In other embodiments, the LMWP has a molecular weight of about 1000-5000 Da. In particular embodiment, the LMWP is polylactide having a molecular weight of about 1000 Da. In an embodiment, the HMWP has a molecular weight of about 50-300K Da. In other embodiments, the HMWP has a molecular weight of about 50-70K Da. In further embodiments, the HMWP has a molecular weight of about 200-300K Da. In specific, but not limiting embodiments, the HMWP has a molecular weight of about 50K Da, about 60K Da, or about 70K Da.

Figure 7:
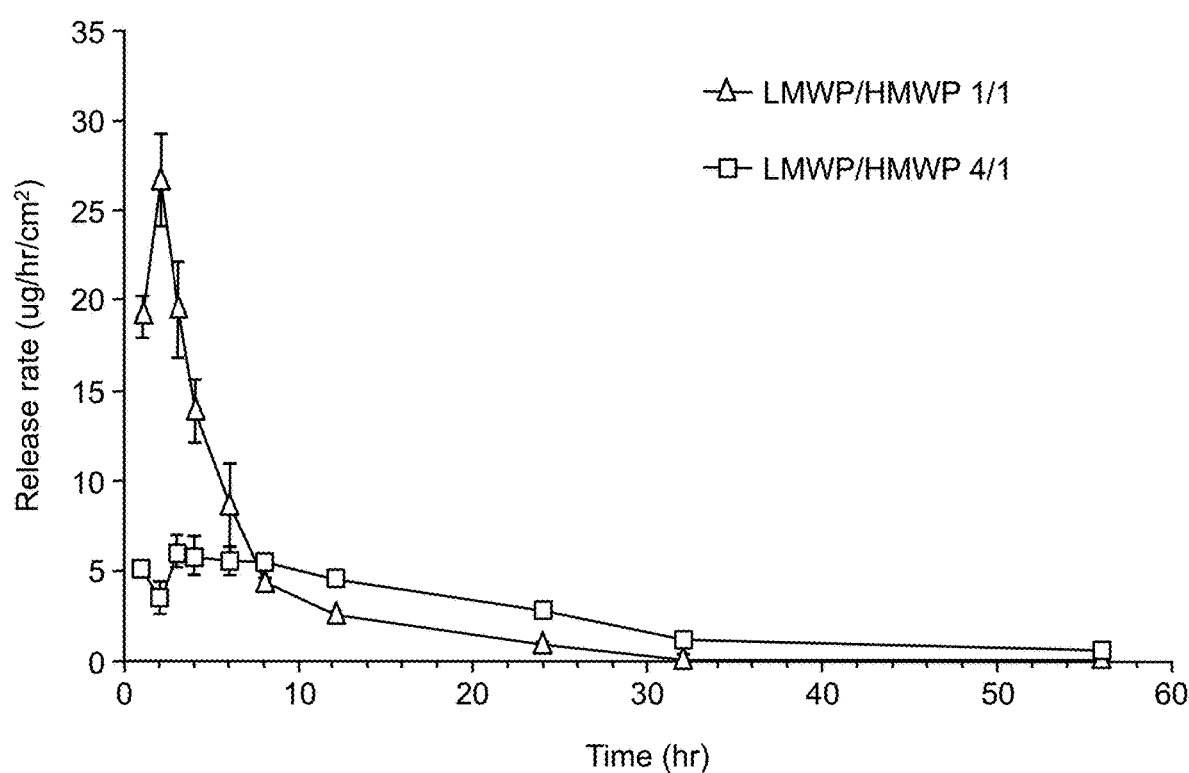
FIG. 7 is a graph of drug release rate in μg/hr/cm$^2$ for exemplary microstructure arrays prepared with a LMWP to HMWP ratio of 1:1 or a LMWP to HMWP ratio of 4:1 over time in hours.

Adjusting the blend or proportion of LMWP and HMWP in a hydrophobic polymer matrix could significantly change the drug release profile. As described in Example 5, microstructure arrays comprising a drug in a PLGA polymer matrix were prepared including a 1:1 ratio of LMWP to HMWP or a 4:1 ratio of LMWP to HMWP. The HMWP had a molecular weight of about 76K Da-120K Da. The release rate of the arrays was determined by immersing the array in a phosphate buffer and taking samples at specific time points and analyzing drug content in the sample by HPLC. FIG. 7 is a graph of the release rate of the drug in µg/hr/cm$^2$ for microstructure arrays comprising LMWP/HMWP of 1:1 (Δ) and LMWP/HMWP of 4:1 (□) over time in hours. The 1:1 formulation had an initial burst of about 18-25 µg/hr/cm$^2$. The 4:1 formulation had little to no initial burst with an initial release rate of about 3-6 µg/hr/cm$^2$. The 1:1 formulation had release of the drug for about 30 hours and the 4:1 formulation had release of the drug for at least about 56 hours.

The release rate of the therapeutic agent may be modulated by the ratio of drug/polymer in the DIT matrix. The initial release rate of the drug is especially sensitive to this ratio. Different release rate profiles can be achieved by changing the drug/polymer ratio.

Figure 8:
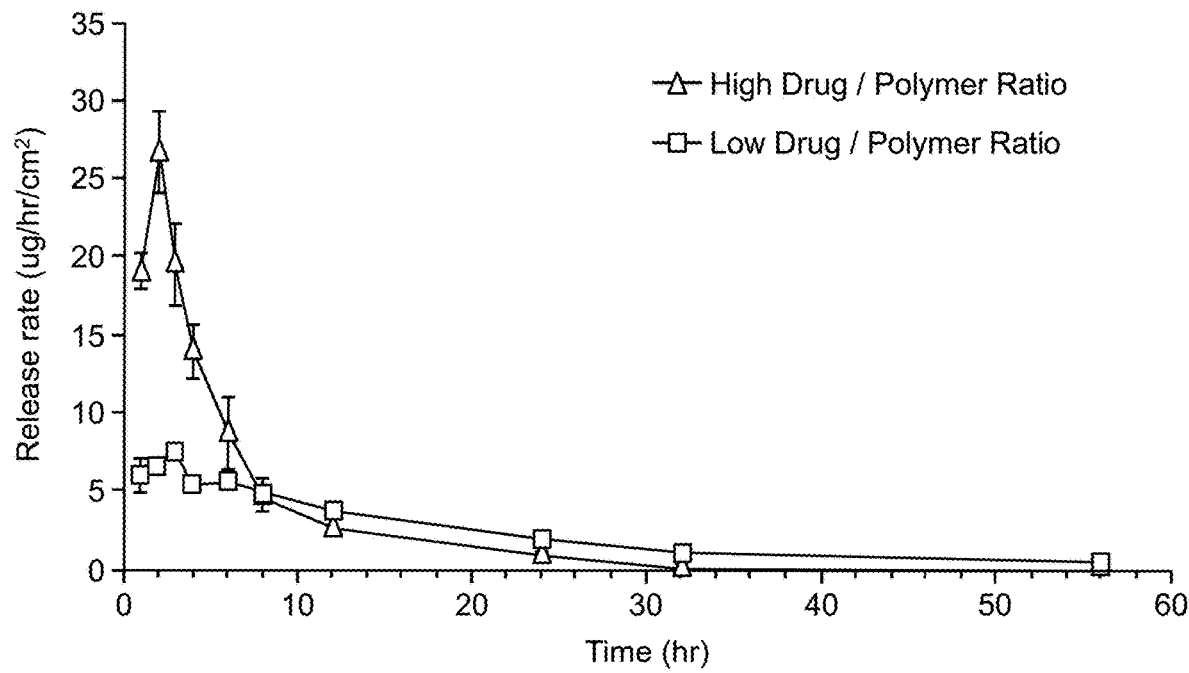
FIG. 8 is a graph of drug release rate in μg/hr/cm$^2$ for exemplary microstructure arrays prepared with a high drug to polymer ratio or a low drug to polymer ratio over time in hours.

As shown in FIG. 8, a slower initial release and flatter release rate profile is obtained with lower drug/polymer matrix ratio. The low drug/polymer ratio formulation had an initial release rate of about 5-8 µg/hr/cm$^2$ while the high drug/polymer ratio formulation had an initial release rate of about 18-25 µg/hr/cm$^2$.

Figure 4:
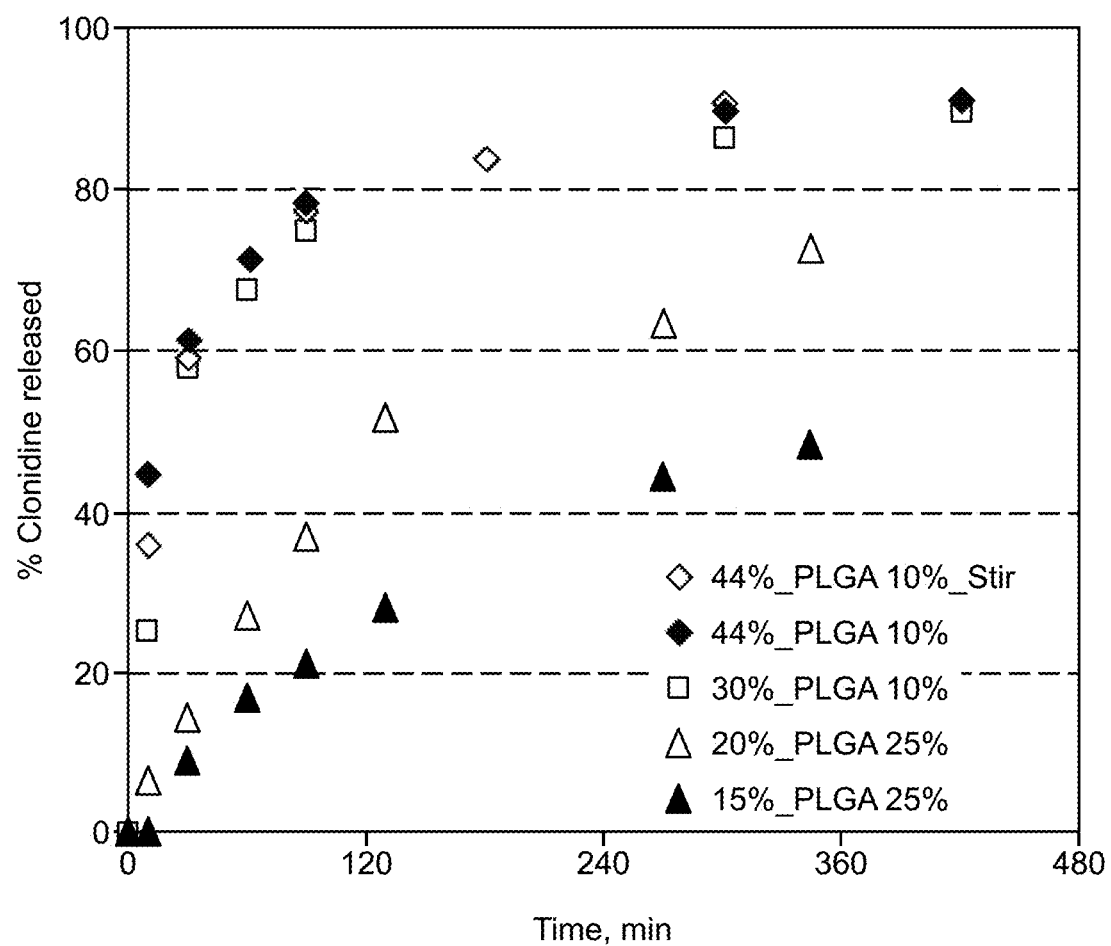
FIG. 4 is a graph of % Clonidine released from microstructures formed with 10% or 25% PLGA polymer matrices over time in minutes. The polymer matrix comprised 15%, 20%, 30%, or 44% drug load.

As described in Example 3, the effect of drug load and the ratio of drug to polymer on drug release rate was investigated by immersing microstructure arrays in a phosphate buffer, taking samples at specific time points and analyzing drug content in the sample by HPLC. FIG. 4 is a graph of the % Clonidine released from the microstructure array over time in minutes. Arrays were prepared having 44% Clonidine/10% PLGA (◇) (including stirring), 44% Clonidine/10% PLGA (◆), 30% Clonidine/10% PLGA (□), 20% Clonidine/25% PLGA (Δ), and 15% Clonidine/25% PLGA (▲). The MSA with a 44% and a 30% Clonidine drug load had about a 55% increase in the percentage of drug released after 120 minutes over the 15% Clonidine loaded MSA. The MSA with a 44% or 30% Clonidine drug load had about a 45% increase in the percentage of drug released after 240 minutes over the 15% Clonidine loaded MSA. The MSA with a 44% or 30% Clonidine drug load had about a 30% increase in the percentage of drug released after 360 minutes over the 15% Clonidine loaded MSA. The MSA with a 20% Clonidine drug load had about a 15-20% increase in the percentage of drug released after 120, 240, or 360 minutes over the 15% Clonidine loaded MSA. The MSA with a 44% and a 30% Clonidine drug load had about a 35-40% increase in the percentage of drug released after 120 minutes over the 20% Clonidine loaded MSA. The MSA with a 44% or 30% Clonidine drug load had about a 25% increase in the percentage of drug released after 240 minutes over the 20% Clonidine loaded MSA. The MSA with a 44% or 30% Clonidine drug load had about a 10-15% increase in the percentage of drug released after 360 minutes over the 20% Clonidine loaded MSA.

As seen in FIG. 4, two formulations having 44% Clonidine/10% PLGA were prepared. For one formulation (◇), the release medium was stirred. The formulation may be stirred constantly during release or at the time of sampling. A mild shake was used for the second formulation (◆). As seen in FIG. 4, the release medium is substantially homogeneous with no significant drug concentration gradient build up around the releasing MSA for both methods.

As described in Example 5, microstructure arrays comprising Clonidine in a PLGA polymer matrix with a high drug to polymer ratio and a low drug to polymer ratio were prepared. The release rate of the arrays was determined by immersing the array in a phosphate buffer and taking samples at specific time points and analyzing drug content in the sample by HPLC. FIG. 8 is a graph of the release rate of the drug in µg/hr/cm$^2$ for microstructure arrays comprising High Drug/Polymer Ratio (Δ) or Low Drug/Polymer Ratio (□) over time in hours. The array with the high drug to polymer ratio formulation had an initial burst of about 18-27 µg/hr/cm$^2$. The low drug to polymer ratio formulation had little to no initial burst with an initial release rate of about 5-7 µg/hr/cm$^2$. The high drug to polymer ratio formulation had release of the drug for about 32 hours and the low drug to polymer ratio formulation had release of the drug for at least about 56 hours.

In embodiments, the ratio of the drug to the polymer may be adjusted to modulate the release rate of the drug from the polymer matrix. It will be appreciated that the ratio of drug to polymer may be lower in order to lower the release rate, especially for lowering the initial release rate. It will further be appreciated that the ratio of drug to polymer may be higher in order to increase the release rate, especially for increasing the initial release rate. In embodiments, either the ratio of the therapeutic agent to the polymer in the polymer matrix or the ratio of the polymer to the therapeutic agent in the polymer matrix is about 1:1 to about 1:25. In further embodiments, the ratio is about 1:1-1:20, about 1:1-1:15, about 1:1-1:10, about 1:1-1:6, about 1:1-1:5, about 1:1-1:4, about 1:1-1:3, about 1:1-1:2; about 1:2-1:25, about 1:2-1:20, about 1:2-1:15, about 1:2-1:10, about 1:2-1:6, about 1:2-1:5, about 1:2-1:4, about 1:2-1:3, about 1:4-1:25, about 1:4-1:20, about 1:4-1:15, about 1:4-1:10, about 1:4-1:6, about 1:4-1:5. In specific non-limiting embodiments, the ratio of the therapeutic agent to the polymer in the polymer matrix or the ratio of the polymer to the therapeutic agent in the polymer matrix is about 1:1, about 1:2, about 1:3, about 1:4, about 1:5, about 1:6, about 1:7, about 1:8, about 1:9, about 1:10, about 1:15, about 1:20, about 1:25, or greater.

It will be appreciated that the methods for modulating the release rate may be combined without limitation. Specifically, the release rate may be modulated or adjusted by any one of the combined or separate methods described herein including adding a hydrophilic component to the polymer matrix, adjusting the drug to polymer ratio in the polymer matrix, using a blend of LMWP and HMWP and/or adjusting the ratio of the polymers in the polymer matrix, the choice of solvent in preparing the polymer matrix, and/or a heat treatment.

In another aspect, the microstructure arrays provide an increased drug load. Many microstructure arrays include a DIT portion that penetrates the skin and a proximal or backing layer that does not penetrate the skin. The drug load is limited by the volume of the DIT (or penetrated portion) of the microstructures, among other factors. Sustained release dosage forms in particular may require a higher dose load in the microstructure array as the drug is administered over an extended period of time. In one embodiment, the dose load of microstructure arrays and/or dose delivered from the arrays is increased by modifying the method of preparing the microstructure arrays and/or modifying the microstructure array configuration. In another embodiment, the release rate profile is modified by the microstructure arrays produced by the modified method.

Figures 11A, 11B, 11C:
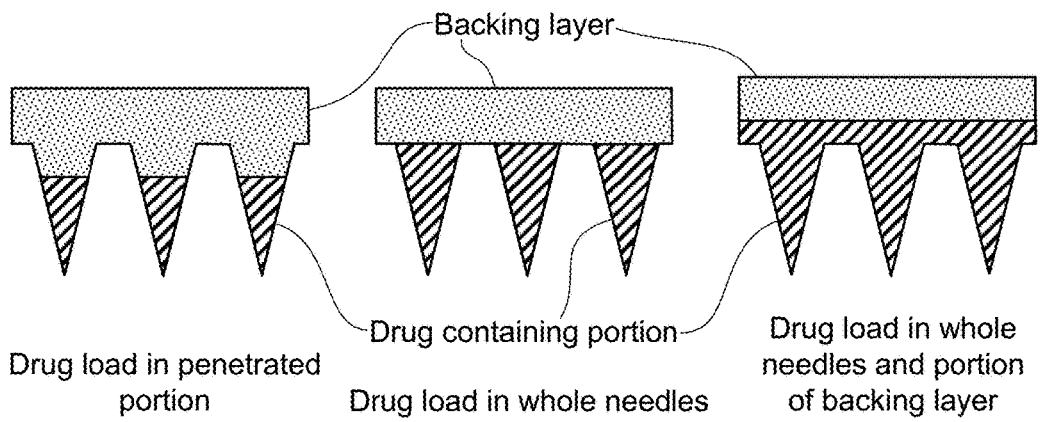
FIGS. 11A-11C are illustrations of exemplary microstructure arrays showing drug loaded in the penetrating portion of the microstructures (FIG. 11A), drug loaded in the whole or entire microstructure (FIG. 11B), and drug loaded in the whole microstructure and a portion of the backing layer or substrate (FIG. 11C).

Many previous microstructure arrays provide a DIT configuration where the drug is loaded in a penetrating portion (FIG. 11A). Modifying the microstructure configuration to provide drug load in the entire microstructure portion (penetrating and non-penetrating portions) as in FIG. 11B or to provide drug load in the entire microstructure portion (penetrating and non-penetrating portions) as well as in at least a portion of a backing layer as in FIG. 11C provides a higher volume of the microstructure array with drug loaded.

The configurations of FIGS. 11B and 11C also provide for a sustained release of the drug based. It will be appreciated that the configurations of FIGS. 11B and 11C may provide sustained release of a therapeutic agent for microstructure arrays for the sustained release microarrays described herein as well as with known microarrays such as those described in U.S. Publication No. U.S. 2008/0269685 and U.S. 2011/0276028 among others.

Further, the configurations of FIGS. 11B (whole MS embodiment) and 11C (whole plus MS embodiment) can be used to modulate or tailor the drug release rate. In one embodiment, the whole MS or whole plus MS configuration is used to provide sustained drug release with or without an initial burst. It will be appreciated that the whole MS or whole plus MS configurations may be used with any one or all of the methods to adjust the drug release rate as described above.

Figure 12A:
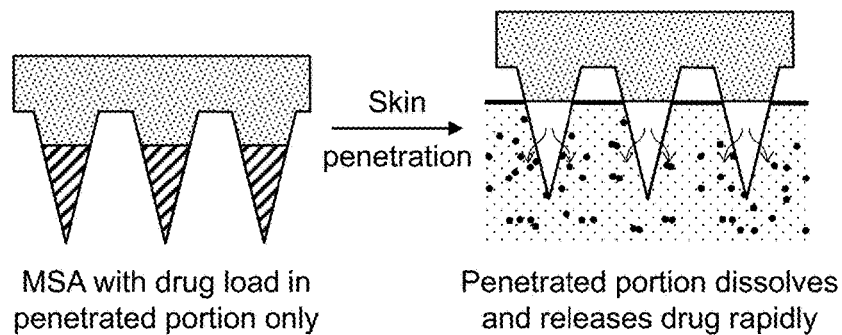
FIGS. 12A-12C are illustrations of exemplary microstructure arrays in use.
Figure 12B:
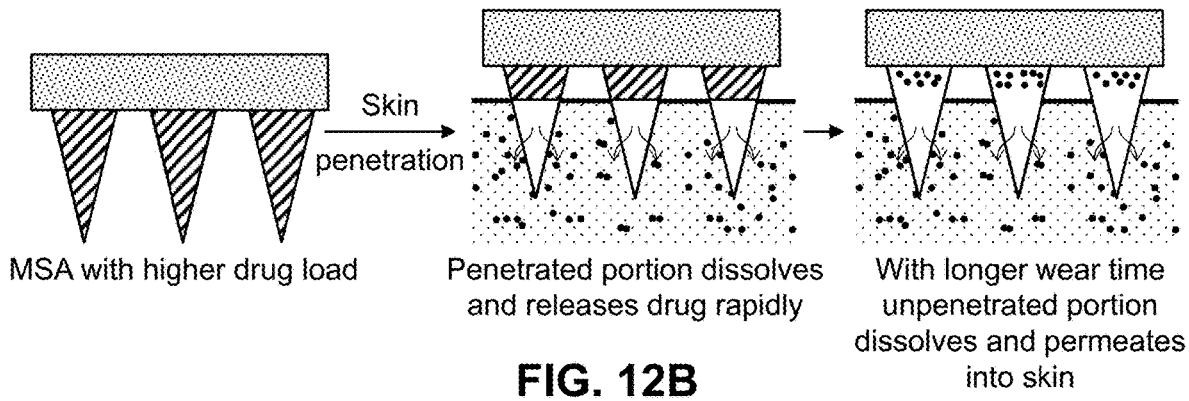
Figure 12C:
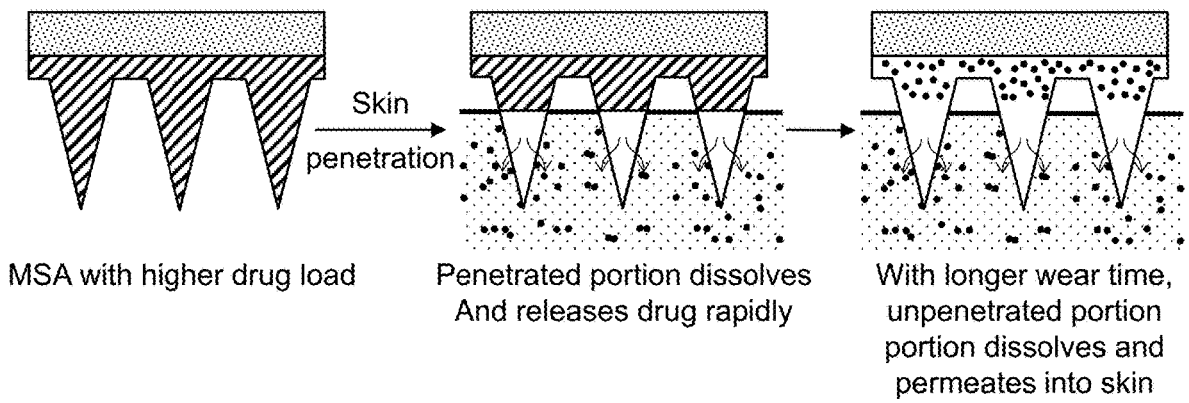

As shown in FIG. 12A, many present microstructure arrays provide for rapid delivery of drug incorporated in the portion of the microstructures that penetrate the skin. The penetrated portion may dissolve rapidly and release the drug rapidly. The array may then be removed after a period of time applied on/in the skin, e.g. 5-15 minutes. In one embodiment, the whole MS or whole plus MS configuration provide an initial release of drug from the penetrated portion of the microstructure and a sustained release from the non-penetrating portions. As seen in FIGS. 12B and 12C, the microstructure array with higher drug load (whole MS as in FIG. 12B or whole plus MS as in FIG. 12C) is applied to the subject's skin. The penetrated portion of the microstructure dissolves and releases the drug relatively rapidly. The array is left in place and the non-penetrated portion of the microstructures of both the whole MS and whole plus MS configurations dissolve and permeate into the skin. It will be appreciated that channels or pores formed by the administration of the microstructures into the skin will remain in the skin for a period of time after the penetrating portion has dissolved. The drug dissolved from the non-penetrating portion and/or the backing layer may thus be delivered into the stratum corneum. Depending on water back diffusion and drug permeation into the skin, the non-penetrating portion and/or backing layer may dissolve more slowly than the penetrating portion. Thus, the drug release profile may be modified to deliver the drug at a slower rate than delivered from the penetrating portion. It will be further appreciated that the penetrating portion, the non-penetrating portion and/or the backing layer may be modified to adjust the release rate, for example by the methods described above. In other embodiments, the penetrating portion is formed of a biodegradable, water soluble polymer matrix, as known in the art, and the non-penetrating portion and/or backing layer is formed of a biodegradable, water insoluble polymer matrix as described above.

The microstructure arrays may be formed by any suitable means as known in the art. A method of casting a microstructure array having drug loaded in the penetrating portions of the microstructures as shown in FIG. 11A is described in Example 7. In one embodiment, the microstructure arrays are formed by dissolving an API and excipients in an aqueous buffer as described in Example 6. In embodiments, the excipients may be any one of or any combination of a structure-forming polymer, a sugar which can stabilize the API and/or plasticize the structure-forming polymer, a surfactant and/or an antioxidant agent. In non-limiting embodiments, the API can be polypeptides, such as human parathyroid hormone (1-34) [(hPTH(1-34)] (MW 4118), proteins such as human growth hormone (hGH) (MW~22000), antibodies (MW~150000), or a vaccine with an antigen epitope conjugated on a carrier protein formulated with or without adjuvant. Examples of the structure-forming polymers are hydrophilic, water soluble polymers, such as polysaccharides like Dextran 70, Dextran 40, Dextran 10, Hetastarch, Tetrastarch, cellulose derivatives, and other water soluble polymers like polyvinyl pyrrolidone, polyvinyl alcohol, polyethylene glycol, copolymer of ethylene glycol and propylene glycol (Pluronic®), and/or block copolymers of PLGA-PEG. Sugars can act as a stabilizing agent for biological APIs like peptides, proteins, and antibodies, and/or can act as a plasticizer agent. Exemplary sugars include sorbitol, sucrose, trehalose, fructose, and/or dextrose. When Dextran, Hetastarch, and/or Tetrastarch are used as the structure-forming polymer in the polymer matrix, sorbitol is a preferred sugar because it can not only stabilize the API, but also plasticize the polymer matrix to make it less brittle. In some cases, a surfactant may be needed in the DIT formulation to change the surface tension and/or reduce protein adsorption and denaturation at interfaces. Exemplary surfactants include Polysorbate 20 and Polysorbate 80. Some APIs may be susceptible to oxidation either in the liquid DIT formulation or in solid DIT form. Exemplary antioxidant agents include, but are not limited to, methionine, cysteine, D-alpha tocopherol acetate, EDTA, and/or vitamin E. Exemplary liquid casting formulations containing an API are provided in Table 1 and described in Example 6.

Example 8 describes a casting method for forming microstructure arrays with drug loaded in the whole microstructure as shown in FIG. 11B. Briefly, about 70 µL of a liquid casting solution such as those described in Table 3 is dispensed on a mold having a plurality of cavities therein, covered with a flat surface to spread the formulation, and the formulation is moved into the cavities. The liquid casting solution has a solid content greater than 20% (w/w). When dried, the solids fill a greater portion of the microstructures. The cavities may be filled by pressurization or with a soluble gas such as $CO_2$ or $CH_4$. The mold is wiped and dried using two primary drying steps. The mold is first placed in a controlled humidity chamber having elevated humidity, about 10-95% RH, for 1-30 minutes at room temperature. In one embodiment, the humidity in the chamber is controlled to 85% RH. Second, the mold is placed in an oven, such as an incubator oven, at 32° C. for about 30 minutes. A backing layer formulation is cast on the dried drug formulation to connect the drug formulations. Exemplary backing layer formulations are provided in Table 4 in Example 6. The mold with backing layer is dried in an oven for about 30-90 minutes. In one embodiment, the mold is dried in a convection oven. It will be appreciated that the oven may use any one of convection, conduction, or radiation for drying. In one embodiment, the mold is dried at an elevated temperature of about 5-50° C. In one particular embodiment, the mold is dried in a convection oven at about 45° C.

The whole MS microstructure arrays may also include a substrate as described above. In Example 8, a UV adhesive is dispersed on the backing layer, covered with a 5 mm sheet of polycarbonate (PC) film and cured using a UV Fusion system. The array undergoes a final drying step under vacuum (about 0.05 torr) overnight. The final drying step may be at room temperature or at an elevated temperature, e.g. 35° C. The array is demolded and die cut into 1-2 cm² arrays. The microstructure arrays may be sealed in a storage container. In one embodiment, the MSAs are sealed individually in a Polyfoil pouch. It will be appreciated that the pouch may be sealed under nitrogen.

Example 9 describes a casting method for forming microstructure arrays with drug loaded in the whole microstructure plus at least a portion of the backing layer as shown in FIG. 11C. Briefly, about 70 μL of a liquid casting solution such as those described in Table 3 is dispensed on a mold having a plurality of cavities therein. In one embodiment, as described in Example 9, PET polymer disk with a circular opening is placed on a silicone mold. About 50 μL of a liquid casting solution as described in Table 3 in Example 6 is dispensed on the mold, covered with a flat surface to spread the formulation, and the formulation is moved into the cavities/the cavities are filled. The cavities may be filled by pressurization or with a soluble gas such as $CO_2$ or $CH_4$. The mold is wiped and dried using two primary drying steps. The mold is placed in an oven, such as an incubator oven, at 5-50° C. The drug is loaded in the whole microneedle and part of the backing layer. A backing layer formulation is cast on the dried drug formulation. Exemplary backing layer formulations are provided in Table 4 in Example 6. The mold is dried in an oven for about 30-120 minutes. In one embodiment, the mold is dried at an elevated temperature of about 5-50° C. In one particular embodiment, the mold is dried in a convection oven at about 45° C. The mold may be placed in a compressed dry air box for about 30 minutes with controlled air flow before being placed in the oven.

Figure 13:
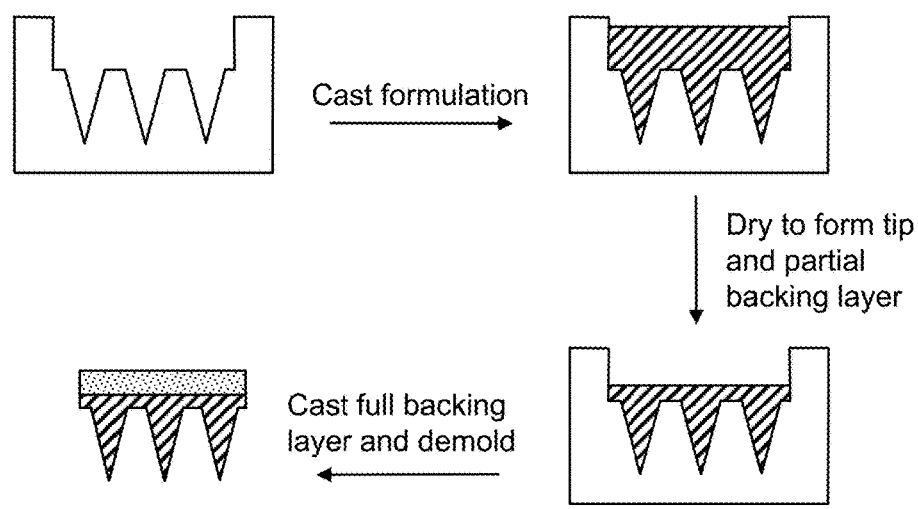
FIG. 13 is an illustration of an exemplary method of forming microstructure arrays having drug loaded in the whole microstructure and a portion of the backing layer or substrate.

In another embodiment, the drug layer and backing layer may be fabricated in one step as illustrated in FIG. 13. In this embodiment, the mold preferably has an extended or elevated side to allow the casting of the integrated microstructure and backing layer. The mold may be formed with the sides or may include a barrier placed around the cavities on top of the mold. The casting formulation is dispensed in the mold with elevated sides and dried to form the integrated microstructure and partial backing layer having a drug loaded therein. The mold is dried as described above, and a full backing layer is cast on the partial backing layer.

The whole plus MS microstructure arrays may also include a substrate as described above. In Example 9, a UV adhesive is dispersed on the backing layer, covered with a 5 mm sheet of polycarbonate (PC) film and cured using a UV Fusion system. The array undergoes a final drying step under vacuum (about 0.05 torr) overnight. The final drying step may be at room temperature or at an elevated temperature, e.g. 35° C. The array is demolded and die cut into 1-2 cm² arrays. The microstructure arrays may be sealed in a storage container. In one embodiment, the MSAs are sealed individually in a Polyfoil pouch. It will be appreciated that the pouch may be sealed under nitrogen.

Microstructure arrays with a whole plus MS configuration and comprising PTH may be prepared in accord with Example 9. The MSA with the whole plus MS configuration have a significantly higher drug load than DIT microstructure arrays. The MSA with the whole plus MS configuration also have a significantly higher drug load than whole MS configured microstructure arrays. The drug load for the whole plus MS PTH arrays is expected to be about 450 μg/cm² for the whole plus MS configuration as compared to 45-49 μg/cm² for the whole MS configuration and 32 μg/cm² for the DIT configuration. The drug load for the whole plus MS configuration increases by about 650-900% over the whole MS configuration and by about 420% for the DIT arrays for the PTH arrays.

B. Extended Wear Microstructure Arrays

In one embodiment, the present microarrays are suitable for extended wear. Extended wear microarrays may be useful for sustained delivery of drugs or agents and/or to allow complete delivery of the drug or agent, e.g. to allow a biodegradable microstructure to degrade enough to release all or most of the drug or agent. Improving adhesion between the microarray and the subject's skin may improve or contribute to improving drug delivery efficiency. Microarrays are typically adhered to the skin to allow delivery of drugs by an adhesive layer around the perimeter of the microarray and/or by an adhesive backing that overlies and extends beyond the edge of the microarray. These methods may be unsuitable for extended wear applications as the microstructures are not secured to the subject's skin and the array may pull-up or detach from the skin at least in some in areas. This is especially likely for areas of the microarray that are more removed from the perimeter adhesive such as the center of the array.

The microarrays of the present embodiment include at least one adhesive to adhere the array to the skin for a desired period of time. Preferably, the adhesive is included as part of the microarray itself or is placed or available in the interior of microarray rather than being applied around a perimeter of the microarray. In one embodiment, the microstructure array geometry is modified to allow an adhesive to contact the skin in one or more locations in the microstructure array region or interior. In a second embodiment, an adhesive layer is included in the microstructure array construct.

In one embodiment, the adhesive is a medical adhesive, tissue adhesive and/or surgical adhesive. In other embodiments, the adhesive is a medical adhesive such as those used to attach medical devices to skin. Suitable medical adhesives include, but are not limited to acrylic adhesives, silicone based adhesives, hydrogel adhesives, and synthetic elastomer adhesives. In one embodiment tissue adhesive is a bioadhesive polymer. Suitable tissue adhesives include, but are not limited to, cyanoacrylate polymers. Suitable cyanoacrylate polymers include, but are not limited to, n-butyl-2-cyanoacrylate (e.g., Histoacryl®, PeriAcryl®), 2-octyl cyanoacrylate (e.g. Dermabond®, SurgiSeal), and isobutyl cyanoacrylate. In another embodiment, the adhesive is a fibrin sealant. In a further embodiment, the adhesive is a bioactive film. In a yet further embodiment, the adhesive is an acrylic pressure sensitive adhesive. In even further embodiments, the adhesive is a rubber-based adhesive. Preferably, the adhesive is nonirritating and/or non-sensitizing. The adhesive may be selected based on tack and/or peel strength as required to adhere the microstructure array to skin. In some embodiments, the adhesive is breathable.

It will be appreciated that the adhesive may require a further component for adhesion such as a two-part adhesive. In other embodiments, the adhesive adheres on contact with water or a moist surface. In yet further embodiments, the adhesive is activated by pressure, heat, light (UV or visible), biochemical reactions, or a combination of activation methods. In an embodiment, the adhesive is a permanent adhesive. In other embodiments, the adhesive is designed to reduce its adhesion over time. In another embodiment, the adhesive reduces adhesion over time to match the expected wear period which permits easier removal of the array. The adhesive may be absorbable or degradable, which has one advantage that the array is easily removed when the adhesive is absorbed or degraded.

In one embodiment, an adhesive coating is at least partially applied to at least a portion of the microstructures of the array. In embodiments, one or more adhesives are used to coat the microstructures. In other embodiments, a portion of the microstructures are coated with one adhesive and other microstructures are coated with a further adhesive. The microstructures may be alternatively coated or the coatings may be applied in a pattern. For example, stronger adhesive may be alternated with a weaker adhesive. Alternatively, an absorbable adhesive may be alternated with one that is not so that the array is easier to remove yet remains attached until removed. It will be appreciated that the coating may be applied over all or a portion of at least a portion of the microstructures in the array.

In embodiments, at least about 10%-100% of the microstructures in the array are at least partially coated with an adhesive. In other embodiments, at least about 25%-30%, about 25%-40%, about 25%-50%, about 25%-60%, about 25%-70%, about 25%-75%, about 25%-80%, about 25%-90%, about 25%-95%, about 30%-100%, about 30%-40%, about 30%-50%, about 30%-60%, about 30%-70%, about 30%-75%, about 30%-80%, about 30%-90%, about 30%-95%, about 40%-100%, about 40%-50%, about 40%-60%, about 40%-70%, about 40%-75%, about 40%-80%, about 40%-90%, about 40%-95%, about 50%-100%, about 50%-60%, about 50%-70%, about 50%-75%, about 50%-80%, about 50%-90%, about 50%-95%, about 60%-100%, about 60%-70%, about 60%-75%, about 60%-80%, about 60%-90%, about 60%-95%, about 70%-100%, about 70%-75%, about 70%-80%, about 70%-90%, about 70%-95%, about 80%-100%, about 80%-90%, about 80%-95%, about 90%-100%, about 90%-95%, about 90%-100%, or about 95%-100% of the microstructures in the array are coated with an adhesive.

Figure 14:
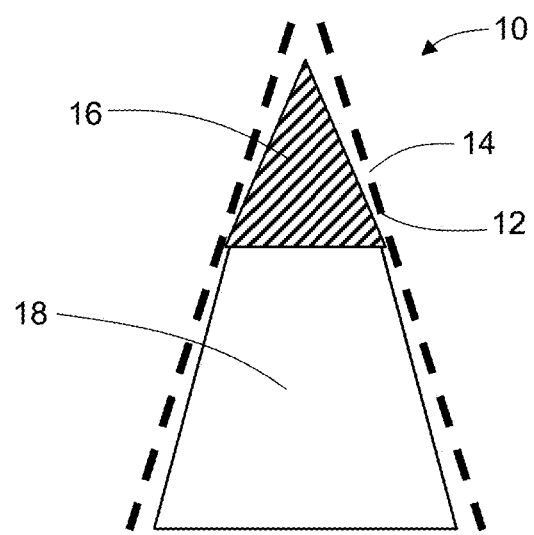
FIG. 14 is an illustration of a microstructure with a full adhesive layer.

As shown in FIG. 14, at least a portion of the microstructures 10 are coated with an adhesive coating 12. In one embodiment where the microstructures include a DIT portion 16, at least the DIT portion is coated with an adhesive. In other embodiments, only the backing layer, or at least a portion thereof, is coated with an adhesive. Alternatively, at least a portion of both the DIT portion 16 and the backing layer 18 are coated with an adhesive. The adhesive coating may directly contact all or a portion of the microstructures.

The coating may be applied directly to the microstructures or may be separated by a spacing and/or by an intermediate layer such as an intermediate polymer layer.

In one embodiment, the adhesive coating is porous to allow delivery of at least the drug. The adhesive may additionally contain or be configured with perforations, openings, or holes in at least a portion of the coating 14. This embodiment may be useful for biodegradable microstructures and/or where the drug does not easily pass through the adhesive. The perforations or openings may be any size or shape suitable for the drug and/or microstructure polymer to pass through. The perforations may be formed by any suitable method. In one embodiment, the perforations are formed mechanically and/or chemically. In one non-limiting embodiment, a portion of the coating is removed to form the perforations. In yet another embodiment, the perforations are formed by masking the microstructures and spray coating or dip coating the microstructure array and removing the masking agent. In a further embodiment where the coating is applied as part of a casting method, the microstructure mold may be configured so that the resulting coating includes perforations or is otherwise non-continuous. For example, the mold may include protrusions or other features within the mold interior that the coating does not cover. The resulting coating will be non-continuous, e.g. contain perforations or openings. In other embodiments, the coating is otherwise non-continuous over at least a portion of the microstructure surface. In another embodiment, the microstructures are spot coated with the adhesive.

Figure 15:
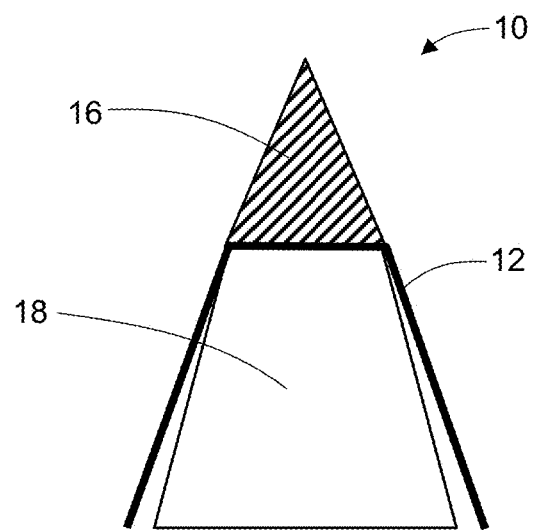
FIG. 15 is an illustration of a microstructure with a partial adhesive coating in one embodiment.

In another embodiment, only a portion of each microstructure (of the microstructures that are coated) is coated with an adhesive. In one embodiment, at least a portion of the distal end of the microstructures are coated. In another embodiment, at least a portion of the proximal end is coated. The coating may be selectively applied by any suitable means including, but not limited to, spray coating, dip coating, or be applied during formation of the microstructures. It will further be appreciated that methods used to coat microneedles with a therapeutic agent, e.g. those described in U.S. Pat. No. 8,057,842, may also be used to coat the microstructures with an adhesive. Where the microstructures are formed by casting the microstructures in a mold, the adhesive may be added at a point so that only the desired portion of the microstructure is coated. For example, where a portion of the distal tip is coated, the coating may be added to the mold prior to adding the polymer matrix, or matrices, of the microstructures. Where a portion of the proximal end is coated, the coating may be added to the mold after the polymer matrix for the distal tip is added. As shown in FIG. 15, the microstructure 10 includes a partial adhesive coating 12 that covers the proximal portion of the microstructure. In this embodiment, the microstructure includes a biodegradable distal tip 16 and a non-biodegradable proximal portion 18. Only the proximal portion that is not biodegradable is covered by the adhesive coating. In this embodiment, it is not necessary to use a porous adhesive or include perforations in the coating as the biodegradable portion is not coated. It will be appreciated that a partial coating may be porous and/or include non-continuous features as described above. It will further be appreciated that only the outer portion or surface of the proximal portion 18 of the microstructures may include the coating 12.

In embodiments, at least about 10%-100% of the microstructure is coated. In other embodiments, at least about 25%-30%, about 25%-40%, about 25%-50%, about 25%-60%, about 25%-70%, about 25%-75%, about 25%-80%, about 25%-90%, about 25%-95%, about 30%-100%, about 30%-40%, about 30%-50%, about 30%-60%, about 30%-70%, about 30%-75%, about 30%-80%, about 30%-90%, about 30%-95%, about 40%-100%, about 40%-50%, about 40%-60%, about 40%-70%, about 40%-75%, about 40%-80%, about 40%-90%, about 40%-95%, about 50%-100%, about 50%-60%, about 50%-70%, about 50%-75%, about 50%-80%, about 50%-90%, about 50%-95%, about 60%-100%, about 60%-70%, about 60%-75%, about 60%-80%, about 60%-90%, about 60%-95%, about 70%-100%, about 70%-75%, about 70%-80%, about 70%-90%, about 70%-95%, about 80%-100%, about 80%-90%, about 80%-95%, about 90%-100%, about 90%-95%, about 90%-100%, or about 95%-100% of the microstructure is coated with an adhesive (of the microstructures that are coated). It will be appreciated that these percentages apply both to embodiments that use a non-continuous adhesive coating and/or a partial adhesive coating.

Figure 16:
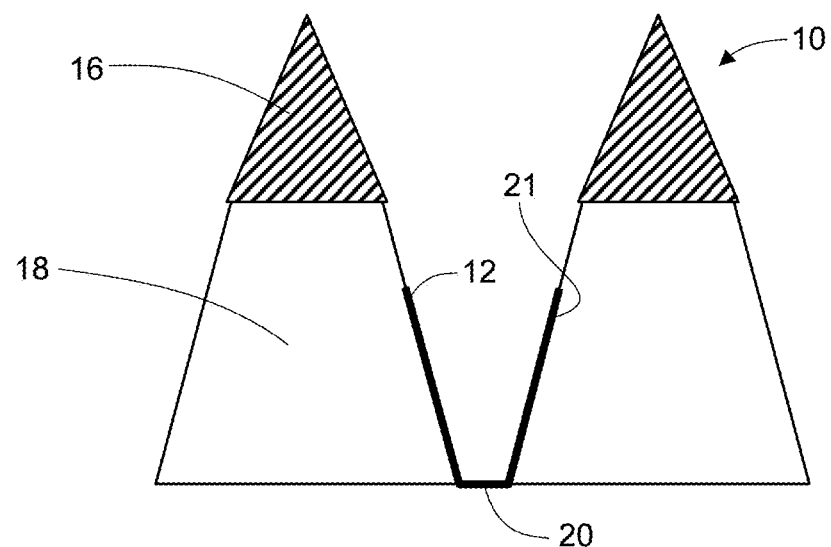
FIG. 16 is an illustration of a partial microstructure array with a partial adhesive coating.

In another embodiment, an adhesive coating is applied at least partially between at least a portion of the microstructures in the array. In one embodiment, the adhesive coating is applied to the substrate or backing between the microstructures. In another embodiment, as shown in FIG. 16, the coating is applied to the substrate or backing 20 between the microstructures 10. In this embodiment, the coating may also be applied at least partially to the proximal portion of the microstructures 21. In this non-limiting embodiment, the proximal portion 18 of the microstructure is non-biodegradable and the distal portion 16 including at least one agent is biodegradable. It will be appreciated that the coating may be applied only to the substrate or backing 20 between the microstructures. It will further be appreciated that the coating may be applied to the substrate or backing and all of a non-biodegradable proximal portion, where present.

Figure 17A:
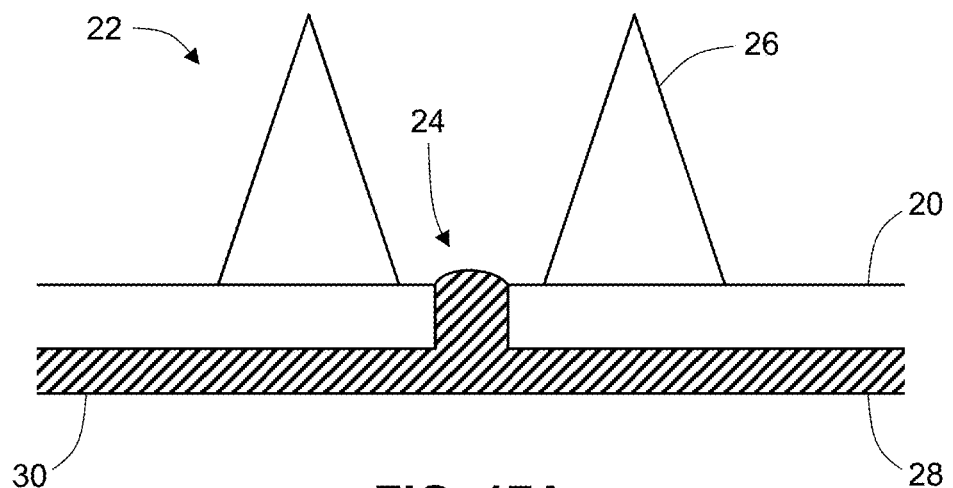
FIGS. 17A-17B are illustrations of embodiments of microstructure array geometry.
Figure 17B:
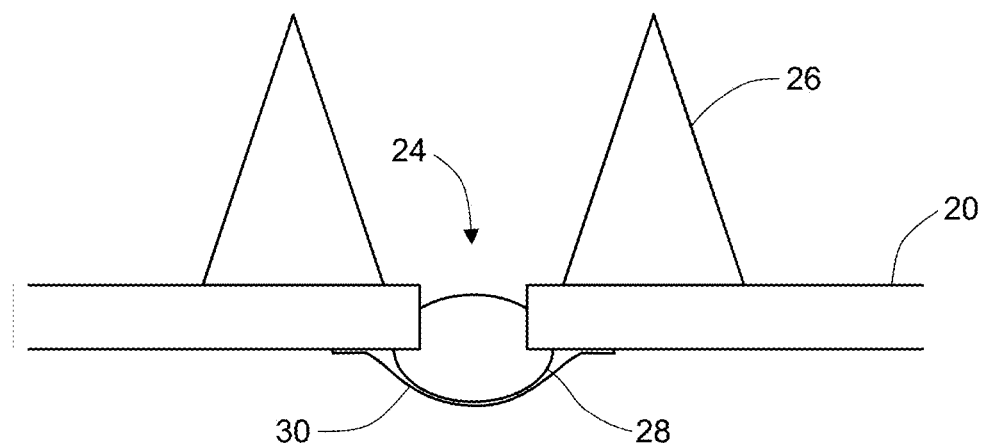

In another embodiment, the microstructure array is layered and includes an adhesive as one layer in the array. Exemplary embodiments where the microstructure geometry includes an adhesive are shown in FIGS. 17A-17B. In this embodiment, the adhesive is included as a layer on the substrate or backing which includes at least one opening or hole that allows the adhesive to contact the subject's skin. It will be appreciated that the number and placement of the openings may be selected to provide the desired adhesion. Placement of the openings may be selected according to a pattern to provide the desired adhesion of the microstructure array. The opening may be of any sufficient diameter for the adhesive to contact the skin. A larger diameter results in more contact between the skin and the adhesive. One skilled in the art can calculate the contact necessary, and therefore the required opening diameter, based at least one the adhesive properties of the adhesive such as adhesion strength.

FIG. 17A shows two microstructures 26 of a microstructure array 22 positioned on a substrate 20. The substrate includes a hole or opening 24 positioned between the microstructures. An adhesive layer 28 is positioned at least partially on the substrate on the surface opposite the microstructures. The adhesive can travel through the opening to contact the subject's skin. In one embodiment, pressure or another force is applied to the adhesive layer to move at least a portion of the adhesive through the opening to contact the skin. In another embodiment, the adhesive is sufficiently fluid to flow through the opening. In other embodiments, the adhesive may be altered to be sufficiently fluid to flow through the opening, e.g. by heating the adhesive. In yet another embodiment, the substrate layer is sufficiently thin and/or the opening is sufficiently large that the adhesive contacts the skin without flowing through the opening. The microstructure array may include a further adhesive backing layer 30 that overlies and contains the adhesive. In other embodiments, the adhesive is an adhesive tape or a double-sided adhesive coated nonwoven or porous film.

In another embodiment as shown in FIG. 17B, the adhesive 28 may be applied on the substrate 20 surface opposite the microstructures 26 as discrete portions at or near the opening(s) 24. As above, this embodiment may include an adhesive backing 30 positioned at least over the adhesive depots. One or more adhesives may be applied to the substrate. It will be appreciated that the adhesive applied at the depots may be selected so as to provide a desired effect. For example, a stronger adhesive may be alternated with a weaker adhesive. Alternatively, an absorbable adhesive may be alternated with one that is not so that the array is easier to remove yet remains attached until removed.

FIGS. 18A-18B show a substrate 20 without openings (FIG. 18A) and with a plurality of openings 24 (FIG. 18B).

III. Methods of Making Microstructure Arrays

Before describing the methods of manufacture in detail, it is to be understood that the methods are not limited to specific solvents, materials, or device structures, as such may vary. It is also to be understood that the terminology used herein is for the purpose of describing particular embodiments only, and is not intended to be limiting.

Examples of forming various microstructure arrays having different configurations are provided in Examples 1 and 4. In one exemplary method, an array is prepared by (a) filling a mold with cavities corresponding to the negative of the microstructures with a casting solution comprising a biocompatible material such as a biocompatible polymer and a solvent, (b) removing the solvent, and (c) de-molding the resulting array from the mold. The solvent may be removed by any suitable means including, but not limited, to drying the mold filled with the casting solution in an oven. The casting solution preferably contains an active agent or ingredient. In one or more embodiments, the microstructures themselves comprise the active ingredient mixed, or dispersed in a polymer matrix, as opposed to having the active ingredient present as a coating on a microstructure or microneedle made of a different, biocompatible material such as a metal. Typically, excess formulation is scraped or wiped from the mold surface prior to drying. Where the microstructures are not integral with a substrate or backing layer, the microstructures are affixed to the substrate or backing layer with an adhesive prior to de-molding. Further methods of preparing microstructure arrays are described in Examples 6-9.

IV. Methods of Use

The methods, kits, microstructure arrays and related devices described herein may be used for treating any condition. It will be appreciated that the microstructure arrays may be used with any appropriate applicator including the applicator described in U.S. Publication No. 2011/0276027, each of which are incorporated herein in their entirety.

In one aspect, a method for applying the microarrays described herein for an extended period is provided. In embodiments, the extended wear microarrays are secured to the subject's skin for at least about 5 minutes to 24 hours. In other embodiments, the extended wear microarrays are secured to the subject's skin for at least about 10 minutes to 24 hours, at least about 15 minutes to 24 hours, at least about 30 minutes to 24 hours, at least about 1-24 hours, at least about 1-2 hours, at least about 1-3 hours, at least about 1-4 hours, at least about 1-5 hours, at least about 1-6 hours, at least about 1-8 hours, at least about 1-10 hours, at least about 1-12 hours, at least about 2-24 hours, at least about 2-3 hours, at least about 2-4 hours, at least about 2-5 hours, at least about 2-6 hours, at least about 2-8 hours, at least about 2-10 hours, at least about 2-12 hours, at least about 3-24 hours, at least about 3-4 hours, at least about 3-5 hours, at least about 3-6 hours, at least about 3-8 hours, at least about 3-10 hours, at least about 3-12 hours, at least about 4-24 hours, at least about 4-5 hours, at least about 4-6 hours, at least about 4-8 hours, at least about 4-10 hours, at least about 4-12 hours, at least about 5-24 hours, at least about 5-6 hours, at least about 5-8 hours, at least about 5-10 hours, at least about 5-12 hours, at least about 8-10 hours, at least about 10-24 hours, at least about 10-12 hours, at least about 12-24 hours, or longer. In specific, but not limiting embodiments, the microarray is secured to the subject's skin for at least about 5 minutes, 10 minutes, 15 minutes, 30 minutes, 45 minutes, or longer. In other specific, but not limiting embodiments, the microarray is secured to the subject's skin for at least about 1 hour, 2 hours, 3 hours, 4 hours, 5 hours, 6 hours, 8 hours, 10 hours, 12 hours, 18 hours, 24 hours, or longer. In other embodiments, the extended wear microarrays are secured to the subject's skin for at least about 1-30 days. In further embodiments, the microarrays are secured to the subject's skin for at least about 1-2 days, at least about 1-3 days, at least about 1-4 days, at least about 1-5 days, at least about 1-7 days, at least about 10 days, at least about 1-14 days, at least about 1-21 days, or longer. In specific, but not limiting embodiments, the microarray is secured to the subject's skin for at least about 1 day, 2 days, 3 days, 4 days, 5 days, 6 days, 7 days, 10 days, 14 days, 21 days, 30 days, or longer.

In embodiments, the extended wear microarrays are secured to the subject's skin until a desired portion of the total drug or agent dose is delivered. The portion of the total dose delivered may be determined by any suitable method including without limitation a residual analysis of the device as known in the art. In other embodiments, the microarray is secured to the subject's skin until at least about 10-100% of the total dose of drug in the array is delivered. In further embodiments, the microarray is secured to the subject's skin until at least about 10-25%, about 10-50%, about 10-55%, about 10-60%, about 10-65%, about 10-70%, about 10-75%, about 10-80%, about 10-90%, about 10-95%, or about 10-99% of the total dose of drug in the array is delivered. In yet further embodiments, the microarray is secured to the subject's skin until at least about 25-50%, about 25-55%, about 25-60%, about 25-65%, about 25-70%, about 25-75%, about 25-80%, about 25-90%, about 25-95%, about 25-99%, about 50-55%, about 50-60%, about 50-65%, about 50-70%, about 50-75%, about 50-80%, about 50-90%, about 50-95%, about 50-99%, about 70-75%, about 70-80%, about 70-90%, about 70-95%, about 70-99%, about 75-80%, about 75-90%, about 75-95%, about 75-99%, about 80-90%, about 80-95%, about 80-99%, about 90-95%, about 90-99%, or about 95-99% of the total dose of drug in the array is delivered. In other embodiments, the microarray is secure to the subject's skin until at least about 25%, about 30%, about 55%, about 60%, about 65%, about 70%, about 75%, about 80%, about 90%, about 95%, or about 95% of the total dose is delivered to the subject.

In another aspect, a method for administering an active agent or therapeutic agent to a subject is provided. Preferably, the active or therapeutic agent is administered dermally, transdermally, mucosally, and/or transmucosally. The method comprises providing a microprojection array or other delivery device comprising at least one active agent. Preferably, the microprojection array or other delivery device is configured to deliver at least one therapeutic agent. The agent may be coated on at least a portion of the microprojections and/or contained within at least a portion of the microstructures. The agent is delivered dermally, transdermally, mucosally, or transmucosally into contact with the skin, or more generally a membrane or body surface, of a subject.

In one exemplary operation, an array is placed in contact with the skin and is adhered to the skin with an adhesive disposed at least partially on the microstructures or included as part of the array.

Figure 19:
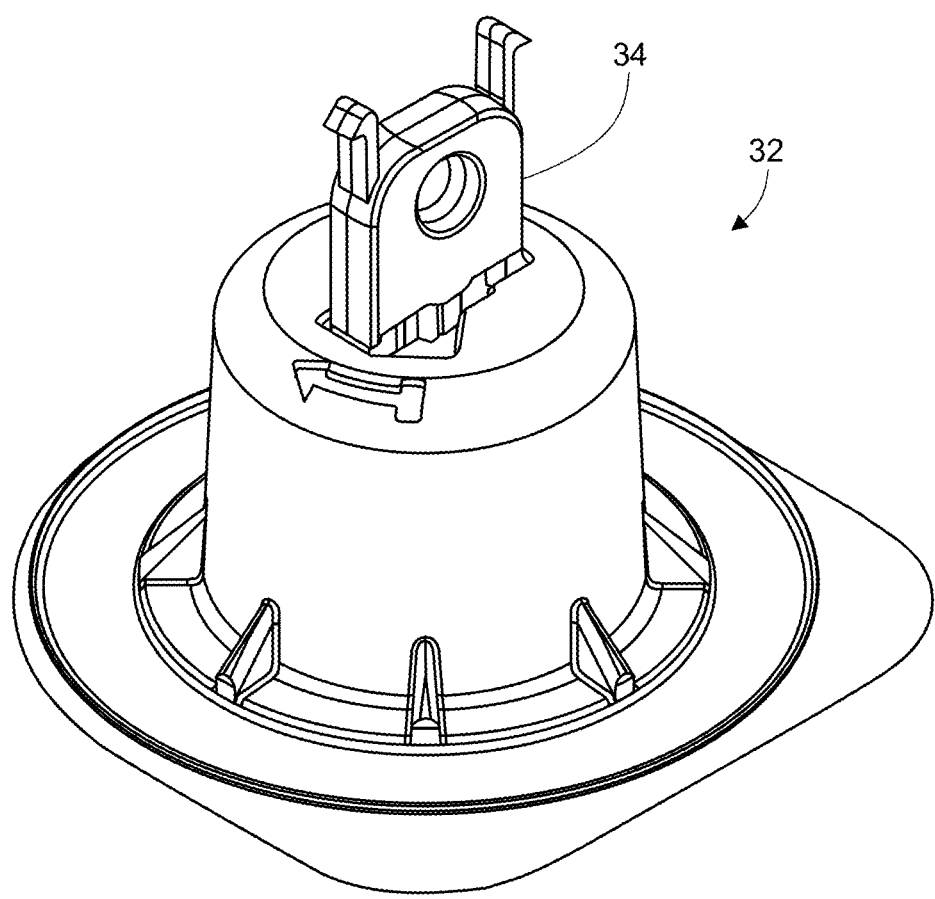
FIG. 19 is an illustration of a top perspective view of an exemplary applicator device.

The array may be applied using an applicator as known in the art. An exemplary applicator 32 is shown in FIG. 19. The applicator typically includes a plunger or piston where the microstructure array is positioned on a distal end of the plunger. An actuator or actuating member 34 is actuated to release the plunger. The plunger is typically held in a constrained or restrained position until released. The plunger impacts the skin and the microstructure array pierces or ruptures the skin surface. The microstructure array is removed from the plunger distal end automatically or manually. The adhesive adheres the microstructure array to the subject's skin for a desired period of time.

V. EXAMPLES

The following examples are illustrative in nature and are in no way intended to be limiting. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Example 1

Casting Sustained Release Arrays

Poly(D,L-lactide-co-glycolide) (PLGA, L/G 75/25) (available from Durect Corporation (PN B6007-1P) was dissolved in acetonitrile (ACN) or dimethylsufoxide (DMSO) to a concentration of 10 wt % or 25 wt % to form a polymer solution.

Clonidine or Tamsulosin hydrochloride were placed in a 15 mL polypropylene tube with the PLGA polymer solution. The drug was dissolved in the PLGA polymer solution by warming the mixture in closed tubes for 10-15 minutes in a convection oven and vortexing until the drug was completely dissolved. Formulations were prepared according to Table 1.

TABLE 1

PLGA/drug formulations

| Formulation | Drug | % drug in solid DIT | % PLGA in liquid casting solution | Solvent |
| --- | --- | --- | --- | --- |
| A1 | Clonidine | 44% | 10% | ACN |
| A2 | Tamsulosin | 44% | 10% | DMSO |
| A3 | Clonidine | 44% | 10% | DMSO |
| A4 | Clonidine | 30% | 10% | DMSO |
| A5 | Clonidine | 30% | 25% | ACN |
| A6 | Clonidine | 44% | 25% | ACN |
| A7 | Clonidine | 20% | 25% | ACN |
| A8 | Clonidine | 15% | 25% | ACN |

About 75 µL of liquid drug formulation was dispensed on a silicone based mold, covered with 22 mm×30 mm glass cover slip to spread the formulation on the mold, and then pressurized at 50 psi for 1 minute.

The formulation was wiped and the mold dried in a convection oven at 70° C. for 1.5 hours.

UV adhesive was dispensed on the drug formulation in the mold, covered with a 5 mm polyethylene terephthalate (PET) film to spread the adhesive and cured using a UV Fusion system. The UV curing dose was 1.6 J/cm$^2$. After curing, the microstructure (drug in tip distal layer and UV adhesive proximal layer on PET) was die cut with an 11 mm punch.

The resulting microstructures were inspected under microscope. Images of intact microstructure arrays with Clonidine (35% drug in PLGA DIT) are shown in FIGS. 1A-1B.

Example 2

Dissolution of Arrays

Microstructure arrays (MSA) comprising 35% Clonidine in PLGA DIT were prepared in accord with Example 1 were treated with acetonitrile to extract the PLGA DIT tips and then were inspected under microscope to observe the remaining stubs, which comprised the UV adhesive layer with an image taken from the sharp side of the microstructures shown in FIG. 2.

Example 3

Drug Release from Microstructure Arrays

Microstructure arrays comprising Clonidine or Tamsulosin were prepared in accord with Example 1. The microstructure arrays were immersed in closed 20 mL scintillation vials containing 10 mL phosphate buffer (pH=7.5, 10 mM) at 37° C. under mild shaking. At specified time points, 1 mL of release medium was removed for drug content analysis by HPLC. The sample was substituted with 1 mL of fresh buffer.

Figure 3:
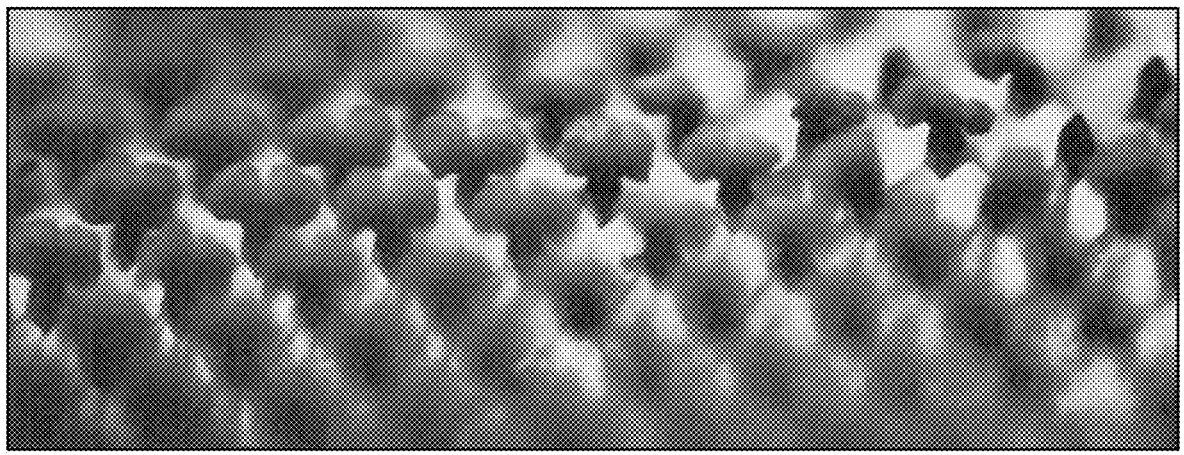
FIG. 3 is a microscopic image of an exemplary sustained release microstructure array after exposure to a phosphate buffer at 37° C. for one week.

After release experiments, the samples were inspected under a microscope. Swelling of PLGA DIT portions was observed after exposure for 1 week to phosphate buffer at 37° C. as shown in FIG. 3. It is theorized that the swelling of DIT after 1 week at 37° C. may be due to the void left from the release of the drug from the PLGA matrix and partial degradation of PLGA, which makes the polymer more hydrophilic.

The effect of Clonidine loading in PLGA DIT on cumulative drug release is shown in FIG. 4. Kinetic parameters, initial drug release rate (Δ % min) and time for the half drug released ($t_{50\%}$), which was calculated from the initial slope of the release curve, for the formulations shown in Table 1 are shown in Table 2. The Clonidine release rate decreased significantly with decreasing Clonidine load in the PLGA formulation.

TABLE 2

Drug Release Parameters

| Formulation | Initial Release Rate (Δ % min) | $t_{50\%}$ (min) | Total drug released mcg/array |
|---|---|---|---|
| A1 | 1.85 | 27 | 126 |
| A2 | 9.36 | 5 | 139 |
| A3 | 0.79 | 63 | 80.4 |
| A4 | 0.28 | 181 | 32.7 |
| A5 | 1.9 | 27 | 57.5 |
| A6 | 1.9 | 27 | 78 |
| A7 | 0.39 | 128 | 87.3 |
| A8 | 0.24 | 207 | 83.5 |

The type of solvent used to fabricate the PLGA DIT had a significant effect on the drug release rate. As shown in FIG. 5, Clonidine loaded arrays prepared using a DMSO solvent showed a significantly lower drug release rate as compared to Clonidine loaded arrays prepared using ACN. Tamsulosin loaded arrays prepared using a DMSO solvent had almost immediate drug release, which is likely due to the enhanced plasticization of the drug to the polymer by the DMSO solvent.

Example 4

Effect of Heat Treatment on Drug Crystallization in PLGA Films

Figure 6A:
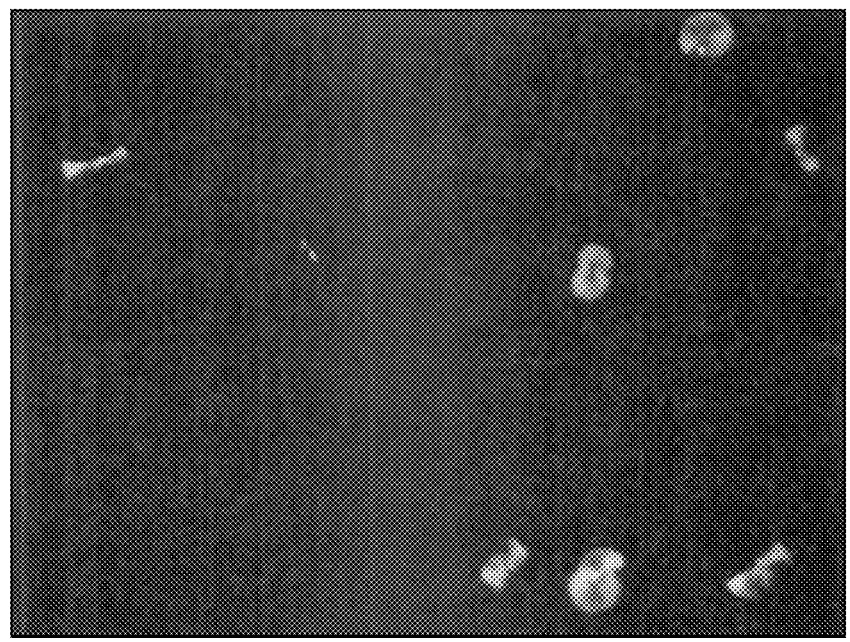
FIGS. 6A-6C are microscopic images of Clonidine in a PLGA film (drug load of 35%).

PLGA films loaded with 35% Clonidine were prepared by casting from ACN (PLGA concentration in liquid casting solution was 25%) on a microscope glass. The films were dried at 70° C. (which is below the melting point for Clonidine). An image of the film after casting and drying is shown in FIG. 6A, which shows Clonidine crystals formed in the film.

Figure 6B:
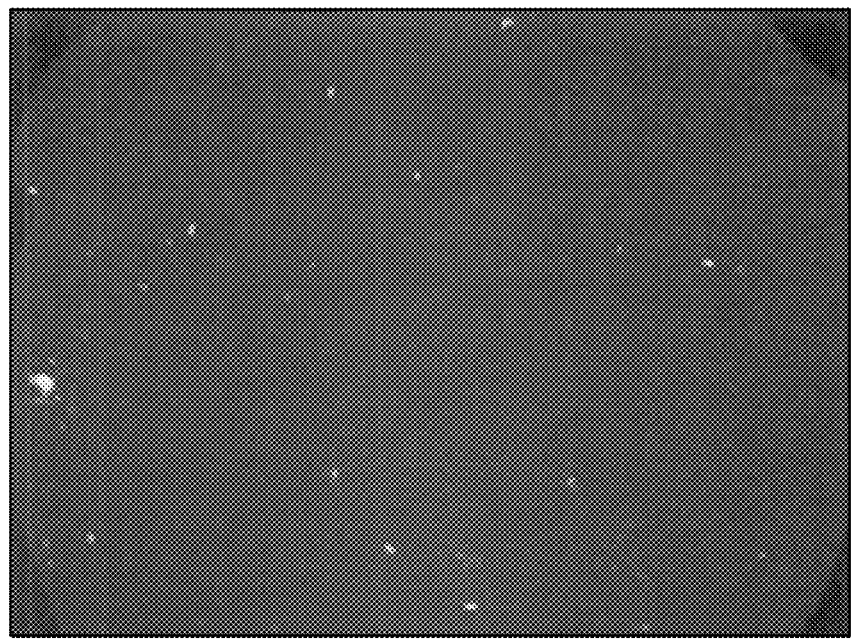
Figure 6C:
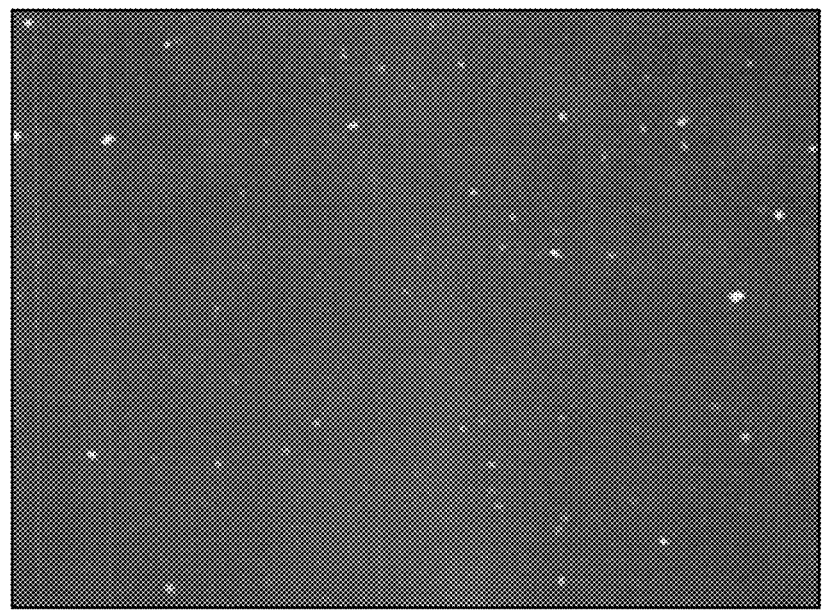

A spot in the films was marked to trace changes in the film. Films were heat treated in a convection oven at 110° C. for 1 hour and then stored in a dry cabinet for 10 days. FIG. 6B shows no Clonidine crystallization observed after heat treatment and storage. The small, bright particles observed in the image correspond to microscope glass background as evidenced by the control photograph of a microscope glass shown in FIG. 6C.

Example 5

Modulating Microstructure Array Release Profiles

Poly(DL lactide-co-glycolide) (PLGA, L/G 75/25) (available from Durect Corporation (PN B6007-1P, IV 0.55-0.75) was used as a high molecular weight polymer (HMWP) and PLGA (L/G 75/25) from SurModics (1 A, IV 0.1) was used as a low molecular weight polymer (LMWP).

PLGA was dissolved in acetonitrile (ACN) or dimethylsufoxide (DMSO) to a concentration of 10 wt % or 25 wt % to form a polymer solution.

Clonidine or Tamsulosin hydrochloride were placed in a 15 mL polypropylene tube with the PLGA polymer solution. The drug was dissolved in the PLGA polymer solution by warming the mixture in closed tubes for 10-15 minutes in a convection oven and vortexing until the drug was completely dissolved.

About 75 μL of liquid drug formulation was dispensed on a silicone based mold, covered with 22 mm×30 mm glass cover slip to spread the formulation on the mold, and then pressurized at 50 psi for 1 minute.

The formulation was wiped and the mold dried in an oven at 32° C. for 30 minutes, then dried at 50° C. under vacuum overnight.

UV adhesive was dispensed on the drug formulation in the mold, covered with a 5 mL polyethylene terephthalate (PET) or polycarbonate (PC) film to spread the adhesive and cured using a UV Fusion system. The UV curing dose was 1.6 J/cm². After curing, the microstructure (drug in tip distal layer and UV adhesive proximal layer on PET) was die cut with an 11 or 16 mm punch. The resulting microstructures were inspected under microscope and further vacuum dried at 35° C. overnight to remove any residual solvent.

A. In Vitro Release Rate

An in vitro release test was performed by immersing a microstructure array in a closed 20 mL scintillation vials containing 10 mL PBS buffer (pH=7.4) containing 0.1% Polysorbate 20, which was added at time=0. The vial was shaken at 100 rpm on an orbital shaking platform in an incubator at 37° C. One mL of release medium was removed at predetermined time points to quantify drug release. Fresh release medium was replenished to maintain the volume of the release medium.

B. Effect of LMWP/HMWP Ratio on Release Rate

Microstructure arrays were prepared using 1:1 LMWP/HMWP or 4:1 LMWP/HMWP for the polymer solution. An in vitro release test as above was performed with the results shown in FIG. 7.

C. Effect of Drug to Polymer Ratio on Release Rate

Microstructure arrays were prepared with a high drug/polymer ratio or low drug/polymer ratio. An in vitro release test as above was performed with the results shown in FIG. 8.

D. Effect of a Hydrophilic Component on Release Rate

Microstructure arrays were prepared in accord with the above method with the addition of 10%, 20%, or 40% of a hydrophilic PEG-PLGA component. An in vitro release test as above was performed with the results shown in FIG. 9.

Example 6

Casting Formulations

Liquid casting formulations are prepared by dissolving an active pharmaceutical ingredient (API) and excipients in an aqueous buffer as shown in Table 3.

TABLE 3

Liquid Casting Solution Formulations

| Formulation | Polymer | | Sugar | | API | | PS20 | EDTA |
| | Type | Wt % | Type | Wt % | Type | Wt % | Wt % | mg/mL |
| --- | --- | --- | --- | --- | --- | --- | --- | --- |
| B1 | Dextran 70 | 14 | Sorbitol | 5 | PTH | 1.8 | NA | NA |
| B2 | Dextran 70 | 10 | Sorbitol | 4 | PTH | 1.8 | NA | NA |
| B3 | Dextran 70 | 27 | Sorbitol | 9 | PTH | 1.8 | NA | NA |
| B4 | Dextran 70 | 21 | Sorbitol | 7.5 | PTH | 1.8 | NA | NA |
| B5 | Tetrastarch | 14 | Sorbitol | 7 | PTH | 1.8 | NA | NA |
| B6 | Tetrastarch | 10 | Sorbitol | 5 | PTH | 1.8 | NA | NA |
| B7 | Hetastarch | 14 | Sorbitol | 7 | PTH | 1.8 | NA | NA |
| B8 | Hetastarch | 10 | Sorbitol | 5 | PTH | 1.8 | NA | NA |
| B9 | Dextran 40 | 14 | Sorbitol | 5 | PTH | 1.8 | NA | NA |
| B10 | Dextran 70 | 14 | Sorbitol | 5 | PTH | 2.8 | NA | NA |
| B11 | PVA | 14 | Sucrose | 5 | PTH | 2.8 | NA | NA |

Different polymeric solutions may be used for casting a basement or backing layer for the microstructure arrays. Liquid formulations for a backing layer are prepared by dissolving one or more polymers in a solvent or solvent mixture at or about room temperature with a polymer concentration of about 10-40% by weight. Liquid formulations for casting a backing layer are prepared according to Table 4.

TABLE 4

Liquid Backing Layer Formulations

| Formu- | Polymer | | Solvent | |
| lation | Type | Wt % | Type | Wt % |
| --- | --- | --- | --- | --- |
| C1 | Eudragit EPO 100 | 20 | Ethanol/IPA (3:1) | 80 |
| C2 | Eudragit EPO 100 | 30 | Ethanol/IPA (3:1) | 70 |
| C3 | Eudragit EPO 100/PVP (1:1) | 20 | Ethanol/IPA (3:1) | 80 |
| C4 | PLGA (75/25) | 10 | Ethyl acetate | 90 |
| C5 | PLGA (75/25) | 15 | Ethyl acetate | 85 |
| C6 | PLGA (75/25) | 25 | Acetonitrile | 75 |
| C7 | PLGA (75/25) | 35 | Acetonitrile | 65 |
| C8 | PLGA (65/35) | 20 | Acetonitrile | 80 |
| C9 | PLGA (65/35) | 30 | Acetonitrile | 70 |
| C10 | PLA | 20 | Acetonitrile | 80 |

Example 7

Casting Microstructure Arrays with Drug in Penetrating Portion

About 70 µL of liquid casting solution formulation number B1 was dispensed on a silicone mold having diamond shaped cavities (200 µm length, base width 70 µm, and 200 µm needle to needle spacing), covered with a 22 mm×30 mm glass cover slip to spread the formulation on the mold, and then pressurized at 50 psi for 1 minute. The filled volume of liquid casting solution formulation was about 1.5-2.0 µL/cm². The solid content of the liquid formulations was less than 20% (w/w).

The formulations were wiped and the mold dried in a controlled humidity chamber with elevated humidity such as 85% RH for 1-30 minutes at room temperature. The mold was then placed in an incubator oven at 32° C. for about 30 minutes.

Backing layer formulation C6 was cast on the mold to connect the dried casting formulation in the cavities. The mold was dried in a compressed dry air (CDA) box for 30 minutes with controlled air flow and then in a convection oven at 45° C. for 30-90 minutes.

A second layer of backing layer formulation may be cast on the mold, and the mold additionally dried in a compressed dry air (CDA) box for 30 minutes with controlled air flow and then in a convection oven at 45° C. for 30-90 minutes.

UV adhesive was dispensed on the backing layer, covered with a small sheet of 5 mm polycarbonate (PC) film to spread the adhesive and cured using a UV Fusion system. The UV curing dose was 1.6 J/cm². After curing, the microstructure array (drug in tip distal layer/PLGA backing layer/UV adhesive substrate on PC backing) was removed from the mold and die cut into 1-2 cm² arrays.

The microstructure array was dried to remove residual moisture from the drug distal layer and residual solvent from the backing layer. The mold was dried under vacuum (0.55 torr) at 35° C. or room temperature overnight. The drug load for PTH was 32 µg/cm².

Example 8

Casting Microstructure Arrays with Increased Drug Load

About 70 µL of liquid casting solution formulation number B3 or B4 was dispensed on a silicone mold having diamond shaped cavities (200 µm length, base width 70 µm, and 200 µm needle to needle spacing), covered with a 22 mm×30 mm glass cover slip to spread the formulation on the mold, and then pressurized at 50 psi for 1 minute. The filled volume of liquid casting solution formulation in the mold was about 2.5-3.3 µL/cm². The solid content of these liquid formulations was greater than 20% (w/w) so solids can fill the cavities beyond the portion of the resulting microstructures that will penetrate skin when the distal layer is dried.

The formulations were wiped and the mold dried in a controlled humidity chamber with elevated humidity such as 85% RH for 1-30 minutes at room temperature. The mold was then placed in an incubator oven at 32° C. for about 30 minutes.

Backing layer formulation C6 was cast on the mold to connect the dried casting formulation in the cavities. The mold was dried in a CDA box for 30 minutes with controlled air flow and then in a convection oven at 45° C. for 30-90 minutes.

UV adhesive was dispensed on the backing layer, covered with a small sheet of 5 mm polycarbonate (PC) film to spread the adhesive and cured using a UV Fusion system. The UV curing dose was 1.6 J/cm². After curing, the microstructure array (drug in tip distal layer/PLGA backing layer/UV adhesive substrate on PC backing) was removed from the mold and die cut into 1-2 cm² arrays.

The microstructure array was dried to remove residual moisture from the drug distal layer and residual solvent from the backing layer. The mold was dried under vacuum (0.55 torr) at 35° C. or room temperature overnight. Exemplary drug loads for the drug distal layer are listed in Table 5.

TABLE 5

Microstructure Array Drug Load for Drug Distal Layer

| MSA | Liquid DIT Formulation | API | Liquid Load Volume (μL/cm²) | Drug load μg/cm² MSA |
|---|---|---|---|---|
| D1 | B3 | PTH | 3.3 | 59 |
| D2 | B4 | PTH | 2.5 | 45 |
| D3 | B4 | PTH | 3.3 | 59 |

Example 9

Casting Microstructure Arrays with Drug in Penetrating Portion and Backing Layer A PET disk with a circular opening area of about 2 cm² is placed on a silicone mold having diamond shaped cavities (200 μm length, base width 70 μm, and 200 μm needle to needle spacing). To this circular area, about 50 μL of liquid casting solution formulation is dispensed on a silicone mold, covered with a 22 mm×30 mm glass cover slip to spread the formulation on the mold, and then pressurized at 50 psi for 1 minute.

The mold is then placed in an incubator oven at 32° C. for about 30 minutes.

Backing layer formulation is cast on top of the dried drug containing layer in the mold. The mold is dried in a CDA box for 30 minutes with controlled air flow and then in a convection oven at 45° C. for 30-90 minutes.

UV adhesive is dispensed on the backing layer, covered with a small sheet of 5 mm polycarbonate (PC) film to spread the adhesive and cured using a UV Fusion system. The UV curing dose was 1.6 J/cm². After curing, the microstructure array (drug in tip distal layer and partial backing layer/PLGA backing layer/UV adhesive substrate on PC backing) is removed from the mold and is die cut into 1-2 cm² arrays.

The microstructure array is dried to remove residual moisture from the drug layer and residual solvent from the backing layer. The mold is dried under vacuum (0.55 torr) at 35° C. or room temperature overnight.

Example 10

In Vivo Skin Penetration Efficiency and Apparent Dose Delivery Efficiency

Microstructure arrays (MSAs) comprising PTH were prepared in accord with Example 8. MSAs were applied to shaved skin sites of rats or pigs using a custom made applicator and held in situ (either manually by hand or with skin contact adhesive) for a period time (e.g., 1-5 minutes). After removing the applicator, the MSAs were kept on the animals for 5 minutes or 2 hours.

Residual drug remaining in the MSA was extracted by immersing the used MSA in an aqueous extraction medium for ~30 min and assayed using an appropriate analytical method, e.g. SEC-HPLC. The apparent delivered dose per unit, and delivery efficiency are then calculated as follows with the results shown in Table 6:

Apparent delivered dose=Initial drug load−Residual drug

% Drug delivery efficiency=100×Apparent delivered dose/Initial drug load

TABLE 6

Apparent Dose Delivered

| MSA | API | Animal | Apparent Dose (μg/cm²) | |
|---|---|---|---|---|
| | | | 5 min wear | 2 hr wear |
| D1 | PTH | Rat | 45 | 60 |
| D2 | PTH | Pig | 48 | 64 |

For MSAs with drug loaded in the entire microneedle, the apparent dose delivered increases with increasing wear time, a phenomenon that was observed in both rats and pigs. Table 6 shows the apparent dose delivered in vivo for hPTH(1-34) MSA after 5 min and 2 hour wear times. Apparent dose delivered increased with wear time by 33% for PTH in rats and pigs.

Example 11

In Vivo Pharmacokinetics

Microstructure arrays (MSAs) comprising a protein are prepared in accord with Example 8. MSAs are applied to shaved skin sites of rats or pigs using a custom made applicator and held in situ (either manually by hand or with skin contact adhesive) for a period time (e.g., 1-5 minutes). After removing the applicator, the MSAs are kept on the animals for 5 minutes or 2 hours. The serum concentration PK profiles may be plotted by taking blood samples at predetermined times (e.g. 0.5, 1, 2, 3, 4, 5, 6, 7, 8, 9, 10 hours etc.) and determining the serum concentration of the API. It is expected that serum concentrations of the API will be higher for the 2 hr wear compared to the 5 min wear. The overall systemic exposure should correspond to the mean apparent doses achieved by the wear time. Thus, where the wear time for 5 min. vs. 2 hours results in a double in the mean apparent dose, the overall systemic exposure, e.g. represented by area under the curve (AUC), should also increase or even double. Increasing the MSA wear time can increase overall systemic drug delivery 1. A microstructure apparatus, comprising:
    an approximately planar substrate having a first surface and a second surface opposed thereto; and
    a microstructure array comprising a plurality of microstructures contacting the first surface of the substrate and fixedly attached thereto, the microstructures being formed of a polymer matrix comprising (i) a water insoluble, biodegradable polymer, and (ii) at least one therapeutic agent;
    wherein release of the therapeutic agent from the polymer matrix is sustained for a period of at least about 1-144 hours.

2. The microstructure apparatus of embodiment 1, wherein the water insoluble polymer is selected from polylactide, polyglycolide, and co-polymers thereof.

3. The microstructure apparatus of the combined or separate embodiments 1-2, wherein the polymer matrix comprises about 1-50% therapeutic agent.

4. The microstructure apparatus of the combined or separate embodiments 1-3, wherein the polymer matrix comprises about 10-50% therapeutic agent.

5. The microstructure apparatus of the combined or separate embodiments 1-4, wherein the polymer matrix comprises about 20-50% therapeutic agent.

6. The microstructure apparatus of the combined or separate embodiments 1-5, wherein the polymer matrix comprises about 25-50% therapeutic agent.

7. The microstructure apparatus of the combined or separate embodiments 1-6, wherein the polymer matrix comprises about 30-50% therapeutic agent.

8. The microstructure apparatus of the combined or separate embodiments 1-7, wherein the polymer matrix comprises about 45-50% therapeutic agent.

9. The microstructure apparatus of the combined or separate embodiments 1-8, wherein the polymer matrix comprises about 50-99% of the water insoluble, biodegradable polymer.

10. The microstructure apparatus of the combined or separate embodiments 1-9, wherein the polymer matrix comprises about 50-90% of the water insoluble, biodegradable polymer.

11. The microstructure apparatus of the combined or separate embodiments 1-10, wherein an initial release rate of the therapeutic agent from the polymer matrix is between about 0.05-10%/minute.

12. The microstructure apparatus of the combined or separate embodiments 1-11, wherein an initial release rate of the therapeutic agent from the polymer matrix is between about 0.5-10%/minute.

13. The microstructure apparatus of the combined or separate embodiments 1-12, wherein an initial release rate of the therapeutic agent from the polymer matrix is between about 1-10%/minute.

14. The microstructure apparatus of the combined or separate embodiments 1-13, wherein an initial release rate of the therapeutic agent from the polymer matrix is between about 2-10%/minute.

15. The apparatus of the combined or separate embodiments 1-14, wherein release of the therapeutic agent from the polymer matrix is sustained for a period of at least about 144 hours.

16. The apparatus of the combined or separate embodiments 1-15, wherein release of the therapeutic agent from the polymer matrix is sustained for a period of at least about 72 hours.

17. The apparatus of the combined or separate embodiments 1-16, wherein release of the therapeutic agent from the polymer matrix is sustained for a period of at least about 24 hours.

18. The apparatus of the combined or separate embodiments 1-17, wherein release of the therapeutic agent from the polymer matrix is sustained for a period of at least about 12 hours.

19. The apparatus of the combined or separate embodiments 1-18, wherein release of the therapeutic agent from the polymer matrix is sustained for a period of at least about 6 hours.

20. The apparatus of the combined or separate embodiments 1-19, wherein release of the therapeutic agent from the polymer matrix is sustained for a period of at least about 3 hours.

21. The apparatus of the combined or separate embodiments 1-20, wherein release of the therapeutic agent from the polymer matrix is sustained for a period of at least about 1 hour.

22. The apparatus of the combined or separate embodiments 1-21, wherein the microstructures are detachable from the substrate.

23. The apparatus of the combined or separate embodiments 1-22, wherein the therapeutic agent is selected from a drug, a small molecule, a peptide or protein, or a vaccine.

24. A microstructure apparatus, alone or combined with any of the embodiments herein, comprising:
    an approximately planar substrate having a first surface and a second surface opposed thereto; and
    a microstructure array comprising a plurality of microstructures contacting the first surface of the substrate and fixedly attached thereto, the microstructures being formed of a polymer matrix comprising (i) at least one low molecular weight polymer, (ii) at least one high molecular weight polymer, and (iii) at least one therapeutic agent;
    wherein an initial release rate of the therapeutic agent from the polymer matrix is between about 0.05-10%/minute;
    wherein release of the therapeutic agent from the polymer matrix is sustained for a period of at least about 1-144 hours.

25. The apparatus of embodiment 24, wherein the polymer matrix comprises at least one water insoluble, biodegradable polymer.

26. The apparatus of the combined or separate embodiments 24-25, wherein at least one of the low molecular weight polymer or the high molecular weight polymer is the water insoluble, biodegradable polymer.

27. The apparatus of the combined or separate embodiments 24-26, wherein the water insoluble, biodegradable polymer is selected from polylactide, polyglycolide, and co-polymers thereof.

28. The apparatus of the combined or separate embodiments 24-27, wherein the initial release rate is between about 0.5-10%/minute.

29. The apparatus of the combined or separate embodiments 24-28, wherein the initial release rate is between about 1-10%/minute.

30. The apparatus of the combined or separate embodiments 24-29, wherein the initial release rate of the therapeutic agent from the polymer matrix is less than about 1-10%/minute.

31. The apparatus of the combined or separate embodiments 24-30, wherein the low molecular weight polymer has a molecular weight of between about 1-10K Da.

32. The apparatus of the combined or separate embodiments 24-31, wherein the high molecular weight polymer has a molecular weight of between about 50-300K Da.

33. The apparatus of the combined or separate embodiments 24-32, wherein the high molecular weight polymer has a molecular weight of between about 50-70K Da.

34. The apparatus of the combined or separate embodiments 24-33, wherein the low molecular weight polymer and high molecular weight polymers are present in a ratio of about 1:1-1:10.

35. The apparatus of the combined or separate embodiments 24-34, wherein the low molecular weight polymer and high molecular weight polymers are present in a ratio of about 1:1.

36. The apparatus of the combined or separate embodiments 24-35, wherein the low molecular weight polymer and high molecular weight polymers are present in a ratio of about 1:4.

37. The apparatus of the combined or separate embodiments 24-36, wherein release of the therapeutic agent from the polymer matrix is sustained for a period of at least about 144 hours.

38. The apparatus of the combined or separate embodiments 24-37, wherein release of the therapeutic agent from the polymer matrix is sustained for a period of at least about 72 hours.

39. The apparatus of the combined or separate embodiments 24-38, wherein release of the therapeutic agent from the polymer matrix is sustained for a period of at least about 24 hours.

40. The apparatus of the combined or separate embodiments 24-39, wherein release of the therapeutic agent from the polymer matrix is sustained for a period of at least about 12 hours.

41. The apparatus of the combined or separate embodiments 24-40, wherein release of the therapeutic agent from the polymer matrix is sustained for a period of at least about 6 hours.

42. The apparatus of the combined or separate embodiments 24-41, wherein release of the therapeutic agent from the polymer matrix is sustained for a period of at least about 3 hours.

43. The apparatus of the combined or separate embodiments 24-42, wherein release of the therapeutic agent from the polymer matrix is sustained for a period of at least about 1 hour.

44. The apparatus of the combined or separate embodiments 24-43, wherein the microstructures are detachable from the substrate.

45. The apparatus of the combined or separate embodiments 24-44, wherein the therapeutic agent is selected from a drug, a small molecule, a peptide or protein, or a vaccine.

46. A microstructure apparatus, comprising:
    an approximately planar substrate having a first surface and a second surface opposed thereto; and
    a microstructure array comprising a plurality of microstructures contacting the first surface of the substrate and fixedly attached thereto, the microstructures being formed of a polymer matrix comprising (i) at least one biodegradable polymer, (ii) a hydrophilic component, and (iii) at least one therapeutic agent;
    wherein release of the therapeutic agent from the polymer matrix is sustained for a period of at least about 1-144 hours.

47. The apparatus of embodiment 46, wherein the biodegradable polymer is a water insoluble, biodegradable polymer.

48. The apparatus of the combined or separate embodiments 46-47, wherein release of the therapeutic agent from the polymer matrix is sustained for a period of at least about 4-24 hours.

49. The apparatus of the combined or separate embodiments 46-48, wherein release of the therapeutic agent from the polymer matrix is sustained for a period of at least about 4-8 hours.

50. The apparatus of the combined or separate embodiments 46-49, wherein release of the therapeutic agent from the polymer matrix is sustained for a period of at least about 144 hours.

51. The apparatus of the combined or separate embodiments 46-50, wherein release of the therapeutic agent from the polymer matrix is sustained for a period of at least about 72 hours.

52. The apparatus of the combined or separate embodiments 46-51, wherein release of the therapeutic agent from the polymer matrix is sustained for a period of at least about 24 hours.

53. The apparatus of the combined or separate embodiments 46-52, wherein release of the therapeutic agent from the polymer matrix is sustained for a period of at least about 12 hours.

54. The apparatus of the combined or separate embodiments 46-53, wherein release of the therapeutic agent from the polymer matrix is sustained for a period of at least about 6 hours.

55. The apparatus of the combined or separate embodiments 46-54, wherein release of the therapeutic agent from the polymer matrix is sustained for a period of at least about 3 hours.

56. The apparatus of the combined or separate embodiments 46-55, wherein release of the therapeutic agent from the polymer matrix is sustained for a period of at least about 1 hour.

57. The apparatus of the combined or separate embodiments 46-56, wherein the polymer matrix comprises about 5%-40% of the hydrophilic component.

58. The apparatus of the combined or separate embodiments 46-57, wherein the polymer matrix comprises about 5%-10% of the hydrophilic component.

59. The apparatus of the combined or separate embodiments 46-58, wherein the polymer matrix comprises about 5%-40% of the hydrophilic component.

60. The apparatus of any the combined or separate embodiments 46-59, wherein the polymer matrix comprises up to about 40% of the hydrophilic component.

61. The apparatus of the combined or separate embodiments 46-60, wherein the polymer matrix comprises up to about 20% of the hydrophilic component.

62. The apparatus of the combined or separate embodiments 46-61, wherein the polymer matrix comprises up to about 10% of the hydrophilic component.

63. The apparatus of the combined or separate embodiments 46-62, wherein an initial release rate of the therapeutic agent from the polymer matrix is between about 0.05-10%/minute.

64. The apparatus of the combined or separate embodiments 46-63, wherein an initial release rate of the therapeutic agent from the polymer matrix is between about 0.5-10%/minute.

65. The apparatus of the combined or separate embodiments 46-64, wherein an initial release rate of the therapeutic agent from the polymer matrix is between about 1-10%/minute.

66. The apparatus of the combined or separate embodiments 46-65, wherein an initial release rate of the therapeutic agent from the polymer matrix is between about 2-10%/minute.

67. The apparatus of the combined or separate embodiments 46-66, wherein the hydrophilic component is PEG-PLGA.

68. The apparatus of the combined or separate embodiments 46-67, wherein the biodegradable polymer is a hydrophobic polymer selected from PLA, α-hydroxy acids, polycaprolactones, polyanhydrides, and co-polymers thereof.

69. The apparatus of the combined or separate embodiments 46-68, wherein the α-hydroxy acid is PLGA.

70. The apparatus of the combined or separate embodiments 46-69, wherein the microstructures are detachable from the substrate.

71. The apparatus of the combined or separate embodiments 46-70, wherein the therapeutic agent is selected from a drug, a small molecule, a peptide or protein, or a vaccine.

72. A microstructure apparatus, comprising:
  an approximately planar substrate having a first surface and a second surface opposed thereto;
  a microstructure array comprising a plurality of microstructures contacting the first surface of the substrate and fixedly attached thereto, the microstructures being formed of a polymer matrix comprising at least one polymer and at least one therapeutic agent;
  wherein a ratio of therapeutic agent to polymer in the matrix is low;
  wherein an initial release rate of the therapeutic agent from the polymer matrix is between about 0.05-10%/minute;
  wherein release of the therapeutic agent from the polymer matrix is sustained for a period of at least about 1-144 hours.

73. The apparatus of embodiment 72, wherein the ratio of therapeutic agent to polymer is between about 1:2 to 1:25.

74. The apparatus of the combined or separate embodiments 72-73, wherein the ratio of therapeutic agent to polymer is between about 1:2 to 1:20.

75. The apparatus of the combined or separate embodiments 72-74, wherein the ratio of therapeutic agent to polymer is between about 1:2 to 1:15.

76. The apparatus of the combined or separate embodiments 72-75, wherein the ratio of therapeutic agent to polymer is between about 1:2 to 1:10.

77. The apparatus of the combined or separate embodiments 72-76, wherein the ratio of therapeutic agent to polymer is between about 1:2 to 1:4.

78. The apparatus of the combined or separate embodiments 72-77, wherein the polymer matrix comprises at least one water insoluble, biodegradable polymer.

79. The apparatus of any the combined or separate embodiments 72-78, wherein the water insoluble, biodegradable polymer is selected from polylactide, polyglycolide, and co-polymers thereof.

80. The apparatus of the combined or separate embodiments 72-79, wherein the initial release rate is between about 0.5%/minute.

81. The apparatus of the combined or separate embodiments 72-80, wherein the initial release rate of the therapeutic agent from the polymer matrix is less than 10%/minute.

82. The apparatus of the combined or separate embodiments 72-81, wherein release of the therapeutic agent from the polymer matrix is sustained for a period of at least about 144 hours.

83. The apparatus of the combined or separate embodiments 72-82, wherein release of the therapeutic agent from the polymer matrix is sustained for a period of at least about 72 hours.

84. The apparatus of the combined or separate embodiments 72-83, wherein release of the therapeutic agent from the polymer matrix is sustained for a period of at least about 24 hours.

85. The apparatus of the combined or separate embodiments 72-84, wherein release of the therapeutic agent from the polymer matrix is sustained for a period of at least about 12 hours.

86. The apparatus of the combined or separate embodiments 72-85, wherein release of the therapeutic agent from the polymer matrix is sustained for a period of at least about 6 hours.

87. The apparatus of the combined or separate embodiments 72-86, wherein release of the therapeutic agent from the polymer matrix is sustained for a period of at least about 3 hours.

88. The apparatus of the combined or separate embodiments 72-87, wherein release of the therapeutic agent from the polymer matrix is sustained for a period of at least about 1 hour.

89. The apparatus of the combined or separate embodiments 72-88, wherein the therapeutic agent is selected from a drug, a small molecule, a peptide or protein, or a vaccine.

90. The apparatus of the combined or separate embodiments 72-89, wherein the microstructures are detachable from the substrate.

91. A method of making a sustained release microstructure apparatus, comprising:
  dissolving or suspending a therapeutic agent in a solvent to form a therapeutic agent solution or suspension;
  dissolving at least one water insoluble, biodegradable polymer in a solvent to form a polymer solution;
  mixing the therapeutic agent solution or suspension and the polymer solution or suspension to form a polymer matrix solution or suspension;
  dispensing the polymer matrix solution or suspension on a mold having an array of microstructure cavities;
  filling the microstructure cavities in the mold;
  removing excess solution or suspension polymer matrix on the mold surface; and
  drying the matrix to form a plurality of microstructures;
  dispensing a basement or backing layer on the mold surface;
  drying the basement or backing layer.

92. The method of embodiment 91, further comprising:
  affixing the basement or backing layer to a substrate.

93. The method of the combined or separate embodiments 91-92, further comprising:
  using a nonwoven or porous film double coated with adhesive to affix the basement or backing layer to a substrate.

94. The method of the combined or separate embodiments 91-93, wherein at least one of the solvents is selected from DMSO and acetonitrile.

95. The method of the combined or separate embodiments 91-94, wherein filling the microstructure cavities comprises pressurizing the mold.

96. The method of the combined or separate embodiments 91-95, wherein the therapeutic agent is crystalline, further comprising:
  heating the plurality of microstructures to about 110° C. for about 1 hour; and
  storing the microstructures in a dry cabinet for about 10 days.

97. The method of the combined or separate embodiments 91-96, wherein the heating is performed in a convection oven.

98. A method of modulating an initial release rate of a therapeutic agent from a microstructure apparatus comprising a plurality of microstructures formed of a polymer matrix comprising at least one polymer and at least one therapeutic agent, the method comprising:
  (a) wherein the at least one polymer comprises at least one high molecular weight polymer and at least one low molecular weight polymer, adjusting a ratio of the high molecular weight polymers to low molecular weight polymers in the polymer matrix to achieve a desired initial release rate of therapeutic agent from the polymer matrix;

(b) adjusting a ratio of therapeutic agent to polymer in the polymer matrix;

(c) adding at least one hydrophilic component to the polymer matrix; and/or (d) selecting a solvent for preparing the polymer matrix that provides a desired initial release rate.

99. The method of embodiment 98, wherein (a) comprises increasing the ratio of high molecular weight polymer in the matrix to increase the initial release rate.

100. The method of the combined or separate embodiments 98-99, wherein (a) comprises increasing the ratio of low molecular weight polymer in the matrix to decrease the initial release rate.

101. The method of the combined or separate embodiments 98-100, wherein (b) comprises increasing the ratio of therapeutic agent in the matrix to increase the initial release rate.

102. The method of the combined or separate embodiments 98-101, wherein (b) comprises decreasing the ratio of low molecular weight polymer in the matrix to decrease the initial release rate.

103. The method of the combined or separate embodiments 98-102, wherein (c) comprises adding the hydrophilic component as about 10-40% of the matrix to increase the initial release rate.

104. The method of the combined or separate embodiments 98-103, wherein the hydrophilic component is PEG-PLGA.

105. The method of the combined or separate embodiments 98-104, wherein the at least one polymer is a water insoluble, biodegradable polymer.

106. The method of the combined or separate embodiments 98-105, wherein the water insoluble, biodegradable polymer is selected from polylactide, polyglycolide, and co-polymers thereof.

107. The method of the combined or separate embodiments 98-106, wherein (d) comprises choosing one of DMSO or acetonitrile as the solvent.

108. The method of the combined or separate embodiments 98-107, wherein (d) comprises choosing DMSO as the solvent to lower the initial release rate.

109. The method of the combined or separate embodiments 98-108, wherein (d) comprises choosing acetonitrile as the solvent to increase the initial release rate.

110. A microstructure apparatus, comprising:

an approximately planar substrate having a first surface and a second surface opposed thereto; and a microstructure array comprising a plurality of microstructures contacting the first surface of the substrate and fixedly attached thereto;

wherein at least a portion of the microstructures has a distal portion dimensioned to penetrate a stratum corneum layer of a subject's skin, and a proximal portion that is dimensioned so that it does not penetrate the skin;

wherein the distal portion and proximal portion are each formed of a polymer matrix comprising (i) a biodegradable polymer, and (ii) at least one therapeutic agent.

111. The microstructure apparatus of embodiment 110, further comprising:

a backing layer positioned between the proximal portion and the substrate, the backing layer being formed of a polymer matrix comprising (i) a biodegradable polymer, and (ii) the at least one therapeutic agent.

112. The apparatus of the combined or separate embodiments 110-111, wherein the biodegradable polymer is a water soluble biodegradable polymer.

113. The apparatus of the combined or separate embodiments 110-112, wherein the biodegradable polymer is a water insoluble biodegradable polymer.

114. The apparatus of the combined or separate embodiments 110-113, wherein the therapeutic agent is selected from a drug, a small molecule, a peptide or protein, or a vaccine.

115. The apparatus of the combined or separate embodiments 110-114, wherein release of the therapeutic agent from the polymer matrix is sustained for a period of at least about 0.1-24 hours.

116. The apparatus of the combined or separate embodiments 110-115, wherein release of the therapeutic agent from the polymer matrix is sustained for a period of at least about 0.5-10 hours.

117. The apparatus of any the combined or separate embodiments 110-116, wherein release of the therapeutic agent from the polymer matrix is sustained for a period of at least about 0.5-4 hours.

118. The apparatus of the combined or separate embodiments 110-117, wherein release of the therapeutic agent from the polymer matrix is sustained for a period of at least about 0.5-4 hours.

119. The apparatus of the combined or separate embodiments 110-118, wherein release of the therapeutic agent from the polymer matrix is sustained for a period of at least about 0.1-1 hours.

120. The apparatus of the combined or separate embodiments 110-119, where the microstructure array is suitable to be worn for at least 1-24 hours.

121. A microstructure apparatus, comprising:

a substrate having a first surface and a second surface opposed thereto;

a plurality of microstructures extending outwardly from the first surface of the substrate;

at least a portion of the microstructures comprising at least one therapeutic agent; and an adhesive coating applied to at least one of a) at least a portion of at least some of the plurality of microstructures, or b) at least a portion of the substrate first surface between the microstructures.

122. The microstructure apparatus of embodiment 121, wherein at least a portion of the microstructures comprise a biodegradable distal layer and at least one non-biodegradable proximal layer positioned between the distal layer and the first surface of the substrate.

123. The microstructure apparatus of the combined or separate embodiments 121-122, wherein at least a portion of the microstructures are biodegradable.

124. The microstructure apparatus of the combined or separate embodiments 121-123, wherein the therapeutic agent is a drug, a small-molecule agent, a protein or peptide, or a vaccine.

125. The microstructure apparatus of the combined or separate embodiments 121-124, wherein the adhesive coating comprises an adhesive selected from a medical adhesive, a tissue adhesive, or a surgical adhesive.

126. The microstructure apparatus of the combined or separate embodiments 121-125, wherein the medical adhesive is selected from acrylic adhesives, silicone based adhesives, hydrogel adhesives, and synthetic elastomer adhesives.

127. The microstructure apparatus of the combined or separate embodiments 121-126, wherein the tissue adhesive is a cyanoacrylate polymer.

128. The microstructure apparatus of the combined or separate embodiments 121-127, wherein the cyanoacrylate polymer is selected from n-butyl-2-cyanoacrylate, and isobutyl cyanoacrylate.
129. The microstructure apparatus of the combined or separate embodiments 121-128, wherein the adhesive coating comprises a fibrin adhesive.
130. The microstructure apparatus of the combined or separate embodiments 121-129, wherein the adhesive coating comprises a bioactive film.
131. The microstructure apparatus of the combined or separate embodiments 121-130, wherein the adhesive coating comprises a pressure sensitive adhesive.
132. The microstructure apparatus of the combined or separate embodiments 121-131, wherein the pressure sensitive adhesive is an acrylic pressure sensitive adhesive.
133. The microstructure apparatus of the combined or separate embodiments 121-132, wherein the adhesive coating comprises a rubber-based adhesive.
134. The microstructure apparatus of the combined or separate embodiments 121-133, wherein the adhesive coating is biodegradable.
135. The microstructure apparatus of the combined or separate embodiments 121-134, wherein the adhesive coating is non-continuous.
136. The microstructure apparatus of the combined or separate embodiments 121-135, wherein the adhesive coating includes a plurality of holes.
137. The microstructure apparatus of the combined or separate embodiments 121-136, wherein the adhesive coating is porous.
138. The microstructure apparatus of the combined or separate embodiments 121-137, wherein the adhesive coating has a reduced adhesion over time.
139. The microstructure apparatus of the combined or separate embodiments 121-138, wherein the adhesive coating is applied to at least about 10-100% of the microstructures in the array.
140. The microstructure apparatus of the combined or separate embodiments 121-139, wherein about 10-95% of each coated microstructure has an adhesive coating.
141. The microstructure apparatus of the combined or separate embodiments 121-140, wherein the adhesive coating is applied to a distal portion of the microstructures.
142. The microstructure apparatus of the combined or separate embodiments 121-141, wherein the adhesive coating is applied to a proximal portion of the microstructures.
143. A microstructure apparatus, comprising:
a substrate having a first surface and a second surface opposed thereto;
a plurality of microstructures extending outwardly from the first surface of the substrate;
a plurality of openings extending through the substrate and positioned between at least some of the plurality of microstructures; and
an adhesive coating applied to at least a portion of the substrate second surface such that the adhesive is capable of contacting a subject's skin through the openings when placed on the skin.
144. The microstructure apparatus of embodiment 143, wherein the adhesive coating is applied to all or substantially all of the substrate second surface.
145. The microstructure apparatus of the combined or separate embodiments 143-144, wherein the adhesive coating is applied the substrate second surface in the region of the openings.
146. The microstructure apparatus of the combined or separate embodiments 143-145, further comprising a backing layer positioned over the adhesive coating.
147. The microstructure apparatus of the combined or separate embodiments 143-146, wherein at least a portion of the microstructures are at least partially biodegradable.
148. The microstructure apparatus of the combined or separate embodiments 143-147, wherein the therapeutic agent is a drug, a small-molecule agent, a protein or peptide, or a vaccine.
149. The microstructure apparatus of the combined or separate embodiments 143-148, wherein the adhesive coating comprises an adhesive selected from a medical adhesive, a tissue adhesive, or a surgical adhesive.
150. The microstructure apparatus of the combined or separate embodiments 143-149, wherein the medical adhesive is selected from acrylic adhesives, silicone based adhesives, hydrogel adhesives, and synthetic elastomer adhesives.
151. The microstructure apparatus of the combined or separate embodiments 143-150, wherein the tissue adhesive is a cyanoacrylate polymer.
152. The microstructure apparatus of the combined or separate embodiments 143-151, wherein the cyanoacrylate polymer is selected from n-butyl-2-cyanoacrylate, and isobutyl cyanoacrylate.
153. The microstructure apparatus of the combined or separate embodiments 143-152, wherein the adhesive coating comprises a fibrin adhesive.
154. The microstructure apparatus of the combined or separate embodiments 143-153, wherein the adhesive coating comprises a bioactive film.
155. The microstructure apparatus of the combined or separate embodiments 143-154, wherein the adhesive coating comprises a pressure sensitive adhesive.
156. The microstructure apparatus of the combined or separate embodiments 143-155, wherein the pressure sensitive adhesive is an acrylic pressure sensitive adhesive.
157. The microstructure apparatus of the combined or separate embodiments 143-156, wherein the adhesive coating comprises a rubber-based adhesive.
158. The microstructure apparatus of the combined or separate embodiments 143-157, wherein the adhesive coating is biodegradable.
159. The microstructure apparatus of the combined or separate embodiments 143-158, wherein the adhesive coating is non-continuous.
160. The microstructure apparatus of the combined or separate embodiments 143-159, wherein the adhesive coating includes a plurality of holes.
161. The microstructure apparatus of the combined or separate embodiments 143-160, wherein the adhesive coating is porous.
162. The microstructure apparatus of the combined or separate embodiments 143-161, wherein the adhesive coating has a reduced adhesion over time.
163. The microstructure apparatus of the combined or separate embodiments 143-162, wherein the adhesive coating is applied to at least about 10-100% of the microstructures in the array.
164. The microstructure apparatus of the combined or separate embodiments 143-163, wherein about 10-95% of each coated microstructure has an adhesive coating.
165. The microstructure apparatus of the combined or separate embodiments 143-164, wherein the adhesive coating is applied to a distal portion of the microstructures.

166. The microstructure apparatus of the combined or separate embodiments 143-165, wherein the adhesive coating is applied to a proximal portion of the microstructures.

167. A system comprising:
the microstructure apparatus of the combined or separate embodiments 1-166; and
an applicator for applying the microstructure apparatus to a patient's skin.

168. A method of delivering a therapeutic agent to a subject for an extended period of time, comprising:
applying a microstructure apparatus of any previous claim to a skin site of the subject;
adhering the microstructure apparatus to the skin;
delivering the therapeutic agent from the microstructure array to the subject; and
removing the microstructure apparatus after at least about 10 minutes.

169. The method of embodiment 168, wherein the microstructure apparatus is removed after at least about 15 minutes.

170. The method of the combined or separate embodiments 168-169, wherein the microstructure apparatus is removed after at least about 20 minutes.

171. The method of the combined or separate embodiments 168-170, wherein the microstructure apparatus is removed after at least about 30 minutes.

172. The method of the combined or separate embodiments 168-171, wherein the microstructure apparatus is removed after at least about 45 minutes.

173. The method of the combined or separate embodiments 168-172, wherein the microstructure apparatus is removed after at least about 1 hour.

174. The method of the combined or separate embodiments 168-173, wherein the microstructure apparatus is removed after at least about 1-24 hours.

175. The method of the combined or separate embodiments 168-174, wherein the microstructure apparatus is removed after at least about 1-5 days.

176. The method of the combined or separate embodiments 168-175, wherein at least about 10-100% of a total dose of the therapeutic agent is delivered to the subject.

177. The method of the combined or separate embodiments 168-176, wherein at least about 50-100% of a total dose of the therapeutic agent is delivered to the subject.

178. The method of the combined or separate embodiments 168-177, wherein at least about 60-100% of a total dose of the therapeutic agent is delivered to the subject.

179. The method of the combined or separate embodiments 168-178, wherein at least about 70-100% of a total dose of the therapeutic agent is delivered to the subject.

180. The method of the combined or separate embodiments 168-179, wherein at least about 75-100% of a total dose of the therapeutic agent is delivered to the subject.

181. The method of the combined or separate embodiments 168-180, wherein at least about 80-100% of a total dose of the therapeutic agent is delivered to the subject.

182. The method of the combined or separate embodiments 168-181, wherein at least about 90-100% of a total dose of the therapeutic agent is delivered to the subject.

183. The method of the combined or separate embodiments 168-182, wherein at least about 95-100% of a total dose of the therapeutic agent is delivered to the subject.

184. The method of the combined or separate embodiments 168-183, further comprising:
prior to applying the microstructure apparatus, positioning the microstructure apparatus on a plunger of an applicator;
actuating the applicator to release the plunger;
impacting the skin with the microstructure apparatus;
removing the applicator with the microstructure apparatus remaining on the skin site for an extended period of time.

185. The method of the combined or separate embodiments 168-184, further comprising:
pressing the microstructure apparatus against the skin site to push the adhesive through the openings and into contact with the skin site.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

What is claimed is:
1. A microstructure apparatus, comprising:
an approximately planar substrate having a first surface and a second surface opposed thereto; and
a microstructure array comprising a plurality of microstructures contacting the first surface of the substrate and fixedly attached thereto, at least a distal end of the microstructures being formed of a polymer matrix comprising:
(a) a formulation comprising:
  (i) a low molecular weight polylactic-co-glycolic acid (PLGA) polymer,
  (ii) a high molecular weight PLGA polymer, having a molecular weight that is higher than that of the low molecular weight PLGA polymer, where the low molecular weight PLGA polymer is present in excess of the high molecular weight PLGA polymer, and
  (iii) at least one therapeutic agent;
wherein the polymer matrix is prepared by a process comprising:
  dissolving the therapeutic agent (iii) in a solvent to form a solution or suspension and mixing said solution or suspension with the low molecular weight PLGA polymer (i) and the high molecular weight PLGA polymer (ii),
wherein the polymer matrix is composed for a substantially constant release profile of the therapeutic agent from the polymer matrix following an initial release rate of less than about 25 $\mu g/hr/cm^2$, where the substantially constant release profile is maintained for at least about one hour,
wherein the therapeutic agent is released for at least 30 hours following application to a subject's skin; and wherein the low molecular weight polymer and the high molecular weight polymer are present in a ratio of about 4:1.

2. The microstructure apparatus of claim 1, wherein the at least one low molecular weight PLGA polymer has a molecular weight not exceeding about 10K Da.

3. The microstructure apparatus of claim 1, wherein the at least one high molecular weight PLGA polymer having a molecular weight of at least about 50K Da.

4. The microstructure apparatus of claim 1, wherein the ratio of low molecular weight PLGA polymer to high molecular weight PLGA polymer is composed to provide for a substantially no-burst release of the therapeutic agent.

5. The microstructure apparatus of claim 1, wherein the ratio of low molecular weight PLGA polymer to high molecular weight PLGA polymer is composed to provide a desired release rate of the therapeutic agent from the polymer matrix.

6. The microstructure apparatus of claim 1, wherein the substantially constant release profile is maintained for at least about 30 hours.

7. The microstructure apparatus of claim 1, wherein the polymer matrix is composed for an overall release rate of the therapeutic agent of between about 0.25 pg/hr/cm$^2$ and 40 pg/hr/cm$^2$ over a defined period of time.

8. The microstructure apparatus of claim 1, wherein the polymer matrix is composed for an initial release rate of the therapeutic agent of between about 0.25 pg/hr/cm$^2$ and 40 pg/hr/cm$^2$ over a defined initial period of time.

9. The microstructure apparatus of claim 1, wherein at least a portion of the microstructures are detachable from the substrate.

10. The microstructure apparatus of claim 1, further comprising a backing layer positioned between a proximal portion of the plurality of microstructures and the substrate, the backing layer being formed of a second polymer matrix comprising:
 (i) a biodegradable polymer, and
 (ii) the at least one therapeutic agent.

11. The microstructure apparatus of claim 1, further comprising an adhesive coating applied to at least one of:
 (i) at least a portion of at least some of the plurality of microstructures,
 (ii) at least a portion of the substrate first surface between the microstructures, or
 (iii) the apparatus further including a plurality of openings extending through the substrate and positioned between at least some of the plurality of microstructures, the adhesive coating being applied to at least a portion of the substrate second surface such that the adhesive is capable of contacting a subject's skin through the openings when placed on the skin.

12. A method of making the microstructure apparatus of claim 1, where the microstructure apparatus is a sustained release microstructure apparatus comprising a polymer matrix of formulation (a) or formulation (b), the method comprising:
 (a) dissolving or suspending the therapeutic agent in a first solvent to form a therapeutic agent solution or suspension;
 (b) dissolving the at least one water insoluble, biodegradable polymer, the low molecular weight PLGA polymer or the high molecular weight PLGA polymer in a second solvent to form a polymer solution, wherein the second solvent can be the same or different from the first solvent;
 (c) mixing the therapeutic agent solution or suspension and the polymer solution to form a polymer matrix solution or suspension;
 (d) dispensing the polymer matrix solution or suspension on a mold having an array of microstructure cavities;
 (e) filling the microstructure cavities in the mold;
 (f) removing excess solution or suspension polymer matrix on the mold surface; and drying the matrix to form a plurality of microstructures;
 (g) dispensing a basement or backing layer on the mold surface; and
 (h) drying the basement or backing layer.

13. The method of claim 12, wherein the first solvent or the second solvent comprises DMSO or acetonitrile.

14. A method of delivering a therapeutic agent to a subject for an extended period of time, comprising:
 (a) applying the microstructure apparatus of claim 1 to a skin site of the subject;
 (b) adhering the microstructure apparatus to the skin; and
 (c) delivering the therapeutic agent from the microstructure array to the subject.

15. The method of claim 14, further comprising (d) removing the microstructure apparatus from the skin.

16. The method of claim 15, wherein removing the microstructure apparatus from the skin occurs after a period of at least about 10 minutes following the adhering step, at least about 15 following the adhering step or at least about 5 days following the adhering step.

17. The method of claim 14, further wherein applying the microstructure apparatus comprises:
 (a) positioning the microstructure apparatus on a plunger of an applicator;
 (b) actuating the applicator to release the plunger;
 (c) impacting the skin with the microstructure apparatus; and
 (d) removing the applicator with the microstructure apparatus remaining on the skin site.

* * * * *